United States Patent [19]

Siadak et al.

[11] Patent Number: 5,876,950
[45] Date of Patent: Mar. 2, 1999

[54] MONOCLONAL ANTIBODIES SPECIFIC FOR DIFFERENT EPITOPES OF HUMAN GP39 AND METHODS FOR THEIR USE IN DIAGNOSIS AND THERAPY

[75] Inventors: Anthony W. Siadak; Diane L. Hollenbaugh, both of Seattle; Lisa K. Gilliland, Bellevue; Marcia L. Gordon, Seattle; Jurgen Bajorath, Lynnwood; Alejandro A. Aruffo, Edmonds, all of Wash.

[73] Assignee: Bristol-Myers Squibb Company, New York, N.Y.

[21] Appl. No.: 379,057

[22] Filed: Jan. 26, 1995

[51] Int. Cl.[6] .......................... A61K 39/395; C07K 16/28
[52] U.S. Cl. .................. 435/7.23; 424/133.1; 424/135.1; 424/144.1; 424/154.1; 435/7.24; 435/343.2; 530/387.3; 530/388.75
[58] Field of Search ............................... 424/133.1, 144.1, 424/135.1, 154.1; 435/7.24, 7.32, 343.2; 530/388.7, 388.73, 388.75, 387.3

[56] References Cited

U.S. PATENT DOCUMENTS

| 4,816,567 | 3/1989 | Cabilly et al. | 530/387 |
| 5,474,771 | 12/1995 | Lederman et al. | 424/133.1 |
| 5,683,693 | 11/1997 | Noelle et al. | 424/144.1 |
| 5,747,037 | 5/1998 | Noelle et al. | 424/154.1 |

OTHER PUBLICATIONS

Alderson M.R. et al., CD40 Expression by Human Monocytes: Regulation by Cytokines and Activation of Monocytes by the Ligand for CD40, *J. Exp. Med.* 178:669–674, 1993.

Allen, R.C. et al., "CD40 Ligand Gene Defects Responsible for X–Linked Hyper–IgM Syndrome," *Science* 259:990–993, 1993.

Armitage, R.J. et al., "Molecular and Biological Characterization of a murine ligand for CD40," *Nature* 357:80–82, 1992.

Armitage, R.J. et al., "CD40 ligand is a T cell growth factor," *Eur. J. Immunol.* 23:2326–2331, 1993.

Aruffo, Alejandro et al., "The CD40 Ligand, gp39, is Defective in Activated T Cells from Patients with X–Linked Hyper–IgM Syndrome," *Cell* 72:291–300, 1993.

Barrett, T.B. et al., "CD40 Signaling Activates CD11a/CD18 (LFA–1)–Mediated Adhesion in B Cells," *J. Immunol.* 146:1722–1729, 1991.

Callard, R.E. et al., "CD40 ligand and its role in X–linked hyper–IgM syndrome," *Immunol. Today* 14;559–564,1993.

Clark, E.A. and Ledbetter, J.A., "Activation of human B cells mediated through two distinct cell surface differentiation antigens, Bp35 and Bp50," *Proc. Natl. Acad. Sci. USA*, 83:4494–4498, 1986.

Defrance, T. et al., "Interleukin 10 and Transforming Growh Factor β Cooperate to Induce Anti–CD40–activated naive human B Cells to Secrete Immunoglobulin A," *J. Exp. Med.* 175:671–682, 1992.

DiSanto, J.P. et al., "CD40 ligand mutations in X–linked immunodeficiency with hyper–IgM," *Nature* 361:541–543, 1993.

Fanslow, W.C. et al., "Soluble Forms of CD40 Inhibit Biologic Responses of Human B Cells," *J. Immunol.* 149:655–660, 1992.

Galy, A.H.M. and Spits, H., "CD40 is Functionally Expressed on Human Thymic Epithelial Cells," *J. Immunol.* 149:775–782,1992.

Gascan, H. et al., "Anti–CD40 Monoclonal Antibodies of CD4[+]T Cell Clones and IL–4 Induce igG4 and IgE Switching in Purified Human B Cells via Different Signaling Pathways," *J. Immunol.* 147:8–13, 1991.

Gordon, J. et al., "Synergistic interaction between interleukin 4 and anti–Bp50 (Cdw40) revealed in a noval B cell restimulation assya," *Eur. J. Immunol.* 17:1535–1438, 1987.

Gordon, J. et al., "Resting B Lymphocytes can be Triggered Directly through the Cdw40 (Bp50) Antigen," *J. Immunol.* 140:1425–1430, 1988.

Graf, D. et al., "Cloning of TRAP, a ligand for CD40 on human T cells," *Eur. J. Immunol.* 22:3191–3194, 1992.

Hollenbaugh, D. et al., "The human T cell antigen gp39, a member of the TNF gene family, is a ligand for the CD40 receptor: expression of a soluble form of gp39 with B cell co–stimulatory activity," *EMBO J.* 11:4313–4321, 1992.

Jabara, H.H. et al., "CD40 and IgE: synergism between Anti–CD40 Monoclonal Antibody and Interleukin 4 in the Induction of IgE Synthesis by Highly Purified Human B Cells," *J. Exp. Med.* 172:1861–1864, 1990.

Kinnon, E. and Levinsky, R., "The Molecular Basis of X–Linked Immunodeficiency Disease," *J. Inherit. Metab. Dis.* 15:674–682, 1992.

(List continued on next page.)

*Primary Examiner*—David Saunders
*Attorney, Agent, or Firm*—Christopher A. Klein; Brian W. Poor; Joseph M. Sorrentino

[57] ABSTRACT

The present invention provides monoclonal antibodies, antigen binding fragment and recombinant binding proteins specific for human gp39. These antibodies are specific for at least eight different epitopes on gp39. Hybridomas secreting specific antibodies which bind to these epitopes are also provided. Further, the present invention discloses the amino acid sequence of immunoglobulin light and heavy chain variable regions which bind to epitopes of gp39 and provide sFv and humanized antibodies which bind gp39. Also, provided are pharmaceutical compositions comprising the monoclonal antibodies, antigen binding fragments and recombinant binding proteins which bind gp39 and methods for using these compositions in diagnosing disease states, inhibiting B cell activation and for treating immunological disorders, such as autoimmune diseases, allergic responses, organ rejection and graft-versus-host disease. Antibodies of the present invention can also be used to image cells which express gp39 on their surface, such as tumor cells (e.g., lymphoma) and to target therapeutic agents to target cells.

50 Claims, 14 Drawing Sheets

OTHER PUBLICATIONS

Korthäuer, U. et al., "Defective expression of T–cell CD40 ligand causes X–linked immunodeficiency with hyper–IgM," *Nature* 361:539–541, 1883.

Lane, P. et al., "Activated human T cells express a ligand for the human B cell associated antigen CD40 which particpates in T cell–dependent activation of B lymphocytes," *Eur. J. Immunol.* 22:2573–2578, 1992.

Ledbetter, J.A. et al., "Augmentation of Normal and Malignant B cell Proliferation by Monoclonal Antibody to the B cell–Specific Antigen BP50 (CDW4)," *J. Immunol.* 138:788–794, 1987.

Lederman, S. et al., "Identification of a Novel Surface Protein on Activated CD4$^+$ T Cells that Induces Contact-–dependent B Cell Differentiation (Help)," *J. Exp. Med.* 175:1091–1101, 1992.

Noelle, R.J. et al., "CD40 and its ligand, an essential ligand–receptor pair for thymus–dependent B–cell activation," *Immunol. Today* 13:431–433, 1992.

Noelle, R.J. et al., "A 39–kDa protein on activated helper T cells binds CD40 and transduces the signal for cognate activation of B cells," *Proc. Natl. Acad. Sci. USA* 89:6550–6554, 1992.

Paulie, S. et al., "A p50 surface antigen restricted to human urinary bladder carcinomas and B lymphocytes," *Cancer Immunol. Immunother.* 20:23–28, 1985.

Rousset, F. et al., "cytokine–induced Proliferation and Immunoglobulin Production of Human B Lymphocytes Triggered through Their CD40 Antigen," *J. Exp. Med.* 173:705–710, 1991.

Shapira, S.K. et al., "Molecular Analysis of the Induction of Immunoglobulin E Synthesis in Human B Cells by Interleukin 4 and Engagement of CD40 Antigen," *J. Exp. Med.* 175:289–292 1992.

Spriggs, M.K. et al., "Recombinant Human CD40 Ligang Stimulates B Cell Proliferation and Immunoglobulin E Secretion," *J. Exp. Med.* 176:1543–1550,1992.

Stamenkovic, I. et al., "A B–lymphocyte activation molecule related to the nerve growht factor receptor and induced by cytokines in carcinomas," *EMBO J.* 8:1403–1410, 1989.

Uckun, F.M. et al., "Stimulation of Protein Tyrosine Phosphorylation, Phosphoinositide Turnover, and Multiple Previously Unidentified Serine/Threonine–specific Protein Kinases by the Pan–B–cell receptor CD40/Bp50 at Discrete Developmental Stages of Human B–cell Ontogeny," *J. Biol. Chem.* 266:17478–17485, 1991.

Young, L.S. et al., "Identification of a Human Epithelial Cell Surface Protein Sharing an Epitope with the C3d/Epstein-–Barr Virus Receptor Molecule of B Lymphocytes," *Int. J. of Cancer* 43:786–794, 1989.

Zhang, K. et al., "CD40 Stimulation Provides an IFN–γ–independent and IL–4–deoebdebt Differentiation Signal Directly to Human B Cells for IgE Production," *J. Immunol.* 146:1836–1842, 1991.

```
                                         Leader                              1
          ⎛ M   S   V   P   T   Q   V   L   G   L   L   L   W   L   T   G   A   R   C ⎞ D   I
           ATGAGTGTGCCCACTCAGGTCCTGGGGTTGCTGCTGCTGTGGCTTACAGGTGCCAGATGTGACATC 10                              20
           Q   M   T   Q   S   P   A   S   L   S   A   S   V   G   E   T   V   T   I   T   C | R
           CAGATGACTCAGTCTCCAGCCTCCCTATCTGCATCTGTGGGAGAGACTGTCACCATCACATGTCGA CDR1            30                                    40
          | A   S   E   T   I   Y   S   Y   L   A | W   Y   Q   Q   K   Q   G   R   S   P   Q   L
           GCAAGTGAGACTATTTACAGTTATTTAGCTTGGTATCAGCAGAAACAGGGAAGATCTCCTCAGCTC 50          CDR2                  60
           L   V   Y | N   A   K   T   L   A   E | G   V   P   S   R   F   S   G   S   G   S   G
           CTGGTCTATAATGCAAAAACCTTAGCAGAAGGTGTGCCATCAAGGTTCAGTGGCAGTGGATCAGGC 70                              80                              90
           T   Q   F   S   L   K   I   N   S   L   Q   P   E   D   F   G   S   Y   Y   C | Q   H
           ACACAGTTTTCTCTGAAGATCAACAGCCTGCAGCCTGAAGATTTTGGGAGTTATTACTGTCAACAT CDR3                        100
          | H   Y   N   T   P   L   T | F   G   T   G   T   K   L   E   L   K   R
           CATTATAATACTCCGCTCACGTTCGGTACTGGGACCAAGCTGGAGCTGAAACGG
                                         Jκ5
```

FIG. 1A

```
                              Leader                              1
   (M  N  F  G  F  S  L  I  F  L  V  L  V  L  K  G  V  Q  C) E  V  K
   ATGAACTTCGGGTTCAGCTTGATTTTCCTTGTCCTTGTTTTAAAAGGTGTCCAGTGTGAAGTGAAG 10                              20
   L  V  E  S  G  G  G  L  V  K  P  G  G  S  L  K  L  S  C  T  T  S
   CTGGTGGAGTCTGGGGGAGGCTTAGTGAAGCCTGGAGGGTCCCTGAAACTCTCCTGTACAACCTCT 30       CDR1                 40
   G  F  T  F  N │N  Y  A  M  S│ W  V  R  Q  T  P  E  K  R  L  E  W
   GGATTCACTTTCAATAACTATGCCATGTCTTGGGTTCGCCAGACTCCAGAGAAGAGGCTGGAGTGG 50                     CDR2       60
   V  A │S  I  S  S  G  D  S  T  Y  Y  P  D  S  V  R  G│ R  F  T  I
   GTCGCATCCATTAGTAGTGGTGATAGCACCTACTATCCAGACAGTGTGAGGGGCCGATTCACCATC 70                           80    82 a  b  c
   S  R  D  N  A  R  N  I  L  Y  L  Q  M  S  S  L  R  S  E  D  T  A
   TCCAGAGATAATGCCAGGAACATCCTGTATCTGCAAATGAGCAGTCTGAGGTCTGAGGACACGGCC 90              CDR3       100 a  b  c
   M  Y  Y  C  A  R │H  Y  D  Y  D  S  Y  A  M  D│ Y  W  G  Q  G  T
   ATGTATTACTGTGCAAGGCACTATGATTACGACAGCTATGCTATGGACTACTGGGGTCAAGGAACC
                                                  ‾‾‾‾‾‾‾‾‾‾‾‾‾‾‾‾‾‾‾
                                                            JH2

110
   S  V  T  V  S  S
   TCAGTCACCGTCTCCTCA               FIG. 1B
```

7 VL NUCLEOTIDE AND DEDUCED AMINO ACID SEQUENCE

```
                    Leader                                                1
    M  E  T  D  T  L  L  W  V  L  L  W  V  P  G  S  T  G  D  I
   ATGGAGACAGACACACTCCTGCTATGGGTGCTGCTGCTCTGGGTTCCAGGTTCCACTGGTGACATT 10                          20
    V  L  T  Q  S  P  V  S  L  A  V  S  L  G  Q  R  V  T  I  S  C  R
   GTGCTGACACAGTCTCCTGTTTCCTTAGCTGTATCTCTGGGGCAGAGGGTCACCATCTCATGCAGG CDR1  27  a  b  c  d      30                              40
    A  S  Q  S  V  S  S  T  N  S  Y  M  H  W  Y  Q  Q  K  P  G  Q
   GCCAGCCAAAGTGTCAGTTCATCTACCAATAGTTATATGCACTGGTACCAACAGAAACCAGGACAG 50      CDR2                    60
    P  P  K  L  L  I  K  Y  A  S  N  L  E  S  G  V  P  A  R  F  S  G
   CCACCCAAACTCCTCATCAAGTATGCATCCAACCTAGAATCTGGGGTCCCTGCCAGGTTCAGTGGC 70                          80
    S  G  S  G  T  D  F  T  L  N  I  H  P  V  E  E  E  D  T  A  T  Y
   AGTGGGTCTGGGACAGACTTCACCCTCAACATCCATCCTGTGGAGGAGGAGGATACTGCAACATAT 90      CDR3                    100
    Y  C  Q  H  S  W  E  I  P  F  T  F  G  S  G  T  K  L  E  I  R  R
   TACTGTCAGCACAGTTGGGAGATTCCATTCACGTTCGGCTCGGGGACAAAGTTGGAAATAAGACGG
                                          JK4
```

FIG. 2A

7 VH NUCLEOTIDE AND DEDUCED AMINO ACID SEQUENCE

```
            Leader                                    1
 ( M  G  W  S  W  I  F  L  F  L  L  S  G  T  G  V  L  S ) E  V  Q
  ATGGGATGGAGCTGGATCTTTCTCTTTCTCTTGTCAGGAACTGGAGGTGTCCTCTCTGAGGTCCAG 10                                  20
   L  Q  Q  S  G  P  E  L  V  K  P  G  A  S  V  K  M  S  C  K  A  S
  CTGCAACAGTCTGGACCTGAACTGGTGAAACCTGGGGCTTCAGTGAAGATGTCCTGCAAGGCTTCT 30        CDR1                   40
   G  Y  T  F  T  [ D  Y  Y  M  K ] W  V  K  Q  S  H  G  K  S  L  E  W
  GGATTCACTTTCAATAACTATGCCATGTCTTGGGTTCGCCAGACTCCAGAGAAGAGGCTGGAGTGG 50    52 a       CDR2             60
   I  G  [ N  I  N  P  N  N  G  D  T  F  F  N  Q  K  F  E  G ] K  A  T
  ATTGGAAATATTAATCCTAACAATGGTGATACTTTCTTCAACCAGAAGTTCGAGGGCAAGGCCACG 70                      80     82 a  b  c
   L  T  V  D  K  S  S  S  A  A  Y  M  Q  L  N  S  L  T  S  E  D  S
  TTGACTGTAGACAAATCCTCCAGCGCAGCCTACATGCAGCTCAACAGCCTGACATCTGAAGACTCT 90              CDR3      100 a
   A  V  Y  Y  C  A  R  [ G  P  G  T  N  Y  F  D  Y ] W  G  Q  G  T  T
  GCAGTCTATTACTGTGCAAGAGGGCCTGGGACGAACTACTTTGACTACTGGGGCCAAGGCACCACT
                                                    JH2

110
   L  T  V  S  S
  CTCACAGTCTCCTCA
```

MONOCLONAL ANTIBODIES SPECIFIC FOR DIFFERENT EPITOPES OF HUMAN GP39 AND METHODS FOR THEIR USE IN DIAGNOSIS AND THERAPY

BACKGROUND OF THE INVENTION

A successful immune response requires coordinated interaction of multiple cell types. The interaction between T-helper cells (Th) and antigen-presenting cells (APC) such as B cells, monocytes, and dendritic cells results from complex communications involving signals received through soluble cytokines or membrane-bound proteins as well as adhesive interactions. Many of these signals are not specific to a directed immune response and the proteins are broadly distributed.

A number of important T cell surface proteins involved in cell-cell interactions have been identified including CD2, CD4, CD8, CD28, LFA-1, CTLA-4 and gp39. These proteins participate in cell-cell contact by binding to their counter-receptors on APC and provide important costimulatory signals to T cells which modulate signals received through the T-cell antigen receptor. These costimulatory signals are necessary for the T cell to become fully engaged and express both membrane-bound and soluble factors required for the proper activation of the T cell-dependent effector cells (B cells, natural killer cells, monocytes, neutrophils, etc.). The gp39/CD40 T cell ligand/B cell receptor pair plays a critical role in the humoral immune response. In vitro studies have shown that this receptor/ligand pair is involved in B cell proliferation, antibody and cytokine production and cell viability. Studies in vivo, both through blocking with a monoclonal antibody or by observation of a genetic defect in gp39, have validated the in vitro results, and extended them to the requirement for a functional gp39 for germinal center formation during immune response to antigen.

CD40 is a 50 kDa type I membrane glycoprotein expressed by B cells, macrophages, follicular dendritic cells, thymic epithelium, normal basal epithelium, some carcinoma and melanoma-derived cell lines (Clark and Ledbetter 1986, *Proc. Nat'l. Acad. Sci. USA* 83:4494; Paerlie et al. 1985, *Cancer Immunol. Immunother.* 20:23, Ledbetter et al. 1987, *J. Immunol.* 138:788; Young et al. 1989, *Int. J. Cancer* 43:786; Galy and Spits 1992, *J. Immunol.* 149:775, Alderson et al. 1993, *J. Exp. Med* 178:669) and recently has been reported to be expressed on T cells (Armitage et al. 1993, *Eur. J. Immunol.* 23: 2326). It has been shown to be an important signaling molecule with a range of downstream effects in multiple systems. Early studies showed that CD40 was involved in B cell activation. Crosslinking CD40 with anti-CD40 monoclonal antibody induces B cell aggregation via LFA-1 (Gordon et al. 1988, *J. Immunol.* 140:1425, Barrett et al., 1991, *J. Immunol.* 146:1722), increases Ser/Thr (Gordon et al. 1988, supra) and Tyr (Uckun et al. 1991, *J. Biol. Chem.* 266:17478) phosphorylation of a number of intracellular substrates and provides a "competence" signal that allows B cells to proliferate and undergo class switching when stimulated with the appropriate second signal. For example, anti-CD40 monoclonal antibody can synergize with PMA (Gordon et al. 1987, *Eur. J. Immunol.* 17:1535) or anti-CD20 monoclonal antibody (Clark and Ledbetter 1986, supra) to induce B cell proliferation, with IL-4 to induce B cell proliferation (Gordon et al. 1987, supra; Rousset et al. 1991, *J. Exp. Med.* 172:705) and IgE secretion (Jabara et al. 1990, *J. Exp. Med.* 172:1861; Gascan et al. 1991, *J. Immunol.* 147:8; Rousset et al. 1991, supra; Zhang et al. 1991, *J. Immunol.* 146.1836, Shapira et al. 1992, *J. Exp. Med.* 175:289) and with IL-10 and TGF-β to induce IgA secretion by sIgD$^+$ B cells (DeFrance et al. 1992, *J. Exp. Med.* 175:671).

Isolation of a cDNA clone encoding human CD40 (Stamenkovic et al. 1989, *EMBO J.* 8:1403) shows that CD40 has a significant homology to the nerve growth factor receptor family. Using a soluble form of CD40, CD40-immunoglobulin fusion protein (CD40-Ig) (Armitage et al. 1992, *Nature* 357:80; Lane et al. 1992, *Eur. J. Immunol.* 22:2573; Noelle et al. 1992, *Proc. Nat'l. Acad. Sci. USA* 89:6550), it was found that the CD40 ligand (gp39, CD40-L), a protein of approximately 39 kDa, was expressed by activated human and murine T cells. In addition, blocking studies with CD40-Ig (Fanslow et al. 1992, *J. Immunol.* 149:655; Noelle et al. 1992, supra) or an anti-murine gp39 monoclonal antibody (MR1) Noelle et al. 1992, supra) showed that preventing gp39-CD40 binding resulted in inhibition of B cell biological responses.

Complementary DNA encoding both murine (Armitage et al. 1992, *Nature* 357:80) and human (Hollenbaugh et al. 1992, *EMBO J.* 11:4313; Spriggs et al. 1992, *J. Exp. Med.* 176:1543) gp39 or a soluble recombinant form of gp39 and IL-4 or gp39 and IL-10 can drive human B cells to secrete IgE and IgA, or IgG and IgM, respectively (Aruffo et al. 1993, *Cell* 72:291). Taken together, these results suggest that gp39 may be a T cell "switch" responsible for some aspects of B cell differentiation and isotype switching (Noelle et al. 1992, *Immunol. Today* 13:431).

Recently, the gene encoding gp39 was mapped to Xq26, the X chromosome region where the gene responsible for hyper-IgM syndrome (HIM) had previously been mapped (Aruffo et al. 1993, *Cell* 72:291). The gp39 molecules in the HIM patients were found to be functionally abnormal. Activated T cells have been found to produce normal levels of mRNA, but the gp39 encoded is defective (Aruffo et al. 1993, supra; DiSanto et al. 1993, *Nature* 361:541).

Hyper-IgM syndrome is one of at least seven inherited immunodeficiencies mapped to the X-chromosome (Kinnon and Levinsky 1992, *J. Inherit. Metab Dis.* 15:674). The disease is characterized by low or absent IgG, IgA and IgE levels, normal or elevated levels of IgM, normal numbers of recirculating B cells, susceptibility to bacterial and opportunistic infections (including *Pneumocystic carinii*), no germinal centers, autoimmunity, neutropenia, X-linked and autosomal forms, and gp39 ligand gene defects in the X-linked form of the disease. Common Variable Immunodeficiency (CVI) is another group of immunodeficiency disorders characterized by abnormal antibody responses and recurrent bacterial infections. Clinical presentations of CVI are diverse, as the disorders described by the term include a wide variety of as yet uncharacterized defects. Disease states described as CVI commonly show decreased or absent serum IgG and IgA, while the levels of IgM may be normal or decreased. Although most CVI patients have normal T cell numbers and responses, some may have decreased numbers, abnormal CD4/CD8 cell ratios or abnormal T cell function. There is also an increased probability of autoimmune antibodies in this patient population.

Mutations in the gene encoding gp39 result in deletions giving rise to frame shifts and premature stop codons, or point mutations resulting in amino acid substitutions (Allen et al. 1993, *Science* 259:990; DiSanto et al. 1993, supra; Fuleichan et al. 1993, supra, Korthauer et al. 1993, supra; Aruffo et al. 1993, supra; Collard et al. 1993, *Immunol. Today* 14:559). The effect of these mutations on expression of gp39 by activated T cells has been examined using soluble CD40-Ig, polyclonal antibody raised against a gp39 bacterial fusion protein (anti-TRAP) (Graf et al. 1992, *Eur. J. Immunol* 22:3191; Korthauer et al. 1993, *Nature* 361:539) and a gp39 specific monoclonal antibody 5c8 (Lederman et al. 1992, *J. Exp. Med.* 75:1091). Staining with soluble CD40-Ig, gp39 expression was found to be absent, while that for anti-TRAP was normal on T cells from one out of three patients tested, which was confirmed using the monoclonal antibody. These results show that expression of gp39 is variable in HIM patients and it has been suggested that further work is needed to determine whether the variation in surface expression of mutant forms of gp39 correlates with HIM disease severity. In the absence of a family history of X-HIM, the disease is difficult to distinguish from CVI. The methods currently used to identify a defect in gp39 as the causative agent in X-HIM include the sequencing of nucleotides comprising the gp39 gene from cDNA formed from mRNA isolated from in vitro activated lymphocytes that do not bind CD40, but do contain mRNA encoding gp39. This method has been used to show one patient diagnosed with CVI actually suffers from hyper IgM syndrome. However, the methods are laborious and would be very expensive to use on a more generalized basis.

What is needed in the art are additional monoclonal antibodies reactive with different epitopes of gp39 which can be easily used to assay for mutant forms of gp39 and for other purposes in diagnostics to distinguish between common variable immunodeficiency and X-linked hyper-IgM, and in therapeutic methods to modulate disease states responsive to interactions between CD40 and its ligand gp39.

SUMMARY OF THE INVENTION

This invention provides for monoclonal antibodies capable of binding to at least eight separate epitopes on human gp39. The invention further provides for antigen binding fragments and recombinant binding protein derived from those monoclonal antibodies which also bind to gp39. Also provided are specific hybridomas which secrete monoclonal antibodies which bind to the eight epitopes on gp39 disclosed.

In one embodiment of the present invention, the monoclonal antibody, antigen binding fragment or recombinant binding protein thereof, is characterized by its binding to a mutant form of human gp39 and wild-type gp39 with a similar avidity when the mutants of gp39 comprise the replacement of tyrosine 145, asparagine 180 or phenylalanine 201 and glutamic acid 202 with alanine, and also has a poor binding avidity to a mutant form of gp39 when compared to the binding avidity to wild-type gp39 when the mutant comprises glutamic acid 129, serine 131 and tyrosine 135, or lysine 143 replaced by alanine; and further does not react with gp39 by Western blot. Specific examples of monoclonal antibodies having these characteristics are those secreted by hybridomas as 39-1.3 designated ATCC HB 11822 39-1.122 designated ATCC HB 11816 or 39-1.138 designated ATCC HB 11821.

In a second embodiment, the monoclonal antibody, antigen binding fragment or recombinant binding protein thereof is characterized by its binding to a mutant form of human gp39 with a somewhat reduced avidity when compared to the binding avidity to wild-type gp39 when the mutant form of gp39 comprises tyrosine 145, asparagine 180 or phenylalanine 201 and glutamic acid 202 are replaced by alanine, and further has a poor binding avidity to a mutant gp39 compared to the binding avidity to wild-type gp39 when the mutant form of gp39 comprises glutamic acid 129, serine 131 and threonine 135, or lysine 143 replaced by alanine, and also does not react with gp39 by Western blot. Specific examples of a monoclonal antibody with these characteristics includes that secreted by hybridoma 39-1.59 designated ATCC HB 11815.

In a third embodiment of the present invention, the monoclonal antibody, antigen binding fragment or recombinant binding protein thereof is characterized by its binding to a mutant form of human gp39 with a somewhat reduced binding avidity when compared to the binding avidity to wild-type gp39 when the mutant of gp39 comprises serine 131 and threonine 135, tyrosine 145, asparagine 180 or phenylalanine 201 and glutamic acid 202 are replaced by alanine. The antibody is further characterized by having poor binding avidity to a mutant of gp39 when compared to the binding avidity to wild-type gp39 wherein the mutant form of gp39 comprises glutamic acid 129, or lysine 145 replaced by alanine. Further, the antibody does not react with gp39 by Western blot. Specific examples of monoclonal antibodies having these characteristics are those secreted by the hybridoma 39-1.37 designated ATCC HB 11813 or 39-1.132 designated ATCCHB 11809.

In another embodiment of the present invention, the monoclonal antibody, antigen binding fragment or recombinant binding protein thereof is characterized by binding to a mutant form of human gp39 with a somewhat reduced binding avidity when compared to the binding avidity to wild-type gp39 when the mutant form of gp39 comprises serine 131 and threonine 135, tyrosine 145, asparagine 180, or phenylalanine 201 and glutamic acid 202 are replaced by alanine; and further has a poor binding avidity to a mutant of gp39 compared to the binding avidity to wild-type gp39 when the mutant form of gp39 comprises glutamic acid 129, or lysine 143 replaced by alanine. The antibodies of this group also react with gp39 by Western blot. Specific examples of monoclonal antibodies having these characteristics include those secreted by hybridomas 39-1.124 designated HB 11819 and 39-1.156 designated TCCHB 11817.

In a further embodiment of the present invention, the monoclonal antibody, antigen binding fragment or recombinant binding protein thereof is characterized by binding to a mutant form of human gp39 with a somewhat reduced or similar binding avidity when compared to the binding avidity to wild-type gp39 when the mutant form of gp39 comprises glutamic acid 129, serine 131 and threonine 135, tyrosine 145, asparagine 180 or phenylalanine 201 and glutamic acid 202 replaced by alanine, and further has a poor binding avidity to a mutant of gp39 comprising lysine 143 replaced by alanine than to wild-type gp39. The antibody is further characterized by the inability to bind gp39 in a Western blot. Specific examples of monoclonal antibodies having these characteristics are those secreted by the hybridomas 39-1.7 designated 11812, 39-1.128 designated ATCC HB 11818 and 39-1.26 designated ATCC HB 11820.

In yet another embodiment of the present invention, the monoclonal antibody, antigen binding fragment or recombinant binding protein thereof is characterized by its binding to mutant form of human gp39 and to wild-type gp39 with a similar binding avidity when the mutant comprises glutamic acid 129, serine 131 and threonine 135, tyrosine 145, or asparagine 180 replaced by alanine. The antibody is further characterized by having poor binding avidity to a mutant human gp39 when compared to the binding avidity to wild-type gp39 when the mutant form comprises phenylalanine 201 and glutamic acid 202 replaced by alanine and has a somewhat reduced binding avidity to a mutant gp39 when compared to the binding avidity to wild-type gp39 when the mutant form comprises lysine 143 replaced by alanine. Also, the monoclonal antibody binds to gp39 by Western blot. Specific examples of monoclonal antibodies having these characteristics include those secreted by the hybridomas 39-1.77 designated ATCC HB 11814, 39-1.106 designated ATCC HB 11811 and 39-1.134 designated ATCC HB 11810.

In a further embodiment of the present invention, the monoclonal antibody, antigen binding fragment or recombinant binding protein thereof is characterized by its binding to a mutant form of human gp39 and wild-type gp39 with a similar binding avidity when the mutant gp39 comprises glutamic acid 129, serine 131 and threonine 135, lysine 143, tyrosine 145 or asparagine 180 replaced by alanine, and has a poor binding avidity to a mutant gp39 compared to the binding avidity to wild-type gp39 when the mutant form of gp39 comprises phenylalanine 201 and glutamic acid 202 replaced by alanine. The antibody is further characterized by its ability to bind to gp39 by Western blot. A specific example of a monoclonal antibody having these characteristics is the monoclonal antibody secreted by the hybridomas 39-1.29 designated ATCC HB 11808.

In another embodiment of the present invention, the monoclonal antibody, antigen binding fragment or recombinant binding protein is characterized by binding to a mutant form of human gp39 and wild-type gp39 with a similar binding avidity when the mutant form of gp39 comprises glutamic acid 129, serine 131 and threonine 135, tyrosine 145, or asparagine 180 replaced by alanine. The antibody is also characterized by having a somewhat reduced binding avidity to a mutant gp39 when compared to wild-type gp39 when the mutant comprises lysine 143 replaced by alanine and also does not bind to gp39 by Western blot. A specific example of a monoclonal antibody having these characteristics is the monoclonal antibody secreted by the hybridoma 39-7.3E12 designated HB 11823.

In still a further embodiment of the present invention, the monoclonal antibody, antigen binding fragment or recombinant binding protein is characterized by not being highly reactive with a mutant human gp39 when the mutant comprises the glutamic acid at position 129, the serine at position 131 and the threonine at position 135, the tyrosine at position 145, or phenylalanine at position 201 and glutamic acid at position 202 replaced by alanine. Or, the monoclonal antibody is characterized as not being similarly reactive with a mutant of human gp39 when the mutant comprises the asparagine at position 180 or the lysine at position 143 is replaced by alanine. These antibodies can also be characterized by their binding or lack of binding to gp39 by Western blot.

Each of the groups of monoclonal antibodies recognize epitopes of gp39 and can be manipulated either chemically or by recombinant methods that generate either antigen binding fragments or recombinant binding proteins. Examples of antigen binding fragments are the Fab, (Fab')$_2$ or Fv created by enzyme digestion of whole antibody. Recombinant binding proteins of the present invention include any molecule which maintains the antigen specificity of the parental antibody and has been recombined with other amino acid residue sequences. Examples include chimeric antibodies, sFvs, humanized antibodies and fusion molecules.

In still another embodiment of the present invention, the monoclonal antibodies or recombinant binding proteins can be conjugated to a detectable marker or a therapeutic agent. Examples of detectable markers include fluorophores, radioactive isotopes, enzymes or chromophores. Therapeutic agents contemplated by the present invention can include radioisotopes, toxin, or a chemotherapeutic agent, such as a cytotoxic drug. In addition to conjugation techniques, the recombinant binding proteins of the present invention can be constructed to form fusion proteins that comprise a variable region derived from a monoclonal antibody of the present invention and an enzyme, protein toxin or proteinaceous therapeutic agent.

In yet another embodiment of the present invention, a method for the detection of X-linked hyper IgM syndrome is disclosed. The method comprises the steps of isolating peripheral blood lymphocytes from a patient suspected of having symptoms associated by the syndrome, activating the peripheral blood lymphocytes, fixing and permeabilizing the isolated and activated peripheral blood lymphocytes, admixing a monoclonal antibody described with the activated, fixed and permeabilized peripheral blood lymphocytes, and detecting antibody bound to the cells. The antibody can be labeled with a detectable marker or can be unlabeled. When used unlabeled, a further step of adding a secondary antibody (which is labeled) specific for the first antibody is carried out prior to the detection step. The detectable marker can be, for example, a fluorophore, radioactive isotope, enzyme or chromophore.

Further, the present invention provides hybridomas which secrete specific antibodies reactive with each of the epitopes described by the present invention. Each of these hybridomas was deposited with the American Type Culture Collection, 10801 University Boulevard, Manassas Va. 20110 on Jan. 20, 1995 under the conditions of the Budapest Treaty.

In yet another embodiment of the present invention, an isolated and purified nucleic acid sequence which encodes amino acid sequences for immunoglobulin light and heavy chains of immunoglobulin molecules which recognize epitopes of human gp39 are described by the present invention. In particular, the nucleic acid sequence encodes an amino acid sequence of the immunoglobulin light chain variable region depicted in Sequence ID# 12 and in Sequence ID# 16. Also disclosed are specific nucleotide sequences which encode these amino acid sequences. Those are depicted in Sequence ID#s 11 and 15. Also, the nucleic acid sequences which encode immunoglobulin heavy chain variable regions having the amino acid residue sequence depicted in Sequence ID# 14 and Sequence ID# 18 are provided. Particular nucleotide sequences which encode the amino acid residue sequences are provided in Sequence ID# 15 and Sequence ID# 17.

The present invention also provides pharmaceutical compositions comprising the monoclonal antibodies, antigen binding fragments or recombinant binding proteins thereof described herein combined with a pharmaceutically acceptable carrier. These compositions can include the monoclonal antibody, antigen binding fragment, or recombinant binding protein conjugated to a detectable marker or therapeutic agent.

Methods are also provided for using these pharmaceutical compositions to inhibit the activation of B cells in an animal by administering an effective amount of one of the compositions described above. The animal provided with the composition can include mice, rats, rabbits and humans. The inhibition of the activation of B cells can prevent an autoimmune response, the rejection of a transplanted organ, graftversus-host disease, an allergic response or an inflammatory response. Autoimmune diseases preventable using this method can include psoriasis, rheumatoid arthritis, systemic lupus erythematosus or diabetes mellitus, among others.

Further, the present invention provides methods for imaging cells expressing gp39 on their surface in a patient which comprise administering to a patient a pharmaceutical composition including a monoclonal antibody described above conjugated to a detectable marker under conditions permitting the formation of antibody/antigen complex on the surface of the cells expressing gp39, and detecting the presence of the antibody/antigen complex as indicated by the presence of the detectable markers.

DESCRIPTION OF THE FIGURES

FIG. 1A provides the nucleotide sequence for 106 VL (Seq. ID. #11) and the deduced amino acid sequence (Seq. ID. #12). FIG. 1B provides the nucleotide sequence for 106 VH (Seq. ID. #13) and the deduced amino acid sequence (Seq. ID. #14). The leader sequences are encircled and the complimentarity determining regions are shown in boxes. The VL is a member of the murine kappa V subfamily and the V gene segment has rearranged with Jκ 5 (FIG. 1A, underlined). The VH is a member of the murine III (D) subgroup. The heavy chain V gene has rearranged with JH2 (FIG. 1B, underlined).

FIG. 2A provides the nucleotide sequence for 7 VL (Seq. ID. #15) and the deduced amino acid sequence (Seq. ID. #16). FIG. 2B provides the nucleotide sequence for 7 VH (Seq. ID. #17) and the deduced amino acid sequence (Seq. ID. #18). The leader sequences are encircled and the complimentarity determining regions are shown in boxes. The VL is a member of the murine kappa II subfamily and the V gene segment has rearranged with Jκ 4 (FIG. 2A, underlined). The VH is a member of the murine II(A) subgroup. The heavy chain V gene has rearranged with JH2 (FIG. 2B, underlined).

FIG. 6 depicts the 106 VH humanization template. The original murine sequence is shown in the fourth row (m106, Seq. ID. #30) with the closest murine sequence beneath it (a suitable germline sequence having only three residues in the H2 loop was not available; instead, a rearranged sequence was chosen that had an overall high homology to 106 VH and also had a three residue H2 loop). The chosen human template sequence is shown in the second row (human template, Seq. ID. #32) with its human consensus sequence above it (human VHIII/JH4 consensus). The humanized 106 VH sequence (h106, Seq. ID. #31) is shown between the human template and the murine 106 VH sequence. It consists essentially of human framework residues and murine hypervariable residues (outlined with a double line). The H1, H2 and H3 loops are outlined with a single line and structural determinants as defined by Chothia (supra) are shown by asterisks. Human or murine residues differing from the humanized 106 VH are double underlined. The three residues at positions 24, 55 and 56 are residues that appear to reside in sites of high mutation rate. The human JH was chosen on the basis of homology to 106 JH.

DETAILED DESCRIPTION OF THE INVENTION

Figure 3A:
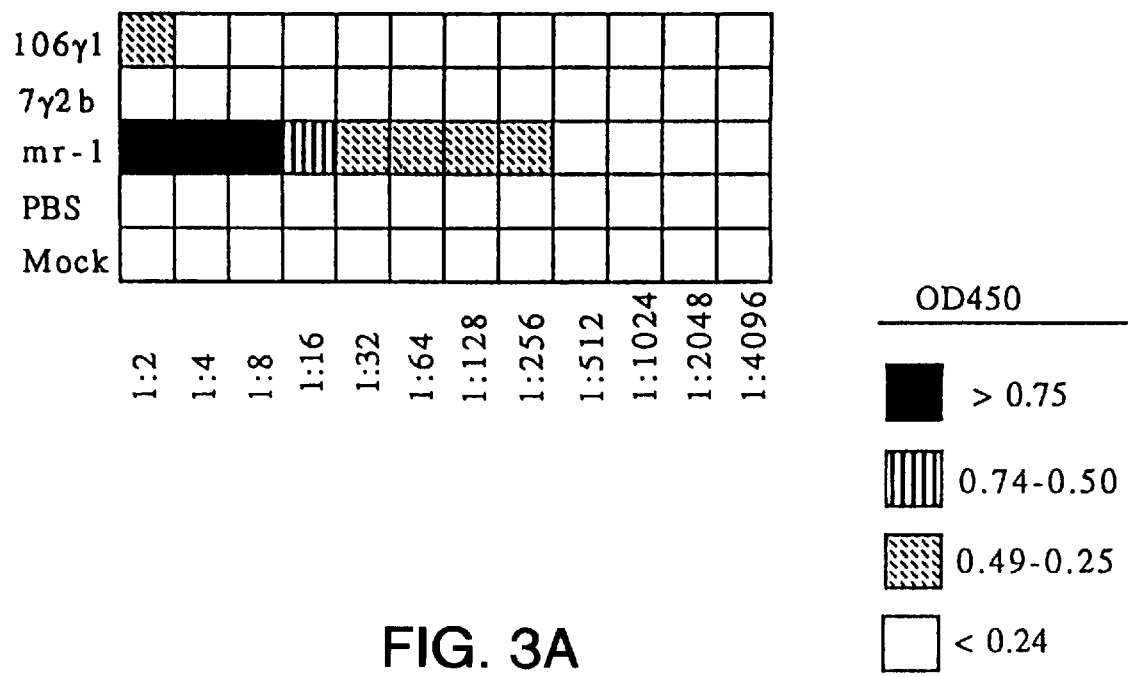
FIGS. 3A and B demonstrate a titration of 106 sFv-Ig and 7 sFv-Ig COS cell transfection supernatants binding to immobilized human gp39. Flat bottom 96-well plates coated with anti-mouse Lyt-2a and Lyt-2a-gp39 fusion protein were used to screen COS cell supernatants for functional anti-gp39 106 and 7 sFv-Ig. Two-fold dilutions of a representative clone for each sFv-Ig are shown. While mock transfection supernatant (no DNA added to COS cells) showed no activity, 106 sFv-Ig and 7 sFv-Ig bound to immobilized gp39 at dilutions in excess of 1:100 (for 106 sFv-Ig, binding could be detected down to a 1:1000 dilution of transfection supernatant). In comparison, an anti-mouse gp39 sFv (mr1 sFv-Ig) did not bind to human gp39 although it bound well to plates coated with anti-mouse Lyt-2a and Lyt 2a-murine gp39 fusion protein. 106 sFv-Ig and 7 sFv-Ig showed little to no reactivity on plates coated with anti-mouse Lyt-2a and Lyt 2a-murine gp39 fusion protein.

In order that the invention herein described may be more fully understood, the following description is set forth.

The present invention is directed to a group of monoclonal antibodies which recognize specific epitopes of the T cell membrane glycoprotein gp39, and to the hybridomas which produce and secrete these monoclonal antibodies. Also encompassed by the present invention are other monoclonal antibodies which can be made which competitively inhibit the binding of the specifically disclosed monoclonal antibodies to their epitopes. Fragments of the monoclonal antibodies and recombinant proteins having the variable region of the disclosed monoclonal antibodies are also included in the present invention, as are methods of using the monoclonal antibodies, fragments and recombinant binding proteins in diagnosing hyper IgM syndrome, in other cell adhesion and T cell assays, and in methods of modulating immune responses in a host.

The preparation of monoclonal antibodies can be accomplished by immortalizing a cell line producing antibody specific for an epitope on gp39. Typically, a monoclonal antibody of the present invention can be produced using well established hybridoma techniques first introduced by Kohler and Milstein. See, Kohler and Milstein, 1975, *Nature* 256:495. See also, Brown et al. 1981, *J. Immunol.* 127:539; Yeh et al. 1979, *Proc. Nat'l. Acad. Sci. USA* 76:297; Hellstrom et al. 1990, *Cancer Research* 50:2183.

These techniques involve the injection of an immunogen (e.g., cells or cellular extracts containing the gp39 antigen or purified gp39, either as native protein, a fragment containing an epitopic site, or a fusion protein) into an animal so as to elicit a desired immune response in that animal. Animals commonly used include many mammals, e.g., mouse, rat, cow, goat, sheep, rabbit, etc. The immunogen is commonly presented to the animal with an adjuvant, e.g., complete Freund's adjuvent, aluminum hydroxide gel, or the like. The animal may then be bled and the blood employed for the isolation of polyclonal antibodies. Alternatively, the peripheral blood lymphocytes, splenic lymphocytes (B-cells), or lymph node lymphocytes can be employed for fusion with an appropriate myeloma cell to immortalize the genes encoding monoclonal antibodies specific for gp39.

In the present invention, the monoclonal antibodies are partially characterized by their binding to a series of gp39 mutants. The binding avidity (strength of binding) of the antibodies to the mutant gp39 was compared to the binding avidity of the antibody to wild-type gp39. Binding avidity was characterized as poor if the comparison of the binding avidity to a particular mutant was less than 25–30% of the binding avidity to wild-type gp39; a weak or less profound reduction in reactivity was obtained if the binding avidity to a mutant was 25 to 30% to 50–55% of the binding avidity to wild-type gp39; a somewhat reduced reactivity was obtained if the binding avidity to the mutant was 50–55% to 75–80% of the binding avidity to wild-type; and similar or equivalent reactivity was obtained if the binding avidity to a mutant was 75–80% or greater than the binding avidity to a wild-type gp39. The antibodies of the present invention were also characterized by their isotype, binding to gp39 by Western blot, ability to suppress B-cell proliferation and ability to suppress immunoglobulin production.

While the invention is described by way of examples using murine monoclonal antibodies, the invention is not so limited and encompasses the use of, for example, human hybridomas (Cote et al. 1983, *Proc. Nat'l. Acad. Sci. USA* 80:2026) or by transforming human B cells (e.g., with Epstein Barr Virus (EBV) in vitro) (Cole et al. 1985, in *Monoclonal Antibodies and Cancer Therapy*, Alan R. Liss, pp. 77–96).

The monoclonal antibodies can be of any of the classes or subclasses of immunoglobulins, such as IgM, IgD, IgA, IgE or subclasses of IgG known for each species of animal. Generally, the monoclonal antibodies can be used intact, or as epitope binding fragments, such as Fv, Fab, or F(ab')$_2$.

The cell lines of the present invention can find use other than for the direct production of the monoclonal antibodies. The cell lines can be fused with other cells (such as suitably drug-marked human myeloma, mouse myeloma, or human lymphoblastoid cells), to produce hybridomas, and thus provide for the transfer of genes encoding the monoclonal antibodies. Alternatively, the cell lines can be used as a source of the chromosomes, or genes, encoding the immunoglobulins, particularly those regions of the genes encoding the variable or epitope binding regions of the immunoglobulin, which can be isolated and transferred to cells by techniques other than fusion. This can particularly be accomplished by preparing cDNA libraries (from mRNA), coding for the immunoglobulin and free of introns, then isolating and placing the DNA into suitable prokaryotic or eukaryotic expression vectors. Methods for the expression vectors can then be used to transform a host for production of immunoglobulin or epitope binding fragments. See, generally, U.S. Pat. Nos. 4,172,124; 4,350,683; 4,363,799; 4,381,292; and 4,423,147. See also, Kennet et al. 1980, *Monoclonal Antibodies*, Plenum Press, New York, and references cited therein.

More specifically, in accordance with hybrid DNA technology, the immunoglobulin or epitope binding fragments of the present invention can be produced in bacteria (See, Boss et al. 1984, *Nucl. Acid Res.* 12:3791 and Wood et al. 1985, *Nature* 314:446). For example, the messenger RNA transcribed from the genes coding for the light and heavy chains of the monoclonal antibodies produced by a cell line of the present invention can be isolated by differential cDNA hybridization employing degenerate cDNA probes derived from DNA sequences known to be common to mature immunoglobulin molecules of the parental cell type. The mRNA that does not hybridize will be rich for the messages coding for the desired immunoglobulin chains. As necessary, this process can be repeated to further enhance the desired mRNA levels. The subtracted mRNA composition can then be reverse-transcribed to provide for a cDNA mixture enriched for the desired sequences. The RNA may be hydrolyzed with an appropriate RNase and the ssDNA made double-stranded with DNA polymerase I and random primers, e.g., randomly fragmented calf thymus DNA. The resulting dsDNA can then be cloned by insertion into an appropriate vector, e.g., virus vectors, such as lambda vectors or plasmid vectors (such as pBR322, pACYC 184, etc.). By developing probes based on known sequences for the constant regions of the light and heavy chains, those cDNA clones having the gene coding for the desired light and heavy chains can be identified by hybridization. Thereafter, the genes can be excised from the plasmids, manipulated to remove superfluous DNA, and then introduced in an appropriate vector for transformation of a host and ultimate expression of the gene. Other methods well known in the art can be used to isolate gene sequences which encode immunoglobulin molecules.

In the present application, RNA was isolated and cDNA was generated using PCR techniques with immunoglobulin constant regions as primers. The PCR amplified VH and VL fragments were selected, cloned, and used to determine the nucleotide sequences for the variable regions.

Conveniently, mammalian hosts (e.g., mouse cells) can be employed to process the immunoglobulin chains (e.g., join the heavy and light chains) to produce an intact immunoglobulin; and furthermore, secrete the immunoglobulin free of any leader sequences, if desired. Alternatively, one can use unicellular microorganisms for producing the two chains, where further manipulation may be required to remove the DNA sequences coding for the secretory leader and processing signals, while providing for an initiation codon at the 5' terminus of the sequence coding for the heavy chain. In this manner, the immunoglobulins can be prepared and processed so as to be assembled and glycosylated in cells other than mammalian cells.

If desired, each of the chains may be truncated so as to retain at least the variable region, which can then be manipulated to provide for other recombinant binding proteins specific for the gp39 epitope recognized by the parental antibody.

One such recombinant binding protein is a chimeric antibody, in which the variable regions of a parental antibody are recombined with the constant regions of antibodies derived from a different species (e.g., murine variable regions recombined with human constant regions). Typically, the variable region of a monoclonal antibody of the present invention will be joined with the constant region of a human antibody. Chimeric antibodies which are largely human in composition are substantially less immunogenic than murine antibodies.

Another recombinant epitope binding protein is the single chain antibody. In such a construct, sometimes called an sFv, one variable region from both the heavy chain and light chain of the parental antibody are covalently linked through a peptide linker such that the epitope binding region is reformed. Multivalent single chain antibodies comprising heavy and light chain variable regions specific for one or more epitopes of gp39 can also be constructed. See EP 0 610,046 and WO 94/13806 for how such recombinant binding proteins can be constructed.

Still another type of recombinant binding protein is the humanized antibody wherein codons within the framework region of a nonhuman monoclonal antibody are changed through various methods of point mutagenesis to encode amino acid residues to make the murine framework more resemble a human framework region. See EP 0 578,515, EP 0 592,106, Jones et al. 1986, Nature 321:522; Riechmann et al. 1988, Nature 332:323. Changes can also be made to the complementarity determining regions (CDR) to make the entire variable region more resemble the surface character of a human antibody. The intention of making the various recombinant binding proteins is to alter either the immunogenicity of the antibody or an accessory activity related to the constant region or other active moiety recombined with the epitope binding region and to retain the gp39 epitope binding specificity of the original parental antibody.

This invention further provides compositions of the monoclonal antibodies and recombinant binding proteins of the present invention. These compositions can comprise the monoclonal antibodies and recombinant binding proteins of the present invention labeled with a detectable marker, for example, a radioactive isotope, enzyme, fluorophor, chromophore, etc. Other compositions can comprise the monoclonal antibodies or recombinant binding proteins of the present invention conjugated or linked to a therapeutic agent, such as a radioisotope, a toxin (i.e., *Pseudomonas exotoxin*), or a chemotherapeutic agent.

Conjugation or linkage of the antibody or recombinant binding protein of the present invention to the detectable marker or therapeutic agent can be by covalent or other chemical binding means. The chemical binding means can include, for example, glutaraldehyde, heterobifunctional, and homobifunctional linking agents. Heterobifunctional linking agents can include, for example, SMPT (succinimidyl oxycarbonyl-α-methyl-α(2-pyridyldition)-tolume, SPDP (N-succinimidyl3-(2-pyridylilithio) propionate and SMCC (succinimidyl-4-(N-male-imidomethyl) cyclohexane-1-carboxylate. Homobifunctional linking agents can include, for example, DMP (dimethyl pimelimidate), DMA (dimethyl suberinidate) and DTBP dimethyl 3,3'-dithio-bispropionimidate.

Certain protein detectable markers and therapeutic agents can be recombinantly combined with the variable regions of the monoclonal antibodies of the present invention to construct compositions which are fusion proteins, wherein the monoclonal antibody variable regions maintain their binding specificity and the detectable marker or therapeutic agent retain their activity. Recombinant methods to construct these fusion proteins are well known in the art.

Pharmaceutical compositions comprising monoclonal antibody or recombinant binding proteins, either conjugated or unconjugated, are encompassed by the present invention. A pharmaceutical composition can comprise the monoclonal antibody and a pharmaceutically acceptable carrier. For the purposes of the present invention, a "pharmaceutically acceptable carrier" can be any of the standard carriers well known in the art. For example, suitable carriers can include phosphate buffered saline solutions, emulsions such as oil/water emulsions, and various types of wetting agents. Other carriers can also include sterile solutions, tablets, coated tablets, and capsules.

Typically, such carriers can contain excipients such as starch, milk, sugar, types of clay, gelatin, steric acid, or salts thereof, magnesium or calcium sterate, talc, vegetable fats or oils, gums, glycerols, or other known excipients. Such carriers can also include flavors and color additives, preservatives, or other ingredients. Compositions comprising such carriers are formulated by well known conventional means. See Remington's Pharmaceutical Science, 15th Ed., Much Publishing Company, Easton, Pa. (1980).

The monoclonal antibodies and recombinant binding proteins of the present inventions find many in vitro and in vivo uses. For example, compositions of the present invention can find use in vitro to isolate soluble human gp39 and proteins having mutations in human gp39 associated with the human disease, such as X-linked hyper IgM syndrome. The compositions can also find use in diagnostic methods for differentiating between hyper X-linked IgM and CVI.

For diagnostic purposes, the monoclonal antibodies and recombinant binding proteins can be either labeled or unlabeled. Typically, diagnostic assays entail detecting the formation of a complex through the binding of the monoclonal antibody or recombinant binding protein to the human gp39 either at the cell surface or within the activated T cell. When unlabeled, the antibodies and recombinant binding proteins find use in agglutination assays. In addition, unlabeled antibodies can be used in combination with other labeled antibodies (second antibodies) that are specifically reactive with the monoclonal antibody or recombinant binding protein, such as antibodies specific for immunoglobulin. Alternatively, the monoclonal antibodies and recombinant binding proteins can be directly labeled. A wide variety of labels can be employed, such as radionuclides, fluorescers, enzymes, enzyme substrates, enzyme cofactors, enzyme inhibitors, ligands (particularly haptens), etc. Numerous types of immunoassays are well known in the art.

Commonly, the monoclonal antibodies and recombinant binding proteins of the present invention are used in fluorescent assays, where the subject antibodies or recombinant binding proteins are conjugated to a fluorescent molecule, such as fluorescein isothiocyanate (FITC). Because many mutant forms of human gp39 are not transported to the cell surface, T cells are isolated from a subject, activated and then the cells are permeabilized to allow the labeled antibody or recombinant binding protein to penetrate the cell and bind to mutant gp39 wherever it is present in the cell. Binding of the monoclonal antibodies to the intracellular gp39 and an inability to bind a soluble form of CD40 at the cell surface demonstrates the presence of certain point mutations in human gp39 has prevented localization of the gp39 molecule to the cell surface. This can be associated with human disease, such as X-linked hyper IgM. Presence of the bound antibody can be detected by a fluorescence activated cell sorter after excess labeled antibody or binding protein is washed away. Other conventional techniques well known to those skilled in the art can also be utilized.

Kits can also be supplied for use with the compositions of the subject antibodies and recombinant binding proteins for detecting the presence of mutant human gp39 molecules in solution or on activated T cells. Thus, the subject monoclonal antibody and recombinant binding protein compositions of the present invention may be provided, usually in a lyophilized form either individually or in combination with antibodies which bind other specific human gp39 mutants. The antibodies and recombinant binding proteins, which may be conjugated to a label or unconjugated, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient can be present in from about 1 to 99% wt. of the total composition. Where a second antibody capable of binding to the monoclonal antibody or recombinant binding protein is employed, this will usually be present in a separate vial. The second antibody is typically conjugated to a label and formulated in an analogous manner with the formulations discussed above.

The monoclonal antibodies, particularly the recombinant binding proteins, single chain antibodies, chimeric antibodies and humanized antibodies, of this invention can also be incorporated as components of pharmaceutical compositions containing an amount of binding protein which is effective, for example, to modulate an immune response (i.e., an autoimmune response or allergic reaction) with a pharmaceutically acceptable carrier. Pharmaceutically accepted adjuvants (buffering agents, dispensing agents) may also be incorporated into the pharmaceutical composition. Such compositions can contain a single monoclonal antibody or recombinant binding protein specific for human gp39. Alternatively, a pharmaceutical composition can contain other biologically active molecules, for example, lymphokines, cytokines, other monoclonal antibodies or fusion proteins (i.e., CD28-Ig, CTLA4-Ig).

The monoclonal antibodies, recombinant binding proteins and pharmaceutical compositions thereof of this invention are particularly useful for oral or parenteral administration. Preferably, the pharmaceutical compositions can be administered parenterally, i.e., subcutaneously, intramuscularly or intravenously. Thus, this invention provides compositions for parenteral administration which comprise a solution of the monoclonal antibody or recombinant binding protein dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents, and the like, for example, sodium acetate, sodium chloride, potassium chloride, calcium chloride, sodium lactate, etc. The concentration of antibody or recombinant binding protein in these formulations can vary widely, i.e., from less than about 0.5%, usually at or at least about 1% to as much as 15 or 20% by weight and will be selected primarily based on fluid volumes, viscosities, etc., preferably for the particular mode of administration selected.

Thus, a typical pharmaceutical composition for intramuscular injection could be made up to contain 1 ml sterile buffered water, and about 50 mg of monoclonal antibody. A typical composition for intravenous infusion could be made up to contain, for example, 250 ml of sterile Ringer's solution, and 150 mg of monoclonal antibody or recombinant binding protein. Actual methods for preparing parenterally administerable compositions will be known or apparent to those skilled in the art and are described in more detail in, for example, Remington's Pharmaceutical Science, 15th Ed., Mech Publishing Company, Easton, Pa. (1980), which is incorporated herein by reference.

The monoclonal antibodies and recombinant binding proteins of this invention can be lyophilized for storage and reconstituted in a suitable carrier prior to use. It will be appreciated by those skilled in the art that lyophilization and reconstitution can lead to varying degrees of antibody activity loss and that use levels may have to be adjusted to compensate.

The pharmaceutical compositions of the present invention find use in vivo to inhibit the CD40/gp39 interaction. Blocking this interaction limits both primary and secondary antibody responses to T-cell dependent antigens and antibody production specific for these antigens. Therefore, the monoclonal antibodies, antigen binding fragments, and recombinant binding proteins can be used to inhibit the activation of B cells, modulating or inhibiting autoimmune disease (i.e., psoriasis, rheumatoid arthritis, systemic lupus erythematosis, diabetes mellitus, etc.), allergic responses, organ rejection or graft-versus-host disease. The compositions can also be used for imaging tumors which express gp39, when labeled with a detectable marker. When conjugated with a therapeutic agent or as a fusion protein with a therapeutic agent, the monoclonal antibodies, antigen binding fragment or recombinant binding proteins, can also be used o target the therapeutic agent to tumor cells.

The pharmaceutical compositions of the present invention find use in vivo to inhibit the CD40/gp39 interaction. Blocking this interaction limits both primary and secondary antibody responses to T-cell dependent antigens and antibody production specific for these antigens.

This invention is illustrated in the Examples which follow. This Example section is provided to aid in understanding the invention but is not intended to, and should not be construed to, limit in any way the invention as set forth in the claims which follow.

EXAMPLE 1

Generation and Initial Characterization of Monoclonal Antibodies Specific for gp39-Fusion 1

A. Immunization

A six-to-eight-week-old female BALB/c mouse was initially immunized intraperitoneally with 30 μg of a gp39-CD8 fusion protein (Hollenbaugh et al. 1992, *EMBO J.* 11:4313–4321) in a volume of 100 μl of complete Freund's adjuvant. Approximately two weeks later, the mouse was similarly injected except the vehicle used was incomplete Freund's adjuvant. Three weeks later the mouse received an intravenous pre-fusion booster injection with 23 μg of gp39 fusion protein in a volume of 100 μl of phosphate buffered saline (PBS).

B. Fusion

Three days after the pre-fusion booster, the spleen and lymph nodes (axillary, popliteal, inguinal, and mesenteric) were harvested. These were cut into small pieces with a scalpel and then gently pressed between the frosted glass ends of glass microscope slides in the presence of incomplete Iscove's medium (Iscove's modified Dulbecco's medium supplemented with penicillin and streptomycin to a final concentration of 100 U/ml and 100 μg/ml, respectively) to loosen lymphocytes from connective tissue. The suspension was gently pipetted to further loosen cells from each other and then the suspension was passed through a cell strainer (Falcon 2350) to remove clumps of connective tissue debris. The cell suspension was washed twice by centrifugation at 200 g for 10 minutes followed by resuspension of the cell pellet in incomplete Iscove's medium. After washing, a viable total leukocyte count was determined by trypan blue exclusion.

The fusion procedure was based on the methods of Lane et al. 1986 (*Methods Enzymol.* 121:183–192). Myeloma cells (X63-Ag8.653, Kearney et al. 1979, *J. Immunol.* 123:1548–1550) in log phase growth were washed twice by centrifugation at 200 g for 5 min. followed by resuspension of the cell pellet in incomplete Iscove's medium. The cells were then combined with the washed leukocytes in a 50 ml plastic centrifuge tube at a 1:4 ratio of myeloma cells to leukocytes and centrifuged at 200 g for 10 minutes. Following aspiration of the medium, the tube was gently tapped until the cell pellet became resuspended in the remaining small amount of medium. After incubation of the tube in a 37° C. water bath for 1 min., 1.5 ml of freshly prepared 37° C. polyethylene glycol-dimethyl sulfoxide solution [50% (w/v) Kodak 1450 polyethylene glycol, 5% (v/v) dimethyl sulfoxide, and 45% (v/v) phosphate buffered saline containing no calcium or magnesium, pH 8.0] was added to the cells over a 45 second period with constant swirling of the tube in a 37° C. water bath. The fusion mixture was then diluted with 50 ml of 37° C. complete Iscove's medium ((incomplete Iscove's medium supplemented with an extra 2 mM L-glutamine and 15% (v/v) fetal calf serum (FCS)) over a 90 second period as follows: 3 ml over the first 30 seconds, 9 ml over the next 30 seconds, and the remainder over the last 30 seconds. The tube was incubated at 37° C. for 10 minutes after which it was centrifuged at 200 g for 5 minutes, the supernatant aspirated, and the cells resuspended in 120 ml of hybridoma medium [complete Iscove's medium supplemented with hypoxanthine ($1 \times 10^{-4}$M final concentration), aminopterin ($4 \times 10^{-7}$M final concentration), thymidine ($1.6 \times 10^{-7}$M final concentration), and 10% (v/v) hybridoma cloning factor (Boehringer Mannheim)]. The cell suspension was plated into six 96-well cell culture plates (200 μl/well) resulting in a plating density of 243,000 total cells (pre-fusion) per well. Wells were fed on days 3 and 5 post fusion by replacement of half the supernatant with fresh hybridoma medium and assayed for anti-gp39 specific antibody on day 8.

C. Screening

Supernatants from cell culture wells having growing cells were initially screened for reactivity with the gp39-CD8 fusion protein immunogen as follows. Dynatech Immulon 2 EIA plates were coated with 1 μg/ml (100 μl/well) of antibody 53-6 (rat anti-mouse CD8, ATCC TIB 105) in 0.05M sodium carbonate/sodium bicarbonate buffer, pH 9.6. The plates were sealed and incubated overnight at 4° C. All subsequent steps were performed at room temperature. Coating agent was removed and wells blocked with blocking reagent [(specimen diluent (Genetic Systems Corp., Seattle, Wash.) diluted 1:10 in deionized water)] for one hour. Blocking reagent was removed and COS cell supernatant containing gp39-CD8 fusion protein, diluted 1:4 in complete Iscove's medium containing 2% FCS (2% FCS-Iscove's) was added (100 μl/well) and incubated for one hour. Fusion protein was removed and the wells were washed once with 200 μl of PBS-Tween (PBS containing 0.05% (v/v) Tween 20). Cell culture supernatant was then added (50 μl/well) and incubated for one hour. The cell culture supernatant was removed and the wells washed once with PBS-Tween prior to the addition of horseradish peroxidase (HRP) labeled goat anti-mouse IgG (Jackson Immunological Laboratories) diluted 1:100,000 in blocking reagent followed by one hour incubation. Excess labeled antibody was removed and the wells were washed three times with PBS-Tween. This was followed by the addition of 100 μl/well tetramethylbenzidine (Genetic Systems Corp.) diluted 1:100 in 0.1M citrate buffer, pH 5.5, containing 0.015% of a 30% $H_2O_2$ solution. Plates were incubated for 15 minutes and the reaction stopped by the addition of 3N sulfuric acid (50 μl/well). Optical density was measured at 450/630 nm on a Bio-Tek Instruments EL312 Microplate Reader.

Those cell culture supernatants found to be positive for binding to gp39-CD8 fusion protein were then tested for binding to CD72-CD8 fusion protein to assess for antibodies specific for gp3 9 rather than the CD8 portion of the fusion protein. Description of the construction of the chimeric gene encoding CD72-CD8 fusion protein and expression of the fusion protein transiently in COS cells are described in Hollenbaugh et al., 1992 (incorporated by reference herein in its entirety). The ELISA assay for binding to CD72-CD8 fusion protein was identical to that described above for gp39-CD8 except that undiluted COS cell supernatant containing CD72-CD8 fusion protein was used in place of gp39-CD8 fusion protein.

All supernatants that were reactive with the gp39-CD8 fusion and not with CD72-CD8 fusion protein were then tested for their ability to inhibit the binding of CD40-Ig fusion protein to gp39-CD8 fusion protein. Briefly, Dynatech Immulon 2 EIA plates were coated with antibody 53-6 as described above. The wells were blocked and washed as above and COS cell supernatant containing gp39-CD8 fusion protein diluted 1:4 in 2% FCS-Iscove's was added (100 μl/well) and incubated for 1 hour. The gp39 fusion protein was removed and the plates were washed with 200 μl of PBS-Tween. Culture supernatants were then added (50 μl/well) and incubated for 1 hour, removed and the wells washed once with PBS-Tween. Purified CD40-Ig fusion protein (EP 555880) was then diluted to 2 μg/ml in 2% FCS-Iscove's, added to all wells (50 μl/well) and the plates incubated for one hour. Excess fusion protein was removed and the wells were again washed once with PBS-Tween prior to adding HRP labeled goat anti-human IgG (Jackson Immunological Laboratories) diluted 1:10,000 in blocking reagent (50 μl/well). After a one-hour incubation at room temperature, HRP labeled reagent was removed and the plates washed three times with PBS-Tween. Disclosure of bound HRP labeled reagent and measurement of resulting optical density was as described in ELISA assays described above.

D. Cloning

A number of wells were found which contained antibody specific for gp39 and which inhibited the interaction of gp39 with its ligand CD40 in an ELISA. The cells growing in these wells were then cloned and subjected to additional screening criteria.

Cloning was initiated with a "mini-cloning" procedure in which cells from designated master wells were first plated at a density of 10 or 20 cells per well in 96-well flat-bottom cell culture plates. One or two plates were established for each master well in a culture medium of complete Iscove's medium supplemented with 10% (v/v) hybridoma cloning factor (cloning medium) at a volume of 200 μl/well. Cells were cultured for 7 to 8 days at which time supernatants were again tested for gp39 reactivity and ability to inhibit the binding of CD40-Ig to gp39-CD8 fusion protein by ELISA (described above). From the wells in each miniclone set that satisfied these criteria, one well was cloned. Cells were removed from the selected well and diluted to a concentration in cloning medium that would provide a calculated density of one cell for every two wells. The cells were plated in two half-area 96-well cell culture plates (Costar 3696) in a volume of 100 or 150 μl/well.

After four or five days of culture, the wells were examined on an inverted microscope and those wells containing a single clone were marked. After a further three-four days of culture, supernatants from all wells were tested for gp39 reactivity (gp39-CD8 fusion protein ELISA, described above) and ability to inhibit the binding of CD40-Ig to gp39-CD8 by ELISA (described above). Supernatants from wells that were reactive with gp39-CD8, blocked the interaction of CD40-Ig with gp39-CD8, and came from wells marked as containing single clones were further examined for their ability to bind to a Jurkat T cell line that constitutively expressed gp39 on its surface (BMS-10, R. Mittler, Bristol-Myers Squibb) and to block the binding of CD40-Ig fusion protein to these cells. Clones that satisfied the latter two criteria were selected for further study.

Binding of antibody to BMS-10 cells was determined by fluorescent cell analysis. Briefly, 250,000 BMS-10 cells were counted, added to each tube, and centrifuged at 250 g for 5 minutes. Culture medium was aspirated and 100 μl of each supernatant containing antibody reactive with gp39-CD8 by ELISA was added to a tube. Controls included culture medium only or culture medium containing a negative control mouse monoclonal antibody. The mixture was incubated on ice for 30 minutes and then 2 ml of 2% FCS-Iscove's was added. The tubes were centrifuged at 250 g for 5 minutes and the supernatant was removed. FITC labeled F(ab')$_2$ goat anti-mouse IgG F(ab')$_2$ (Jackson Immunological Laboratories)) was diluted 1:500 in 2% FCS-Iscove's and 100 μl added to each tube. After a 30 minute incubation on ice, cells were washed twice with 1 ml of 2% FCS-Iscove's and resuspended in 250 μl of 2% FCS-Iscove's prior to analysis on a Becton Dickinson FACScan™.

Assessment of an antibody's ability to block the binding of CD40-Ig to BMS-10 cells used the above procedure except that after washout of unbound anti-gp39 antibody, CD40-Ig, diluted to 20 μg/ml in 10% FCS-Iscove's, was added to each tube, 100 μl/tube. After a 30 minute incubation on ice, 2 mls of 2% FCS-Iscove's was added to each tube, the tubes centrifuged for five minutes at 250 g, and the supernatants aspirated to remove unbound CD40-Ig. Instead of an FITC-labeled anti-mouse Ig reagent, an appropriately diluted PE- or FITC-labeled F(ab')$_2$ goat anti-human IgG (Jackson Immunological Laboratories, #109-116-098 or #109-016-098) was then added to each tube to detect bound CD40-Ig. Otherwise, the assay was completed and the cell analyzed as described above.

Following the procedures outlined above, a total of 23 mouse anti-human gp39 monoclonal antibodies were derived. Each of the monoclonal antibodies was isotyped to identify its IgG subclass and their ability to recognize gp39 was further characterized. An analysis of epitope specificity differences between the monoclonal antibodies was also carried out, as was the ability of the antibodies to inhibit T cell dependent B cell proliferation and immunoglobulin production.

EXAMPLE 2

Generation and Initial Characterization of Monoclonal Antibodies Specific for gp39-Fusion 7

A. Immunization

A six-to-eight-week-old female BALB/c mouse was initially immunized subcutaneously at four sites with a total of 30 μg of a gp39-CD8 fusion protein in complete Freund's adjuvant. Approximately two and five weeks later, this mouse was similarly injected with 30 μg and 25 μg, respectively, of gp39-CD8 except that the vehicle for antigen was incomplete Freund's adjuvant. Five months after initial immunization) this mouse was injected IP with 10 μg of fusion protein in incomplete Freund's adjuvant. Two weeks later, the mouse received an IV pre-fusion booster injection of 30 μg of gp39-CD8 fusion protein in PBS.

B. Fusion and Screening

Three days later, harvest, preparation, and fusion of the mouse spleen and lymph node cells to mouse myeloma cells was performed as for fusion 39-1 except that only 1 ml of PEG was used to fuse cells. The cell suspension resulting from this fusion was seeded into 10 96-well cell culture plates at a plating density of 183,000 total cells (pre-fusion)

per well. Wells were fed on days 3 and 6 post fusion by replacement of half the supernatant with fresh hybridoma medium and assayed for anti-gp39 specific antibody on day 9.

Supernatants were initially screened for anti-gp39 specificity in an ELISA based cell binding assay. Falcon (#3072) or Costar (#3596) 96-well flat bottom plates were coated with 3.5 $\mu$g/cm$^2$ of Cell-Tak (Collaborative Biomedical Products #40240) diluted in 0.1M sodium bicarbonate, pH 8.0. Plates were incubated at room temperature for 30 minutes. Unbound Cell-Tak was aspirated and the wells washed twice with 150 $\mu$l/well of glass distilled water. BMS-10 cells were centrifuged and resuspended to a concentration of 2×10$^6$ cells/ml in serum-free Iscove's medium. Fifty $\mu$l of this cell suspension was added to each well and the plates centrifuged for 5 minutes at 250 g. Plates were then incubated at room temperature for 30 minutes after which the medium was aspirated from the wells using an eight channel manifold (Drummond #3-00-093). Culture supernatants were then replica plated onto the assay plates, 50 $\mu$l/well, and the plates incubated for 1 hour. Supernatants were aspirated and the plates washed once with 150 $\mu$l/well of PBS containing 1% FCS. HRP labeled rat anti-mouse IgG (Zymed #04-6020) diluted in PBS containing 5% FCS was added, 50 $\mu$l/well. After a one-hour incubation at room temperature, HRP labeled reagent was removed and the plates washed three times with PBS-Tween. Disclosure of bound HRP labeled reagent and the measurement of resulting optical density was as described in other ELISA assays detailed above.

As a secondary screen, supernatants from positive wells in the BMS-10 cell ELISA above were assayed for reactivity to gp39-CD8 and CD72-CD8 fusion proteins using the respective fusion protein ELISAs described earlier. In this assay, HRP labeled rat anti-mouse IgG (Zymed #04-6020) replaced the goat anti-mouse IgG used in earlier described assay. Confirmation of specific reactivity with gp39 positive BMS-10 cells was then performed using indirect immunofluorescence and FACS analysis as described earlier. Supernatants were also tested for their ability to inhibit CD40-Ig binding to gp39-CD8 using the blocking ELISA described earlier. Supernatants were further analyzed as to their isotype using the gp39-CD8 ELISA except for one modification. Each supernatant was tested in quadruplicate and bound anti-gp39 antibody was then traced with four different HRP labeled anti-mouse isotype-specific reagents (Zymed, rat anti-mouse IgG1, IgG2a, or IgG2b, #04-6120, 04-6220, and 04-6320, respectively, and rabbit anti-mouse IgG3, #61-0420). This overall analysis identified one well that contained antibody specific for cell surface expressed gp39, blocked the binding of CD40-Ig to gp39-CD8 and was of the IgG2a isotype. Appropriate antibody producing cells from this well (39-7.3E12) were minicloned and cloned as described earlier.

EXAMPLE 3

Characterization of the anti-gp39 Monoclonal Antibodies

A. Isotyping

Each of the 23 monoclonal antibodies obtained by the above procedures was isotyped to identify its IgG subclass using an Isotype Ab-Stat Kit™ (SangStat Medical Corporation, Menlo Park, Calif.) or ISOStrip™ kit (Boehringer Mannheim) as per manufacturer's instructions. The isotypes of the monoclonal antibodies of the present invention are shown in Table 1.

B. Western Blot and Immuneprecipitation Western blot evaluation was performed by two different procedures. In one, 1.5 $\mu$g of purified soluble gp39-CD8 fusion protein in 300 $\mu$l of loading dye [250 mM Tris, 0.002% (v/v) bromphenol blue, 40% (v/v) glycerol, pH 6.8, 15 $\mu$l of 20% SDS, 10 $\mu$l of 2-mercaptoethanol] was electrophoresed on a 12% SDS-polyacrylamide gel at 150 V for 1 hour. The separated proteins were transferred to nitrocellulose paper with a Bio-Rad mini-blot transfer apparatus according to manufacturer's instructions. After transfer, the nitrocellulose was allowed to dry at room temperature and then each lane was cut from the sheet as wide vertical strips which were placed individually into the wells of a Bio-Rad shallow well unit. The strips were incubated in 10 ml of a blocking solution of Tris Buffered Saline containing 5% (w/v) non-fat dry milk (TBS-T) for 2 hours at room temperature on a flat plane rocker. After incubation, the blocking solution was aspirated and the strips were rinsed twice with TBS-T.

Anti-gp39 monoclonal antibody was diluted to a concentration of about 12 $\mu$g/ml in TBS-T and 3 ml of antibody solution was added to each strip, one antibody per strip, for 2 hours at room temperature with rocking. Excess antibody solution was aspirated from each well and the strips were washed five times with 10 ml TBS-T. After washing, 10 ml of a 1:3,000 dilution of HRP goat anti-mouse Ig (Tago) in TBS-T was added to each well. The strips were incubated for two hours at room temperature and then washed five times as described above.

Detection of bound HRP conjugated antibody was performed using ECL detection reagents (Amersham) according to manufacturer's instructions. The detection solution was aspirated and excess liquid on the strips was removed by touching the end of the strips onto a paper towel. The strips were aligned inside a plastic page protector and the protector sealed. The sealed protector was then exposed to autoradiography film for variable time periods (1 second to 15 minutes and the films subsequently processed.

In a second procedure, 200 $\mu$l of spent supernatant from COS cells transfected with gp39-CD8 was diluted with 25 $\mu$l of loading dye, heated to 100° C. for 5 minutes, cooled on ice, and electrophoresed on a 10% SDS-polyacrylamide gel. Separated protein was transferred to a Bio-Rad PVDF™ membrane using a Hoeffer semi-dry transfer apparatus according to manufacturer's instructions. After the separated proteins were transferred to the membranes, the membranes were allowed to dry at room temperature and then the procedure as described above was followed to stain the membranes.

The anti-gp39 antibodies were also tested for the ability to immunoprecipitate gp39 from either transfected COS cells or activated T cells. Briefly, COS cells were transfected with a cDNA encoding human gp39 by the DEAE-dextran procedure using ten 150 mm plates at approximately 70% confluency. The following day, the COS cells were trypsinized and replated in eight T-150 cm$^2$ flasks. Media was removed after incubating overnight and the cells were washed once with modified Eagle's medium without cysteine or methionine (Gibco Select-amine Kit) and 20 ml of fresh cysteine/methionine-free media containing 0.02 mCi/ml Tran $^{35}$S label (ICN, Costa Mesa, Calif.) were then added and the cells were incubated overnight. The following day, the media was removed and the cells were rinsed once with PBS and 2 ml of lysis buffer (50 mM Tris, 150 mM NaCl, 1% NP-40, 0.25% deoxycholate) containing 1 nM phenylmethyl sulfonylfluoride (PMSF) and 25 $\mu$g/ml aprotinin was added to each flask. The flasks were placed on ice for 10 minutes, after which the buffer was removed. Aliquots were prepared and centrifuged in a microfuge at 4° C. at maximum speed for two minutes. The supernatants were pooled and stored at −70° C. prior to immunoprecipitation.

Immunoprecipitation was carried out by thawing the transfected COS cell lysates on ice and dividing the total volume into 10 aliquots. To eight tubes, 10 μg of an anti-gp39 antibody was added, while one tube received CD40 Ig as a positive control and one received no precipitating agent as a negative control. Samples were incubated on ice for 4 hours, after which 100 μl of Protein G Sepharose FF™ (Pharmacia) was added to each tube. The tubes were incubated on ice for 1 hour with mixing every 10 to 15 minutes. Samples were pulse spun in a microfuge and the supernatant was discarded. The pellets were washed by resuspension and pelleting three times with cold lysis buffer, then once with cold PBS. Following the last wash, 30 μl of SDS loading buffer containing β-mercaptoethanol was added to each tube. Samples were heated at 95° C. for 5 minutes, pulse spun and the supernatant loaded on a 12% SDS-polyacrylamide gel. At the completion of electrophoresis, the gel was placed in 10% methanol, 10% acetic acid in water for two hours. The gel was then placed in Amplify™ fluorographic agent (Amersham) containing 10% glycerol for 15 minutes. The gel was dried on Whatman 3M paper under vacuum at 80° C. for 45 minutes and exposed to X-ray film at −70° C. for 1 to 7 days. Results of the assay are summarized in Table 1. Positive immunoprecipitations were indicated by the presence of a band at the same molecular weight as the CD40-Ig control.

Radioimmunoprecipitation of gp39 from activated human peripheral blood T cells was carried out as follows. Fresh heparized whole blood was diluted 1:1 with PBS and 40 ml was overlayed onto 10 ml of Lymphocyte Separation Media™ (Organon Teknika) as described above. The sample was centrifuged for 30 minutes at 220 g. Isolated lymphocytes were washed with PBS and resuspended in modified Eagle's medium lacking cysteine and methionine containing 10% dialyzed fetal bovine serum and 0.02 mCi/ml Tran $^{35}$S Label™ at a final cell density of $3\times10^6$ cells/ml. Cells were activated by the addition of PMA (10 ng/ml) and ionomycin (1 μg/ml) for nine hours, after which the cells were pelleted, the media removed and the cells lysed with lysis buffer containing PMSF and aprotinin. The cells were incubated with lysis buffer for 10 minutes on ice prior to transferring the sample to microfuge tubes and centrifuging for 2 minutes at 4° C. The supernatants were pooled and stored at −70° C. until further processing. The precipitation was carried out as described above for transfected COS cells and the results are summarized in Table 1.

TABLE 1

Summary of Anti-Human gp39 mAbs

| mAb | Isotype | Binding to gp39 + Jurkat Cells | Inhibit Binding of CD40-Ig to gp39 + Jurkat Cells | Western Blot sgp39-CD8 | Radio-immune Precipitation |
| --- | --- | --- | --- | --- | --- |
| 39-1.3 | IgG1 | + | + | − | +(a) |
| 39-1.7 | IgG2b | + | + | − | +(a,b) |
| 39-1.21 | IgG1 | + | + | − | ND |
| 39-1.25 | IgG1 | + | ND | − | ND |
| 39-1.26 | IgG1 | + | + | − | +(a,b) |
| 39-1.29 | IgG2a | + | + | + | +(a) |
| 39-1.37 | IgG1 | + | + | − | ND |
| 39-1.52 | IgG1 | + | + | + | ND |
| 39-1.59 | IgG1 | + | + | − | ND |
| 39-1.61 | IgG1 | + | + | + | +(b) |
| 39-1.63 | IgG1 | + | + | − | ND |
| 39-1.77 | IgG1 | + | + | + | +(a,b) |
| 39-1.93 | IgG1 | + | + | + | ND |
| 39-1.106 | IgG1 | + | + | + | +(b) |
| 39-1.109 | IgG1 | + | + | + | ND |
| 39-1.122 | IgG2b | + | + | − | ND |
| 39-1.123 | IgG1 | + | + | − | ND |
| 39-1.124 | IgG1 | + | + | + | ND |
| 39-1.128 | IgG2b | + | + | − | + |
| 39-1.132 | IgG2b | + | + | − | + |
| 39-1.134 | IgG1 | + | + | + | + |
| 39-1.138 | IgG1 | + | + | − | ND |
| 39-1.156 | IgG1 | + | + | + | ND |
| 39-7.3E12 | IgG2a | + | + | − | ND | a — radioimmune precipitated from gp39 transfected COS cells
b — radioimmune precipitated from activated human T cells
ND — not done C. Examination of Binding of Anti-Human gp39 Monoclonal Antibodies with Activated and Non-Activated Normal Human T Cells.

Reactivity of the various anti-human gp39 monoclonal antibodies with activated and non-activated normal human T cells was assessed by indirect immunoflourescence followed by FACS analysis. Human blood mononuclear cells (PBMCs) were isolated by diluting whole blood 1:1 with PBS, overlaying 25 ml onto 10 ml of Lymphocyte Separation Medium (LSM, Organon Teknika) and centrifuging for 25 minutes at 450 g. Cells at the interface were collected and washed once in PBS. T cells were isolated by incubating the PBMCs with 150-fold AET-SRBC (sheep red blood cells treated with 0.143M 2-aminoethylisothiouronium bromide (Sigma)) for 5–10 minutes on ice. E-rosette positive T cells ($E^+$-T cells) were separated from the remaining cells by underlaying with cold LSM and centrifuging at 450 g for 25 minutes. The pellet (containing rosetted T cells) was collected and the sheep red blood cells were lysed with 0.83% ammonium chloride for 5 minutes at room temperature. Resulting T cells were washed once in 2% FCS-Iscove's and incubated overnight in 10% FCS-Iscove's at $1-3\times10^6$ cells/ml in a humidified 37° C./6% $CO_2$ incubator. T cells were then activated by the addition of 10 ng/ml phorbol 12-myristate 13-acetate (PMA) (Sigma) and 1 μg/ml ionomycin (Sigma) and further incubation of the cells for 5–6 hours. A portion of the T cells did not receive PMA and ionomycin but were incubated for a further 5–6 hours and are referred to here as non-activated T cells. Indirect immunofluorescence and FACS analysis of the anti-human gp39 mAbs on these activated and non-activated T cells was performed as described earlier for FACS analysis of anti-gp39 antibodies on BMS-10 cells except that FITC labeled goat anti-mouse IgG (Becton Dickinson #34903 1) was used as the second step reagent. Additionally, a murine anti-human CD69 monoclonal antibody (Becton Dickinson, #347820) was used as a positive control for activation of the T cells. In this manner all the anti-gp39 mAbs were examined. All were found to stain activated T cells and were further shown to be completely unreactive with non-activated T cells.

EXAMPLE 4

Construction of gp39 Mutant Fusion Proteins

A. Selection of gp39 Residues Targeted for Substitution:
Residues targeted for mutagenesis on gp39 were selected on the basis of a previously derived comparative protein model of the gp39 extracellular region (Aruffo et al., 1993 Cell 72:291–300), on the basis of structure-based sequence alignments of gp39 vs TNF-β and on the basis of the reported crystallographic contacts in the TNF-β/TNFR complex structure (Banner et al., 1993 Cell 73:431–445). Computer graphics analysis of the gp39 model was carried out using Insight II™ (BIOSYM Technologies Inc., San Diego, Calif.) on a Silicon Graphics Indigo™ workstation. Sequences were initially aligned using the GCG programs (Genetics Computer Group Inc., Madison, Wisc.) and manually modified taking three-dimensional information and constraints of the TNF-β (Eck et al., 1992 J. Biol. Chem. 267:2119–2122) and the TNF-β/TNFR crystal (Banner et al., supra) structures into account.

B. Construction of gp39 Mutants

Amino acid substitutions and silent mutations for diagnostic restriction enzyme cleavage sites were introduced into cDNA fragments encoding the extracellular domain of gp39 by using an overlay extension PCR protocol (Ho et al., 1989. Gene 77:51–59). The fusion genes encoding the mutant soluble gp39 (sgp39) proteins were prepared by subcloning the PCR amplified gp39 extracellular domain mutants into a mammalian expression vector containing a cDNA fragment encoding the extracellular domain of murine CD8 (Lyt 2a) (Hollenbaugh et al., 1992. EMBO J. 11:4313–4321). The forward and reverse PCR primers used for the gp39 constructs have been previously described (Hollenbaugh et al., supra).

The PCR primers used for the gp39 mutants are:

E129/A    5'
          AATCCTCAAAATGCGGCACATGTGATCAGTGCGGCCAGCA
          GTAAAACAACA 3' SEQ ID. #1,

S131/A-T135/A 5'
          CAAAATGCGGCACATGTGATCAGTGAGGCCGCCAGTAAAA
          CAGCATCTGTGTTACAGTGGGCT 3' SEQ ID. #2,

K143/A    5'
          AGTAAAACAACATCTGTGCTGCAGTGGGCTGAAGCAGGAT
          ACTACACCATGAGC 3' SEQ ID. #3,

Y145/A    5'
          AGTAAAACAACATCTGTGCTGCAGTGGGCTGAAAAAGGAG
          CCTACACCATGAGCAACACT 3' SEQ ID. #4,

N180/A    5'
          CAAGTCACCTTCTGTTCCGCTCGGGAGGCTTCGAGTCAAG
          CTCCA 3' SEQ ID. #5, and F201/A-E202/A 5'
          AGCCTCTGCCTAAAGTCCCCCGGGAGAGCCGCGAGAATCT
          TACTCAGAGCT 3' SEQ ID. #6.

The corresponding reverse primers are the reverse compliment of the sequences listed above. Base changes that encode the alanine are shown in bold type. The diagnostic restriction sites added or deleted are underlined.

C. Production and Characterization of Wild-Type and Mutant gp39 Proteins.

Wild-type and mutant sgp39 proteins were produced from transiently transfected COS cells as described elsewhere (Hollenbaugh et al., 1992 supra; Noelle et al., 1992, Proc. Nat'l. Acad. Sci. USA 89:6550–6554). COS cells were transfected using DEAE-dextran. Forty-eight hours post transfection, culture supernatant containing soluble wild-type gp39 or soluble mutant gp39 were harvested and used in assays for monoclonal antibody binding and determination of epitope specificities on human gp39.

D. Enzyme-linked Immunoassay for Monoclonal Antibody Binding to gp39 Mutant Proteins.

Results of Western blot assays indicated that at least two different epitopes on human gp39-CD8 fusion protein were being recognized. Monoclonal antibodies 39-1.29, 39-1.52, 39-1.61, 39-1.77, 39-1.93, 39-1.106, 39-1.109, 39.1.124, 39-1.134 and 39-1.156 were found to bind gp39-CD8 on Western Blot while the remaining antibodies did not. In order to define further the epitopes recognized by the monoclonal antibodies generated each was tested for binding by ELISA to a series of gp39 mutant proteins containing single or double point mutations which replaced a native amino acid residue with alanine.

The ELISA assay used was carried out as follows. Immulon 2 EIA plates were coated with 100 μl/well of a 0.8 μg/ml solution of monoclonal antibody 53-6 (ATCC TIB 105) diluted in 0.05M sodium carbonate/sodium bicarbonate buffer, pH 9.6. The plates were sealed and incubated overnight at 4° C. Following incubation, unbound antibody was removed and the plates were blocked for 1 hour with specimen diluent (Genetic Systems Corporation) diluted 1:10 in deionized water. After removal of blocking agent, 50 μl/well of appropriately diluted (see below) COS cell supernatants containing wild-type or mutant gp39-CD8 fusion protein or a negative control CD72-CD8 fusion protein were added. After a 2 hour incubation at room temperature, fusion proteins were removed and the plates washed once with 200 μl/well of PBS-Tween. Culture supernatants containing gp39-specific antibodies were appropriately diluted (see below) in 10% FCS-Iscove's and each was added (50 μl/well) in duplicate to wells containing each of the gp39 or control fusion proteins. As a control, 50 μl/well of biotinylated rat anti-mouse CD8 (see below) was added to each of the different fusion protein containing wells in order to confirm that approximately equal amounts of each fusion protein was present in all wells. After a two hour incubation at room temperature, unbound antibodies were removed and the plates washed once with PBS-Tween. HRP labeled rat anti-mouse IgG (Zymed #04-6020) and HRP labeled streptavidin (Vector Laboratories #SA5004) were appropriately diluted in blocking reagent and 50 μl/well added to wells having previously received anti-gp39 antibody and anti-mouse CD8, respectively. After a one-hour incubation at room temperature, HRP labeled reagents were removed and the plates washed three times with PBS-Tween. Disclosure of bound HRP labeled reagents and the measurement of resulting optical density was as described in other ELISA assays detailed above.

Two important parameters of the above assay were to demonstrate that similar amounts of each of the different fusion proteins were used on (i.e., bound to) the assay plates and that non-saturating concentrations of anti-gp39 antibodies were used such that optical density readings fell within the linear part of the response curve. To normalize the amount of fusion protein in all wells, serial dilutions of each fusion protein containing COS cell supernatant were evaluated in the assay described above and a dilution of each was chosen for final assays which yielded an optical density value in the linear portion of the response curve (usually between 0.3 and 0.9 absorbance units) that was within ±10% of that seen on wild-type gp39-CD8 when traced with biotinylated rat anti-mouse CD8 followed by HRP labeled streptavidin. The optimal dilution of each of the antibody containing supernatants to be used in final assays was determined by evaluating serial dilutions of each supernatant on wild-type gp39-CD8 fusion protein in the ELISA described above. Optimal dilution was defined as that for which a subsequent two-fold dilution yielded a decrease in resulting optical density value. The optimal dilution as well as two serial two-fold dilutions of it were evaluated in final assays on each of the fusion proteins as described above.

Reactivity of each of the anti-gp39 mAbs on the six mutant gp39-CD8 fusion proteins is shown in Table 2. Values depict the binding intensity on each mutant relative to that observed on wild-type (expressed as a percent) and represent the average of duplicate determinations +the standard error of the mean (SEM). Only data from those assays in which the amounts of the different fusion proteins on the assay plates were indeed similar (as shown by anti-CD8 tracing) and which were achieved with a non-saturating concentration of anti-gp39 mAb (usually a two-fold dilution of the optimal dilution as defined above) are shown.

Based on an overall similarity of binding profile on each of the gp39 mutants combined with Western blot results, the 24 anti-gp39 mAbs have been divided into eight groups. Each group is characterized by a unique binding pattern which suggests that the recognized epitope in each group of antibodies is different. Group 1, comprising mAbs 39-1.3, 39-1.21, 39-1.25, 39-1.63, 39-1.122, 39-1.123, and 39-1.138, have a notable defect in the recognition of mutants E129/A and S131/A-T135/A. These mAbs also demonstrate a somewhat less profound binding deficiency on mutant K143/A. Reactivity of these mAbs with mutants Y145/A, N180/A, and F201/A-E202/A is similar to wild-type gp39.

Group 2 is represented by a single mAb, 39-1.59. This antibody is similar to those in group 1 with regard to strongly reduced binding to mutants E129/A, S 131/A-T 135/A, and K143/A but differs in that it also showed somewhat weaker binding on mutants Y145/A, N180/A, and F201/A-E202A. Antibodies in group 3 (39-1.37 and 39-1.132) and group 4 (39-1.124 and 39-1.156) are quite similar to each other in that they recognized the E129/A mutant quite poorly and showed a profound binding deficiency on mutant K143/A. Reactivity of these mAbs with the other mutants was either slightly weaker or equivalent to that observed with wild-type gp39. Groups 3 and 4 are clearly different from each other, however, as indicated by the divergent results seen in Western blot analysis where 39-1.37 and 39-1.132 are blot negative while 39-1.124 and 39-1.156 are blot positive. Antibodies in group 5 include 39-1.7, 39-1.128, and 39-1.26. They are similar to mAbs in groups 3 and 4 in that they demonstrated a comparable loss of binding on mutant K143/A but differ as evidenced by better recognition of mutant E129/A. Binding of these antibodies to mutants S13 1/A-T135/A, Y145/A, N180/A, and F201/A-E202/A was essentially equivalent to that observed on wild-type gp39. Group 6, comprising mAbs 39-1.52, 39-1.61, 39-1.77, 39-1.93, 39-1.106, 39-1.109, and 39-1.134, are distinguished from the other anti-gp39 mAbs by an almost total lack of reactivity with mutant F201/A-E202/A. In addition, these antibodies demonstrated a definite although not as significant reduction in reactivity on mutant K143/A. Reactivity of this group of antibodies with the other mutants in the panel was similar to that observed on wild-type gp39. Group 7 includes a single antibody, 39-1.29. This mAb is very similar to those in group 6 except that it appears to recognize the K143/A mutant nearly as well as wild-type gp39. A single antibody, 39-7.3E12, represents group 8. This antibody is notably different from all the others in that it reacted with all the mutants quite well with only a slight loss of reactivity on the K143/A mutant as compared to wild-type gp39.

Collectively, the gp39 mutant reactivity data coupled with the Western blot results define at least eight different recognition profiles and thus eight different epitope specificities among the 24 anti-human gp39 mAbs. As defined above, mAbs in groups 1, 2, 3, 5, and 8 appear to recognize epitopes that are discontinuous or conformational in nature while the specificity of those in groups 4, 6, and 7 appears to be for continuous or linear sequences of gp39.

TABLE 2

Summary of Anti-Human gp39 Monoclonal Antibodies

Antibody Reactivity with gp39 Point Mutants*

| Antibody Group | Antibody | Isotype | E129/A | S131/A T135/A | K143/A | Y145/A | N180/A | F201/A E202/A | Western Blot |
|---|---|---|---|---|---|---|---|---|---|
| 1 | 3-1.3 | G1 | 2 ± 0.3 | 8 ± 1.7 | 27 ± 0.8 | 109 ± 2.9 | 87 ± 5.3 | 106 ± 3.4 | − |
|  | 39-1.21 | G1 | 11 ± 0.4 | 13 ± 0.2 | 61 ± 6.9 | 142 ± 11.9 | 126 ± 1.6 | 103 ± 1.1 | − |
|  | 39-1.25 | G1 | 0 ± 0.8 | 7 ± 1.2 | 63 ± 8.8 | 135 ± 0.3 | 124 ± 7.7 | 114 ± 8.4 | − |
|  | 39-1.63 | G1 | 12 ± 3.1 | 14 ± 1.8 | 26 ± 0.6 | 122 ± 1.5 | 98 ± 9.2 | 84 ± 10.5 | − |
|  | 39-1.122 | G2b | 4 ± 0.9 | 4 ± 1.8 | 60 ± 7.9 | 109 ± 17.7 | 83 ± 11.2 | 88 ± 9.3 | − |
|  | 39-1.23 | G1 | 16 ± 1.4 | 22 ± 0.0 | 59 ± 0.7 | 95 ± 3.8 | 114 ± 31.0 | 101 ± 2.1 | − |
|  | 39-1.138 | G1 | −4 ± 0.2 | −3 ± 0.7 | 54 ± 3.5 | 116 ± 7.1 | 99 ± 4.3 | 124 ± 6.6 | − |
| 2 | 39-1.59 | G1 | 4 ± 3.5 | 14 ± 1.0 | 38 ± 4.1 | 74 ± 6.9 | 55 ± 6.8 | 59 ± 7.4 | − |
| 3 | 39-1.137 | G1 | 8 ± 0.2 | 97 ± 4.4 | 6 ± 0.1 | 111 ± 5.9 | 98 ± 11.2 | 90 ± 8.5 | − |
|  | 39-1.132 | G2b | 23 ± 2.1 | 77 ± 0.6 | 5 ± 0.6 | 94 ± 4.2 | 82 ± 0.2 | 93 ± 11.2 | − |
| 4 | 39-1.124 | G1 | 25 ± 1.2 | 69 ± 6.7 | 4 ± 0.7 | 90 ± 9.3 | 75 ± 1.5 | 85 ± 2.0 | + |
|  | 39-1.156 | G1 | 31 ± 0.8 | 84 ± 16.7 | 8 ± 1.0 | 100 ± 25.6 | 73 ± 10.7 | 76 ± 2.5 | + |

TABLE 2-continued

Summary of Anti-Human gp39 Monoclonal Antibodies

Antibody Reactivity with gp39 Point Mutants*

| Antibody Group | Antibody | Isotype | E129/A | S131/A T135/A | K143/A | Y145/A | N180/A | F201/A E202/A | Western Blot |
|---|---|---|---|---|---|---|---|---|---|
| 5 | 39-1.7 | G2b | 70 ± 2.9 | 89 ± 0.5 | 5 ± 0.1 | 106 ± 4.3 | 93 ± 1.4 | 112 ± 5.0 | – |
|   | 39-1.128 | G2b | 52 ± 0.0 | 116 ± 6.6 | 7 ± 1.8 | 123 ± 5.6 | 133 ± 23.1 | 102 ± 4.7 | – |
|   | 39-1.26 | G1 | 96 ± 3.7 | 103 ± 6.3 | 6 ± 0.3 | 128 ± 1.9 | 137 ± 16.3 | 111 ± 4.3 | – |
| 6 | 39-1.52 | G1 | 124 ± 0.6 | 109 ± 6.8 | 68 ± 3.0 | 18 ± 15.8 | 144 ± 7.5 | 1 ± 0.9 | + |
|   | 39-1.61 | G1 | 94 ± 4.6 | 81 ± 0.1 | 53 ± 3.0 | 92 ± 2.4 | 92 ± 3.1 | 0 ± 0.5 | + |
|   | 39-1.77 | G1 | 28 ± 35.0 | 117 ± 1.5 | 75 ± 10.3 | 122 ± 22.8 | 147 ± 2.6 | 3 ± 1.0 | + |
|   | 39-1.93 | G1 | 99 ± 2.1 | 81 ± 6.5 | 46 ± 3.6 | 103 ± 8.9 | 114 ± 11.4 | 6 ± 1.1 | + |
|   | 39-1.106 | G1 | 130 ± 10.6 | 113 ± 6.0 | 52 ± 16.6 | 124 ± 1.5 | 144 ± 25.1 | 9 ± 1.3 | + |
|   | 39-1.109 | G1 | 96 ± 1.8 | 72 ± 0.6 | 54 ± 8.5 | 108 ± 13.6 | 82 ± 7.9 | 4 ± 4.5 | + |
|   | 30-1.134 | G1 | 109 ± 0.8 | 79 ± 0.6 | 53 ± 3.2 | 98 ± 4.6 | 82 ± 7.7 | 3 ± 0.2 | + |
| 7 | 39-1.29 | G2a | 109 ± 14.5 | 105 ± 7.1 | 91 ± 0.6 | 125 ± 10.6 | 122 ± 2.2 | 1 ± 0.2 | + |
| 8 | 39-7.3E12 | G2a | 102 ± 1.1 | 82 ± 5.5 | 67 ± 3.0 | 114 ± 6.4 | 99 ± 8 | 94 ± 1.3 | – |

*Average ± SD of three independent experiments

EXAMPLE 5

Inhibition of T-cell Dependent B-cell Proliferation and Immunoglobulin Production Activated T cells can induce resting B cells to proliferate and differentiate into immunoglobulin secreting cells. Furthermore, cell contact between activated T cells and B cells is required for B cells to switch from IgM to IgG, IgA or IgE production. As the interaction between CD40 and its ligand is thought to play a critical role in these processes, it was anticipated that anti-gp39 monoclonal antibodies would be capable of interfering with these forms of T cell "help".

The inhibitory effects of anti-gp39 monoclonal antibodies on human B cell activation and differentiation was evaluated in an in vitro T cell dependent B cell proliferation and immunoglobulin synthesis assay system. In this system (Hirohata et al. 1988. *J. Immunol.* 140:3736–3744), activated T cells induce B cell activation, proliferation, and polyclonal antibody production (IgG, IgM, and IgA) in an MHC-unrestricted, Ag non-specific manner. It requires direct contact between B and T cells for the observed B cell events to occur and as such is thought to represent a relevant in vitro system to study B cell/T cell interactions leading to Ab production.

Briefly, human blood mononuclear cells (PBMCs) were isolated by diluting whole blood 1:1 with PBS, overlaying 25 ml onto 10 ml of Lymphocyte Separation Medium (LSM, Organon Teknika) and centrifuging for 25 minutes at 450 g. Cells at the interface were collected and washed once in PBS. Isolated cells were diluted to $5 \times 10^6$/ml in 2% FCS-Iscove's containing 0.25 mM L-leucyl-L-leucine methyl ester hydrobromide (Leu-LeuOMe, Sigma) and incubated at room temperature for 15 minutes to kill monocytes and NK cells (Ohlin et al., 1989. *Immunology* 66:485–490). Treated cells were washed twice with 2% FCS-Iscove's prior to separation of T and B cells.

T cells were isolated by incubating the Leu-LeuOMe treated cells with 150-fold AET-SRBC (sheep red blood cells treated with 0.143M 2-aminoethylisothiouronium bromide (Sigma)) for 5–10 minutes on ice. E-rosette positive T cells ($E^+$-T cells) were separated from the remaining cells by underlaying with cold LSM and centrifuging at 450 g for 25 minutes. The pellet (containing rosetted T cells) was collected and the sheep red blood cells were lysed with 0.83% ammonium chloride for five minutes at room temperature.

Resulting T cells were washed once in 2% FCS-Iscove's. These cells were subsequently treated with mitomycin C ($5 \times 10^6$ $E^+$-T cells and 40 μl mitomycin C/ml) for 40 minutes at 37° C. and then washed three times with 2% FCS-Iscove's. B cells were obtained from the interface of the tubes in which $E^+$-T cells were isolated from AET-SRBC treated PBMCs by centrifugation over an LSM cushion (described above). These cells were washed once in 2% FCS-Iscove's and re-rosetted with AET-SRBC as described above to remove any residual T cells and again centrifuged over an LSM cushion. Cells at the interface were collected, washed once in 2% FCS-Iscove's and are referred to here as B cells.

Costar 96 well plates were coated with 50 μl/well of a 2 μg/ml solution of anti-CD3 monoclonal antibody 64.1 (Hansen et al., In Leucocyte Typing, Springer-Verlag, Inc., pp 195–212 (1984)) in serum free Iscove's medium for a minimum of four hours at room temperature. Excess antibody was aspirated from the wells and 100,000 mitomycin C treated T cells and 2,000 twice rosetted B cells in a total volume of 150 μl of culture medium (Iscove's modified Dulbecco's medium supplemented with 10% FCS) were added to each well. Supernatants collected from hybridomas producing anti-gp39 monoclonal antibody or a negative control monoclonal antibody were then added to each of three wells, 100 μl/well. Additional wells received the same volume of culture medium only. After six days of culture in a 37° C. incubator containing 6% $CO_2$, each set of triplicate wells was assessed for B cell proliferation and total human IgG and IgM.

B cell proliferation was measured by tritiated thymidine uptake. After removal of 100 μl/well of culture supernatant for IgG and IgM analysis (see below), 50 μl of culture medium containing 1 μCi of [$^3$H]thymidine (New England Nuclear, #NET-027) was added to each well. After a further 18 hours of culture at 37° C., the plates were frozen, thawed, and cells harvested onto glass fiber filter mats with a TOMTEC full plate cell harvester. [$^3$H]thymidine incorporation was measured with an LKB Wallace Beta-Plate liquid scintillation counter (#1205). Counts from triplicate wells were averaged and are presented in Table 3 as a percentage ±1 SD of the values seen with medium only control wells.

Human IgG and IgM were quantitated by coating Immulon 2 EIA plates (Dynatech) with 100 μl/well of a 1 μg/ml solution of goat anti-human Ig (Southern Biotechnology Associates) in 0.05M sodium carbonate/sodium bicarbonate buffer, pH 9.6. Plates were sealed and incubated overnight at 4° C. Excess antibody was removed and plates blocked as described in earlier ELISA assays. Following blocking, all wells received 50 μl/well of 2×PTB (2×PBS containing 2% bovine serum albumin (Intergen) and 1% Tween 20)). Culture supernatants diluted 1:10 (for IgM analysis) and 1:40 (for IgG analysis) in culture medium were added to the wells, 50 μl/well, and incubated for one hour at room temperature. These dilutions were arrived at in a preliminary experiment using serial dilutions of culture supernatants from medium only wells and selecting that dilution(s) that yielded optical density values near the upper end of the most linear part of the response curve for IgG and IgM. Supernatants were removed, the plates washed twice with PBS-Tween and HRP labeled goat anti-human IgG or IgM (Jackson Immunological Laboratories #109-036-098 and #109-036-129), appropriately diluted in 1×PTB (2×PTB diluted 1:1 with PBS), added to respective wells, 100 μl/well. After a one hour incubation at room temperature, HRP labeled reagents were removed and the plates washed three times with PBS-Tween. Disclosure of bound HRP labeled reagents and the measurement of resulting optical density was as described in other ELISA assays detailed above. Optical density values from the triplicate wells were averaged and are presented in Table 3 as a percentage±1 SD of the values seen with medium only control wells.

As shown in Table 3, each of the anti-gp39 monoclonal antibodies tested was capable of significantly inhibiting the T cell driven proliferation of B cells, resulting in values that were only 2–4% of that seen in wells that did not receive gp39 specific antibody. Concomitantly, the production of IgG and IgM were also significantly suppressed.

The inhibitory effect of the various anti-gp39 monoclonal antibodies on T cell dependent human B cell immunoglobulin production was further investigated in a more quantitative manner using defined concentrations of purified antibody. Antibodies were affinity purified from culture supernatants on Protein A Sepharose or GammaBind Plus Sepharose columns (Pharmacia) according to manufacturer's instructions and quantitated by optical density absorbance using an extinction coefficient of 1.4. Experiments were set up as described above with the following modifications. Half area Costar 96 well plates were utilized and the concentration anti-CD3 antibody used to coat the wells was 4 μg/ml. All wells received 150,000 mitomycin C treated T cells and 20,000 B cells in a total volume of 100 μl of culture medium. Anti-gp39 and negative control antibodies were diluted to 60, 6, and 0.6 μg/ml in culture medium and 50 μl of each dilution added to each of three wells for a final concentration of each antibody in the culture wells of 20, 2 and 0.2 μg/ml. Control wells received 50 μl/well of culture medium only. Cells were cultured for a total of 10 days in a 37° C./6% CO2 incubator at which time supernatants from triplicate wells were pooled and assessed for total human IgG and IgM. Measurement of human IgG and IgM were as described above except that each pooled supernatant was assayed in triplicate, the supernatants were diluted in 2% FCS-Iscove's to much higher dilutions given the longer period of cell culture (and thus antibody production), wells on the assay plates did not receive 2×PTB prior to addition of diluted supernatants, and HRP reagents were diluted in blocking buffer.

TABLE 3

Suppression of in vitro B Cell Proliferation and Antibody Production by Anti-Human gp39 mAbs

| mAb | [³H]Thymidine Incorporation (% of Medium Control) | Ig Produced (% of Medium Control) | |
|---|---|---|---|
| | | IgM | IgG |
| 39-1.3 | 3.5 ± 0.7 | 33.5 ± 15.4 | 60.2 ± 3.6 |
| 39-1.7 | 3.3 ± 0.5 | 13.9 ± 9.1 | 31.8 ± 9.6 |
| 39-1.26 | 2.1 ± 0.1 | 10.0 ± 3.7 | 24.0 ± 8.3 |
| 39-1.29 | 3.9 ± 0.7 | 43.4 ± 11.4 | 39.8 ± 6.4 |
| 39-1.37 | 2.4 ± 0.2 | 20.2 ± 4.1 | 44.8 ± 10.9 |
| 39-1.61 | 3.4 ± 0.6 | 10.6 ± 4.6 | 32.2 ± 15.0 |
| 39-1.77 | 2.1 ± 0.6 | 11.7 ± 2.1 | 41.9 ± 2.1 |
| 39-1.106 | 2.9 ± 0.3 | 17.9 ± 4.9 | 28.6 ± 8.3 |
| 39-1.124 | 3.5 ± 0.6 | 17.0 ± 5.7 | 36.5 ± 16.9 |
| 39-1.128 | 3.1 ± 0.5 | 21.7 ± 9.5 | 53.3 ± 6.2 |
| 39-1.132 | 3.3 ± 0.4 | 13.0 ± 4.7 | 50.1 ± 2.0 |
| 39-1.134 | 2.3 ± 0.8 | 12.5 ± 4.1 | 33.5 ± 10.2 |
| 39-1.156 | 2.7 ± 0.1 | 12.2 ± 4.8 | 26.9 ± 5.6 |
| Neg. Cont. mAb | 87.9 ± 7.9 | 87.9 ± 13.8 | 114.9 ± 28.5 |

Data from these experiments are presented in Table 4. At the highest concentration of antibody used, 20 μg/ml, all anti-gp39 antibodies significantly inhibited the production of both IgG and IgM. At this concentration, levels of human antibody generated were consistently 10–30% of that seen in the presence of medium only. As the concentration of anti-gp39 antibody was decreased so to, in general, was the level of inhibition. At the two lowest concentrations of anti-gp39 antibodies employed, 2 and 0.2 μg/ml, it was quite apparent that certain anti-gp39 antibodies including, in particular, 39-1.7, 39-1.26, 39-1.77, 39-1.106, 39-1.134, and 39-7.3E12, were much more effective at inhibiting human IgG and IgM production than were others. This observation suggests that epitope specificity and/or antibody avidity is an important parameter in the degree to which monoclonal antibodies directed to gp39 can interfere with gp39-CD40 interaction.

TABLE 4

Comparative Suppression of in vitro B cell Ab Production by Anti-Human gp39 mAbs Inhibition of in vitro Antibody Synthesis % of Medium Control ± SD*

| mAb | IgG | | | IgM | | |
|---|---|---|---|---|---|---|
| | 20 μg/ml | 2 μg/ml | 0.2 μg/ml | 20 μg/ml | 2 μg/ml | 0.2 μg/ml |
| 39-1.3 | 9 ± 7 | 53 ± 16 | 91 ± 7 | 23 ± 3 | 63 ± 17 | 94 ± 15 |
| 39-1.122 | 13 ± 1 | 28 ± 6 | 70 ± 12 | 20 ± 23 | 60 ± 18 | 84 ± 6 |
| 39-1.38 | 21 ± 4 | 60 ± 14 | 90 ± 9 | 29 ± 23 | 91 ± 29 | 101 ± 22 |

TABLE 4-continued

Comparative Suppression of in vitro B cell Ab Production by Anti-Human gp39 mAbs

| | Inhibition of in vitro Antibody Synthesis % of Medium Control ± SD* | | | | | |
|---|---|---|---|---|---|---|
| | IgG | | | IgM | | |
| mAb | 20 μg/ml | 2 μg/ml | 0.2 μg/ml | 20 μg/ml | 2 μg/ml | 0.2 μg/ml |
| 39-1.59 | 21 ± 6 | 57 ± 10 | 85 ± 22 | 34 ± 25 | 82 ± 35 | 84 ± 13 |
| 39-1.37 | 18 ± 4 | 39 ± 23 | 74 ± 16 | 26 ± 16 | 62 ± 14 | 91 ± 12 |
| 39-1.132 | 11 ± 1 | 25 ± 17 | 66 ± 10 | 23 ± 24 | 60 ± 20 | 102 ± 23 |
| 39-1.124 | 11 ± 1 | 20 ± 8 | 54 ± 20 | 21 ± 28 | 47 ± 31 | 76 ± 13 |
| 39-1.156 | 11 ± 6 | 15 ± 13 | 43 ± 22 | 14 ± 6 | 28 ± 10 | 81 ± 8 |
| 39-1.7 | 17 ± 8 | 12 ± 7 | 34 ± 19 | 20 ± 6 | 27 ± 12 | 58 ± 15 |
| 39-1.128 | 19 ± 1 | 19 ± 3 | 55 ± 18 | 26 ± 11 | 46 ± 22 | 85 ± 21 |
| 39-1.26 | 22 ± 18 | 15 ± 9 | 41 ± 14 | 26 ± 13 | 27 ± 28 | 78 ± 2 |
| 39-1.77 | 11 ± 6 | 16 ± 5 | 38 ± 16 | 23 ± 39 | 28 ± 24 | 68 ± 34 |
| 39-1.106 | 8 ± 2 | 11 ± 5 | 21 ± 12 | 27 ± 23 | 22 ± 21 | 41 ± 14 |
| 39-1.134 | 10 ± 4 | 15 ± 5 | 28 ± 7 | 23 ± 13 | 27 ± 26 | 65 ± 32 |
| 39-1.29 | 10 ± 1 | 13 ± 3 | 49 ± 23 | 23 ± 16 | 37 ± 11 | 86 ± 9 |
| 39-7.3E12 | 9 ± 1 | 12 ± 4 | 37 ± 16 | 11 ± 2 | 18 ± 16 | 72 ± 10 |

*Average ± SD of three independent experiments except for data compiled at 20 μg/ml antibody concentration for which there were only two experiments.

EXAMPLE 6

Detection of Mutant gp39 in an X-Linked Hyper IgM Patient

Monoclonal antibodies with different binding characteristics with mutant human gp39 were used to determine whether point mutations in gp39 could be recognized in a blood sample taken from an X-linked-hyper IgM patient. In this assay, patients whose cells showed positive staining with the gp39 specific monoclonal antibodies, but no staining with CD40Ig, the normal ligand, would be known to express gp39 protein that is nonifnctional and could be diagnosed as X-HIM. Using a panel of monoclonal antibodies, with known differences in epitopes, provides for a greater number of differing mutations which can be detected in an X-HIM sample. Using this assay, it is not totally possible to exclude Common Variable Immunodeficiency as a diagnosis, but it is expected that a significant percentage of X-HIM patients can be detected by this approach. A subset of HIM patients, those whose gp39 defect results in a lack of internal expression due, for example, to a mutation to a stop codon early in the gp39 coding sequence, also could not be confirmed by this approach.

Briefly, T cells are isolated from a sample of peripheral blood lymphocytes from a patient by Ficoll gradient centrifugation followed by rosetting using sheep erythrocytes. Staining of fixed, permeabilized cells was performed using the methods of Jung et al. (*J. Immunol. Methods* 159:197–207 (1993) with modifications as described.

Isolated T cells were stimulated with PMA (10 ng/ml) and ionomycin (1 μg/ml) in the presence of monensin at 3 mM for three hours. The stimulated cells were then washed with PBS and fixed by incubation in 4% paraformaldehyde in Hank's balanced salt solution for 10 minutes at 4° C. The fixed cells were washed once with PBS, then permeabilized and blocked by incubation in blocking buffer (0.1% saponin, 10% goat serum in PBS) for 10 minutes at room temperature.

Cells were pelleted and resuspended in 0.1% saponin, 2% fetal bovine serum in PBS and aliquots were prepared for staining at an approximate density of 1×10$^7$ cells/ml. Monoclonal antibodies were added to a final concentration of 10 μg/ml and the cells were incubated at room temperature for 30 minutes prior to washing twice with blocking buffer and resuspension in blocking buffer containing FITC-conjugated goat anti-mouse Fc. After an additional 20 minute incubation at room temperature, the cells were washed twice with 2% FBS in PBS and analyzed by flow cytometry.

As a control and to test the feasibility of detecting gp39 in the interior of a cell normal T cells were isolated and treated as above except prior to fixation the cells were treated for 5 minutes with trypsin to remove surface expressed gp39. The cells were then fixed and stained as above. A comparison of staining of non-activated with activated T cells allows for the demonstration of specific staining within normal T cells.

In Table 5 is provided a summary of staining obtained with T cells isolated from an X-HIM patient with anti-gp39 monoclonal antibodies.

TABLE 5

Summary of Staining of T Cells Obtained from X-HIM Patient with anti-gp39 mAb

| Antibody | CD[1] | NC[2] | Western | Isotype |
|---|---|---|---|---|
| 39-1.3 | − | + | − | G1 |
| 39-1.122 | − | + | − | G2b |
| 39-1.138 | − | + | − | G1 |
| 39-1.124 | − | + | + | G1 |
| 39-1.7 | − | + | − | G2b |
| 39-1.26 | − | + | − | G2b |
| 39-1.106 | + | + | + | G1 |
| 39-1.134 | + | + | + | G1 |

[1]X-HiM patient CD (Aruffo et al. 1993, Cell 72:291)
[2]Normal control

EXAMPLE 6

Construction of Recombinant anti-gp39 Single-Chain Variable Regions

In this example, the nucleotide sequences of the heavy chain variable region (VH) and the light chain variable region (VL) of two anti-human gp39 monoclonal antibodies

[39-1.7 (7) and 39-1.106 (106)] are determined and isolated. The DNA fragments encoding the VH and VL of each monoclonal antibody were then assembled into a continuous expression cassette using an intervening sequence encoding a (Gly$_4$Ser)$_3$ linker. The cassettes were expressed in mammalian cells and functional activity of the recombinant single chain antibody (sFv) molecules were determined.

A. Isolation of RNA cDNA Synthesis and PCR Amplification

RNA was isolated from 5×10$^7$ clone 106 or clone 7 hybridoma cells using an mRNA isolation kit (Stratagene, LaJolla, Calif.). cDNA was generated from the RNA using the StrataScript RT-PCR kit (Stratagene, LaJolla, Calif.) and immunoglobulin constant region specific antisense primers. The CK-specific primer was complementary to nucleotide sequence 228 to 257 of the murine kappa light chain constant region. This primer was used for first strand synthesis of both the clone 106 and clone 7 VL cDNAs. An IgG$_1$-specific antisense primer or an IgG$_{2b}$-specific antisense primer were used to generate clone 106 and clone 7 VH cDNAs, respectively. The IgG$_1$-specific antisense primer was complementary to nucleotides 100 to 121 of the murine IgG$_1$, CHI region and the IgG$_{2b}$-specific antisense primer was complementary to nucleotides 101 to 123 of the murine IgG2b CH1 region. First strand reactions were set up using 300 ng of antisense primer and 0.5 μg mRNA.

The cDNAs were purified using Geneclean™ (Bio101, LaJolla, Calif.) and subsequently polyG-tailed with 10 mM dGTP and terminal deoxynucleotidyl transferase (Stratagene) for 1 hour at 37° C. Poly G-tailed cDNAs were purified again using GeneClean™. Two μl of each cDNA were amplified by anchor-PCR (Saiki et al., 1988. *Science* 239:487–491) in a total volume of 100 μl using 20 μmol of each dNTP, 100 pmol of sense and antisense primers and 2U Taq polymerase. The sense primer contained a region complementary to the polyG tail (Loh et al. 1989. *Science* 243:217–220) and a XbaI site (underlined).

5'-CGTCGA
<u>TCTAGA</u>GCATGTGCAAGTCCGATGAGTCCCCCCCCCC
CCC-3'                                    Seq. I.D. No. 7

The antisense primers were nested primers containing a HindIII site (underlined) and annealed to either nucleotides 101–125 of murine Cκ

5'-CGTCAT<u>AAGCTT</u>CAGGAAGCACACGACTGAGGC
AC-3'                                     Seq. I.D. No. 28 or to nucleotides 47–69 of murine IgG$_1$ CH1

5'-CGTCAT<u>AAGCTT</u>GTCACCATGGAGTTAGT
TTG-3'                                    Seq. I.D. No. 9 or to nucleotides 38–62 of murine IgG$_{2b}$ CH1

5'-CGTCAT<u>AAGCTT</u>GAACCAGTTGTATCTCCACACC
CAG-3'                                    Seq. I.D. No. 10

Reactions were carried out in a Perkin-Elmer Cetus thermal cycler (Norwalk, Conn.) with a 33 cycle program of 30 sec. denaturation at 94° C., 90 sec. annealing at 45° C. and 90 sec. extension at 72° C.

PCR-amplified VL and VH fragments were digested with XbaI and HindIII, ligated into the pUC19 vector and transformed in DH5a *E. coli*. Clones containing VL or VH were identified by DNA sequencing. Consensus sequences for clone 106 (FIG. 1A and FIG. 1B) or clone 7 (FIG. 2A and FIG. 2B) were determined by analyzing the sequence of multiple VL or VH clones and alignment of the deduced amino acid sequences with previously published murine VL and VH sequences (Kabat et al. 1987. U.S. Department of Health and Human Services). The nucleotide and deduced amino acid sequence for clone 106 VL and VH are depicted in FIG. 1A and FIG. 1B (Seq. I.D. Nos. 11 through 14) and the nucleotide and deduced amino acid sequence for 7 VL and VH are depicted in FIG. 2A and FIG. 2B (Seq. I.D. No. 15 through 18).

B. Construction of Clone 7 and Clone 106 sFv Expression Cassettes

Single chain sFv were constructed in the VL-VH orientation for both 7 and 106, each cassette containing an intervening (Gly$_4$Ser)$_3$ linker (Huston et al. 1988. *Proc. Nat'l Acad. Sci. USA* 85:5879–5883). To create the 106 VL-VH cassette, the clone 106 VL gene was reamplified from the pUC19 sequencing construct using a sense PCR primer (106 γl SalI) that encoded a SalI site immediately prior to sequence encoding the first residue of the mature VL. The antisense primer (106 γlvhLK3') was complementary to sequence encoding the last nine residues of the VL and the first 12 residues of the (Gly$_4$Ser)$_3$ linker. Additionally, the 106 VH was reamplified from the pUC19 sequencing construct using a sense primer (106 γlvhLK5') that encoded the first 11 residues of the (Gly$_4$Ser)$_3$ linker followed by the first nine residues of the mature VH and an antisense primer (106vhBclI) complementary to sequence encoding the last nine residues of the VH region and a BclI site. The modified VL and VH PCR products were then purified using Geneclean™ (Bio101, LaJolla, Calif.) and were added to a single PCR reaction in the presence of excess sense VL (106 γlSalI) and antisense VH (106vhBclI) primers so that DNA encoding the individual 106 VH and VL domains were linked into a single coding region by overlap extension PCR.

Similarly, to create the 7 VL-VH sFv cassette, the 7 VL gene was reamplified from the pUC 19 sequencing construct using a sense PCR primer (7 γ2bSalI) that encoded a SalI site immediately prior to sequence encoding the first residue of the mature 7 VL; and an antisense primer (7 γ2bv1LK3') complementary to sequence encoding the last nine residues of the VL and the first 12 residues of the (Gly$_4$Ser)$_3$ linker. DNA encoding 7 VH was reamplified from the pUC19 sequencing construct with a sense primer (7 γ2bvhLK5') encoding the first 11 residues of the (Gly$_4$Ser)$_3$ linker followed by the first nine residues of the mature VH and an antisense primer (7 γ2bvhBclI) complementary to the sequence encoding the last nine amino acid residues of the VH region and a BclI site. DNA encoding 7 VH and VL were linked into a single coding region by overlap extension PCR using excess VL sense (7 γ2bSalI) and VH antisense (7 γ2bvhBclI) PCR primers.

TABLE 6

Primers Used to Construct Clone 7 and Clone 6 sFv Expression Cassettes

| Primer | Sequence (5' to 3')[1] |
|---|---|
| 7 γ2bSalI | ATCGTCTAG<u>GTCGAC</u>ATTGTGCTGACACAGTCTCCTGTTTCC, SEQ ID. #19 |

TABLE 6-continued

Primers Used to Construct Clone 7 and Clone 6 sFv Expression Cassettes

| Primer | Sequence (5' to 3')[1] |
|---|---|
| 7 γ2bVlLK3' | GCCACCCGACCCACCACCGCCCGAGCCACCGCCACCCCGTCTT ATTTCCAACTTTGTCCC, SEQ ID. #20 |
| 7 γ2bVhLK5' | TCGGGCGGTGGTGGGTCGGGTGGCGGCGGATCTGAGGTCCAG CTGCAACAGTCTGGACCT, SEQ ID. #21 |
| 7 γ2bBclI | TCAGTGCTGATCAGAGGAGACTGTGAGAGTGGTGCCTTGGCC, SEQ ID. #22 |
| 106 γlSalI | ATCGTCTAGGTCGACATCCAGATGACTCAGTCTCCAGCCTCC, SEQ ID. #23 |
| 106 γlVlLK3' | GCCACCCGACCCACCACCGCCAGCGCCACCGCCACCCCGTTTC AGCTCCAGCTTGGTCCC, SEQ ID. #24 |
| 106 γlVhLK5' | TCGGGCGGTGGTGGGTCGGGTGGCGGCGGATCTGAAGTGAAG CTGGTGGAGTCTGGGGGA, SEQ ID. #25 |
| 106 γlBclI | TCAGTGCTGATCAGAGGAGACGGTGACTGAGGTTCCTTGACC, SEQ ID. #26 |

[1]Restriction sites underlined

The 106 and 7 VL-link-VH sFv gene cassettes were assembled for sFv-Ig expression in a variant of pUC 19 called pUC-Ig that has been passed through a dam⁻ strain of E. coli (NEB 208) to allow restriction enzyme cutting at the BclI site. This vector contained the L6 Vκ leader sequence inserted as a HindIII-SalI fragment and a BclI site preceding sequence encoding the hinge-$CH_2$—$CH_3$ of human $IgG_1$, followed by a stop codon and an XbaI site.

The cysteine residues in the hinge region were mutated to serines to favor the production of monomeric sFvIg (Hayden et al. 1994. *Therapeutic Immunol.* 1:3–15). The 106 and 7 VL-link-VH sFv gene cassettes were cut with SalI and BclI and were ligated into pUC-Ig. DH5α E. coli were transformed with the constructs and colonies were screened for inserts. The entire L6Vκ leader/VL-link-VH sFv/human Ig cassettes for both the 106 and 7 sFv were cut from pUC-Ig using HindIII and XbaI and were transferred to the pCDM8 mammalian expression vector. Following ligation of 7 and 106 sFv expression cassettes into the modified pCDM8 vector, the plasmids were amplified in MC1061/p3 E. coli cells and DNA was recovered and purified for transfection into COS cells.

C. COS Cell Transfection, Purification, and Characterization of sFv-Ig Fusion Proteins COS cells were transfected with expression plasmids as previously described (Linsley et al. 1991. *J. Exp. Med.* 173:721–730; Aruffo and Seed, 1987. *Proc. Nat'l Acad. Sci. USA* 84:8573–8577). Plasmid DNA was added to transfection media at 1 μg/ml in a total volume of 12 ml/150 mm plate. Spent culture supernatant was pooled and cellular debris was removed by low-speed centrifigation.

106 and 7 sFv-Ig were purified by applying clarified supernatant to a column of immobilized protein A (Repligen Corp., Cambridge, Mass.) equilibrated with 0.05M sodium citrate, pH 8.0 (Linsley et al. 1991. *J. Exp. Med.* 173:721–730). For 500 ml of supernatant, 1 ml of packed bed volume of protein A was used. After loading the column (1 ml/minute), the column was washed with 100 mM potassium phosphate, pH 8.0, and bound protein was eluted with 0.05M sodium citrate, pH 3.0. Fractions were neutralized, pooled and dialyzed against PBS. Protein concentration was determined using a commercially available protein assay kit (Bio-Rad, Richmond, Calif.) based on the Lowry technique.

Expression levels and molecular size of the fusion proteins were determined by immunoprecipitation with protein A and SDS-PAGE, followed by Western blotting. Polyacrylamide gels forming a linear 6–15% gradient with a 4% stacker were run overnight at 10 mAmp. Gels were immunoblotted onto nitrocellulose membranes using a Western semi-dry transfer apparatus (Ellard Instruments, Seattle, Wash.) at 3 mAmp/cm² for 1 hour. Blots were blocked with 2% nonfat milk plus 0.1% Tween in PBS (blocking buffer) for 1 to 2 hours and then incubated with alkaline phosphatase conjugated goat anti-human IgG (Boehringer-Mannheim, Indianapolis, Ind.) at a 1:1500 dilution in blocking buffer for 1 hour. Blots were then washed three times with blocking buffer and were developed in Western blue (Promega, Madison, Wisc.) for 5–15 min. before stopping color development by rinsing with distilled water.

The 7 sFv-Ig and 106 sFv-Ig proteins were tested for binding to human gp39 by an ELISA assay. Briefly, flat bottom flexible 96-well microtiter plates (Falcon) were coated overnight with rat anti-mouse Lyt2a monoclonal antibody 53–6 at 2 μg/ml in PBS at 4° C. After removing gp (sgp39) used as transfection supernatant was added to the plates (100 μl per well) and incubated overnight at 4° C. Excess sgp39 was removed by washing, and clone 7 sFv-Ig or clone 106 sFv-Ig proteins (100 μl per well) were added. Plates were incubated for 2 hours at room temperature and washed twice with PBS containing 0.1% BSA. Goat anti-human horseradish peroxidase (American Qualex, Anaheim, Calif.) in conjugate buffer (Genetics Systems, Seattle, Wash.) was added (100 μl per well) and incubated for 1 hour at room temperature. Unbound conjugate was removed by two washes with PBS containing 0.1% BSA and 100 μl per well of a 1:100 dilution of tetramethyl-benzidine in citrate buffer (Genetic Systems) was added to the wells. The color reaction was stopped with 30 μl per well of 3M $H_2SO_4$ and the optical density was measured at 450–595 nm with a Titertek multiwell plate reader.

Figure 3B:
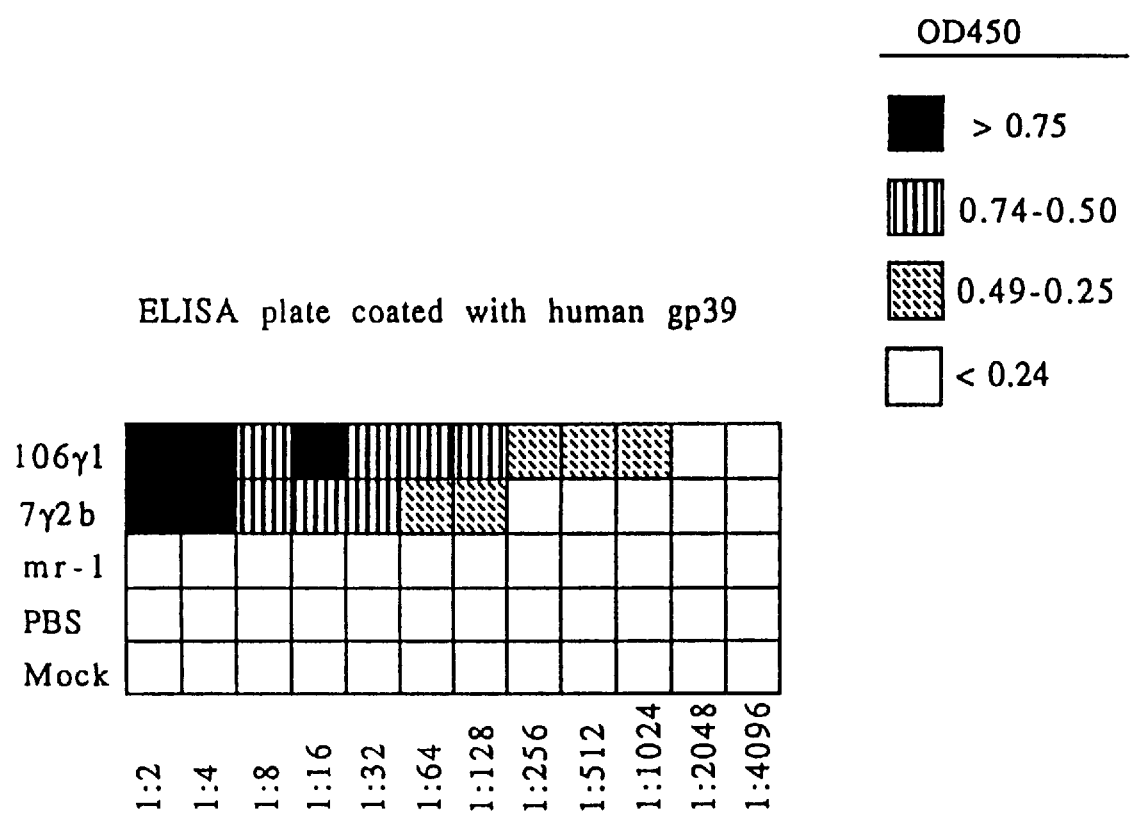
Figures 4A, 4B:
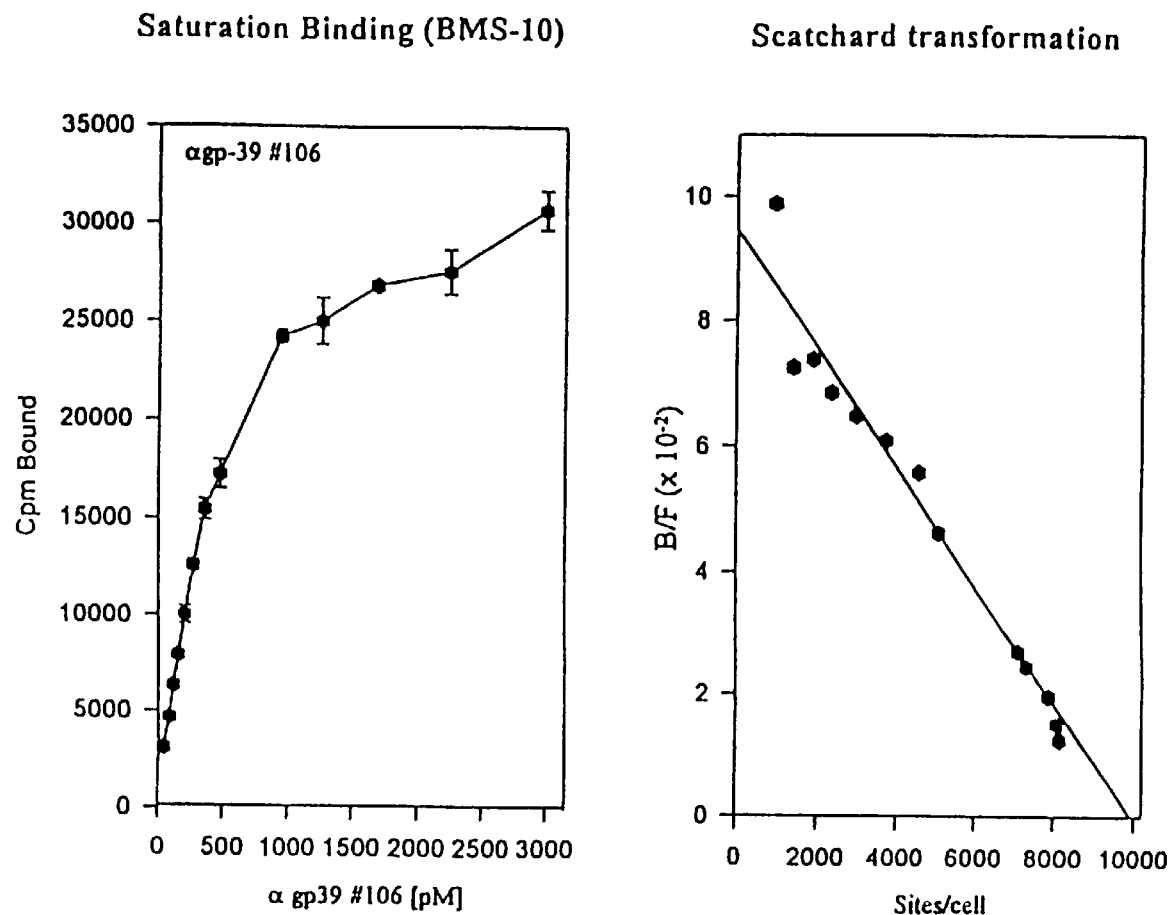
FIGS. 4A and 4C show the comparative binding of bivalent 106 monoclonal antibody and 106 sFv-Ig to Jurkat cells constitutively expressing gp39. Iodinated bivalent 106 mAb was compared to iodinated 106 sFv-Ig for binding to gp39 expressed on BMS-10 Jurkat cells. The calculated affinities were Kd=$4 \times 10^{-10} \pm 6 \times 10^{-11}$ for bivalent 106 mAb (FIG. 4A) and Kd=$1.6 \times 10^{-9} \pm 3.3 \times 10^{10}$ for 106 sFv-Ig (FIG. 4C). Scatchard transformation showed that both bivalent 106 mAb and 106 sFv-Ig bound approximately 10,000 sites per cell (FIGS. 4B and 4D).
Figure 4C:
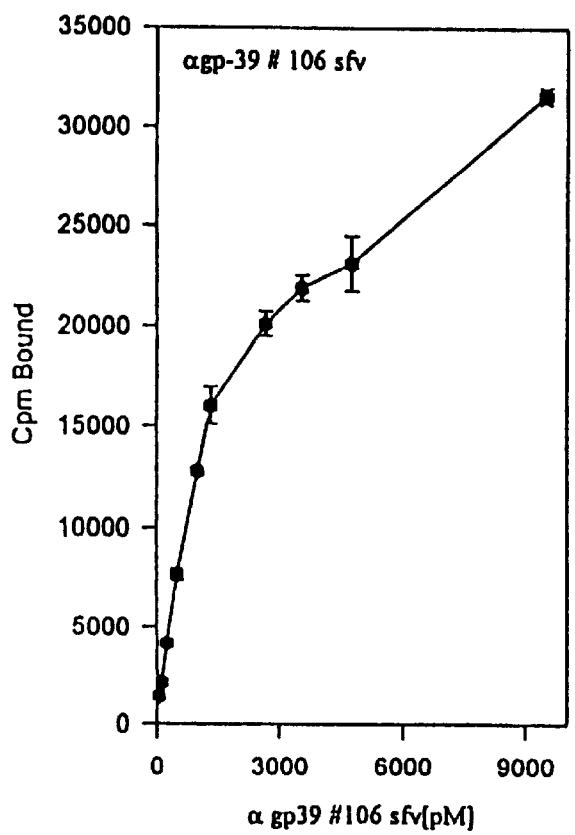
Figure 4D:
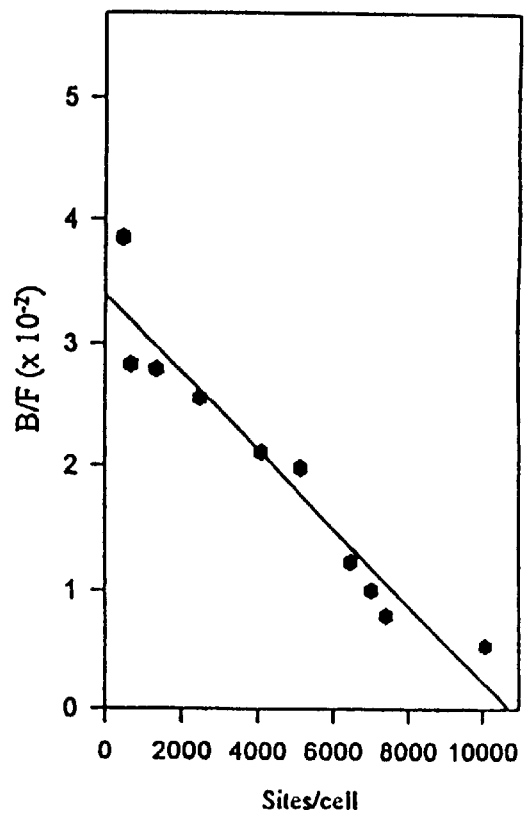

Transfection supernatants from several clone 106 sFv-Ig and clone 7 sFv-Ig clones bound well to human gp39, and reacted very weakly (106) or not at all (7) on murine gp39. Representative results of 106 and 7 sFv-Ig binding are shown in FIG. 3. Binding affinity determinations for the 106 sFv-Ig versus native 106 monoclonal antibody using purified radiolabeled protein were carried out. Saturation binding curves, shown in FIG. 4, showed that labeled native 106 monoclonal antibody (FIG. 4A) bound to Jurkat cells constitutively expressing gp39 with approximately three-fold greater affinity than 106 sFv-Ig (FIG. 4C). However, the affinity of the 106 sFv-Ig was still quite high (measured Kd=$1.6 \times 10^{-9}$). It was determined that native 106 monoclonal antibody bound to 10,000 sites per cell by Scatchard transformation which is complete agreement with the number of sites per cell bound by 106 sFv-Ig (FIGS. 4B and 4D).

The ability of the 7 sFv-Ig and 106 sFv-Ig to inhibit the production of IgG and IgM in an in vitro T cell dependent B cell antibody production system and comparison of this effect with that seen for the parental 39-1.7 and 39-1. 106 antibodies was assessed as described earlier for the parental antibodies with a few minor modifications. Cell cultures were initiated with 100,000 mitomycin C treated T cells and 2,000 B cells in Costar half area plates. Purified parental antibodies and their respective purified sFv-Igs were quantitated using a Bio-Rad Protein Assay kit (#500-0006). Each parental antibody was tested at final concentrations of 1, 0.5, 0.25 and 0.125 µg/ml. Each sFv-Ig was evaluated at final concentrations of 0.68, 0.34, 0.17, and 0.085 µg/ml. Although the concentration of parental antibody and its respective sFv-lg in terms of µg/ml were different, the concentration of each with respect to the number of antigen binding fragments was equivalent when overall valency (two per parental antibody, one for its sFv-Ig) and molecular weight (160,000 kD for parental antibody, 55,000 kD for sFv-Ig) were taken into account. Thus, the final concentrations of antigen binding fragments (binding sites) compared in this experiment were 7.53, 3.76, 1.88, and $0.94 \times 10^{12}$ binding sites/ml.

Following addition of the antibodies and sFv-Igs, the plates were cultured in a humidified 37° C./6% $CO_2$ incubator for 10 days after which culture supernatants from triplicate wells were pooled and assessed for total human IgG and IgM as described earlier. Data are presented in Table 7 where Ig levels are expressed as a percentage of that observed with medium only (no anti-gp39 antibody) controls. As shown in Table 7, both the 7 sFv-Ig and 106 sFv-Ig were capable of substantially suppressing the production of both IgG and IgM by human B cells. Interestingly, their ability to suppress was at least equivalent and at some concentrations, even better, than that observed for the parental antibodies.

TABLE 7

Suppression of in vitro Antibody Production by Whole Anti-Human gp39 Monoclonal Antibodies and their sFv-Ig Derivatives

| Ab Conc. (binding sites × $10^{12}$) | Inhibition of IgG Synthesis % of Medium Only Control | | | | Inhibition of IgM Synthesis % of Medium Only Control | | | |
|---|---|---|---|---|---|---|---|---|
| | 7 | 7 sFv-Ig | 106 | 106 sFv-Ig | 7 | 7 sFv-Ig | 106 | 106 sFv-Ig |
| 7.53 | 12 | 18 | 11 | 14 | 14 | 21 | 25 | 12 |
| 3.76 | 17 | 19 | 24 | 12 | 24 | 19 | 19 | 12 |
| 1.88 | 11 | 24 | 26 | 10 | 29 | 34 | 27 | 12 |
| 0.94 | 60 | 12 | 37 | 21 | 64 | 32 | 34 | 19 |

EXAMPLE 7

Humanization of Variable Regions of anti-gp39 Monoclonal Antibody

A. Determination of Human Templates for 106 VL and VH

Figure 5:
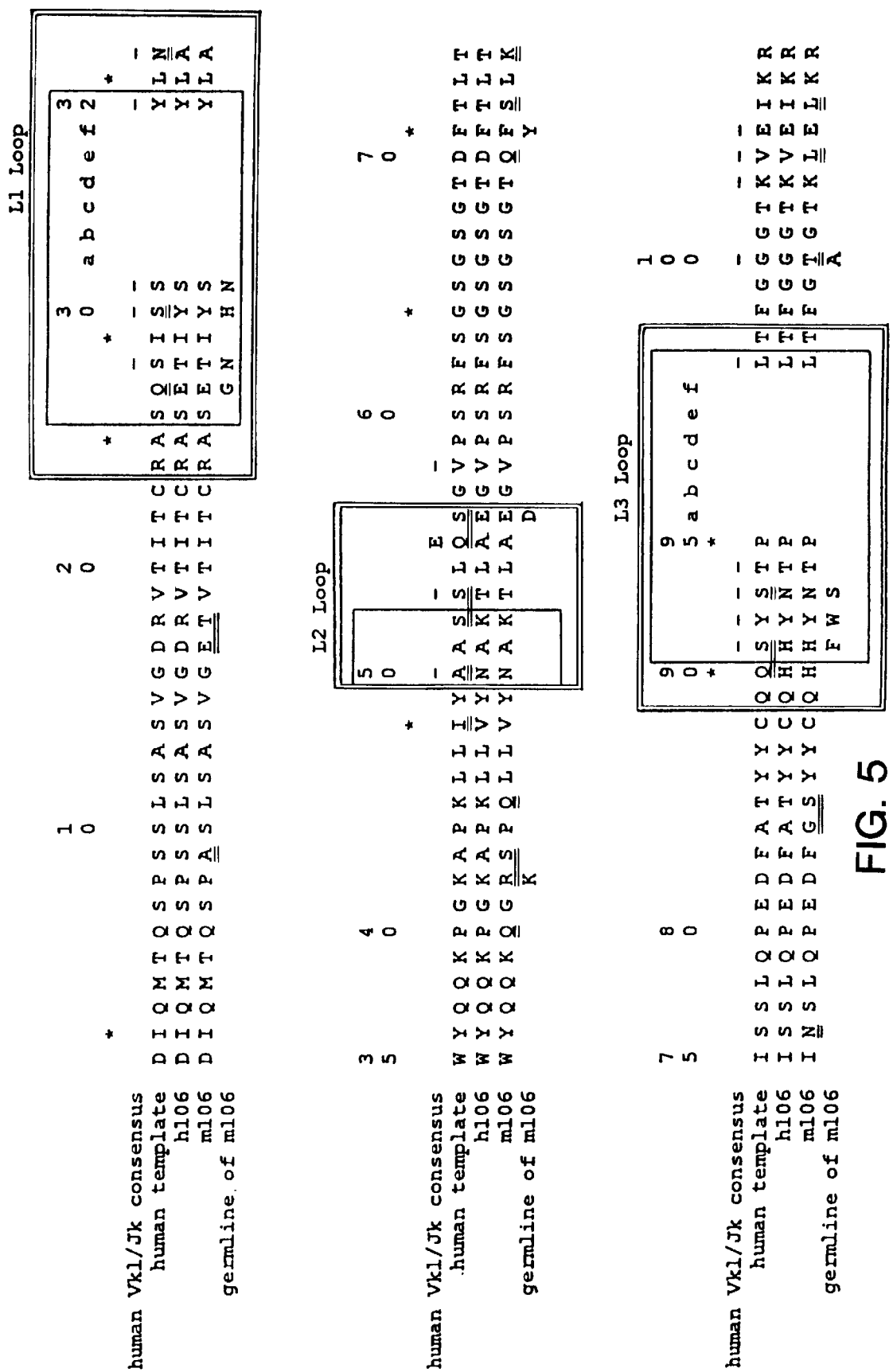
FIG. 5 depicts the 106 VL humanization template. The original murine sequence is shown in the fourth row (m106, Seq. ID. #27) with the murine germline sequence beneath it. The chosen human template sequence is shown in the second row (human template, Seq. ID. #29) with its human consensus sequence above it. The humanized 106 VL sequence (h 06, Seq. ID. #28) is shown between the human template and the murine 106 VL sequence. It consists essentially of human framework residues and murine hypervariable residues. The hypervariable regions as defined by Kabat et al. (*Sequences of Proteins of Immunological Interest*, 4th ed., U.S. Health and Human Services, Washington, D.C. (1987)) are shown outlined with a double line. The L1, L2 and L3 loops are outlined in a single line and structural determinants defined by Chothia are shown by asterisks (Chothia and Lesk, 1987, *J Mol. Biol.* 196: 901). Human or murine residues differing from the humanized 106 VL are double underlined. The human Jκ was chosen on the basis of homology to the 106 Jκ.

The murine 106 VL (kappa) and VH sequences were used to search the IgGe (germline) data set for murine germline nucleotide sequences with the closest homology to 106 VL with a FASTA search using only nucleotides encoding the mature peptide. This search produced two murine sequences followed by many human sequences, the best match being designated "Musigkva" (Accession No. J00545). The homology between the translated 106 VL and J00545 (germline of 106) is shown in FIG. 5. Only the differences are printed for the germline sequence. These differences are probable sites of somatic mutation. However, it is possible that 106 VL is derived from an as yet unidentified murine germline gene.

The human germline amino acid sequence with closest homology to 106 VL was determined by performing a FASTA search on the IgP (protein) data set. This data set contained both germline and rearranged sequences. After discarding the rearranged sequences, the best homology match was found with germline sequences designated "02" (Accession No. X59312) and "012" (Accession No. X59315). It was noted that all but one (Leu90) of the structural determinants for the CDR loops were conserved, as was the size of the CDR loops between murine 106 VL and the human template. It was also noted that all of the CDR loops in the light chains of the murine sequence and human template belong to the same canonical structure class.

Figure 6A:
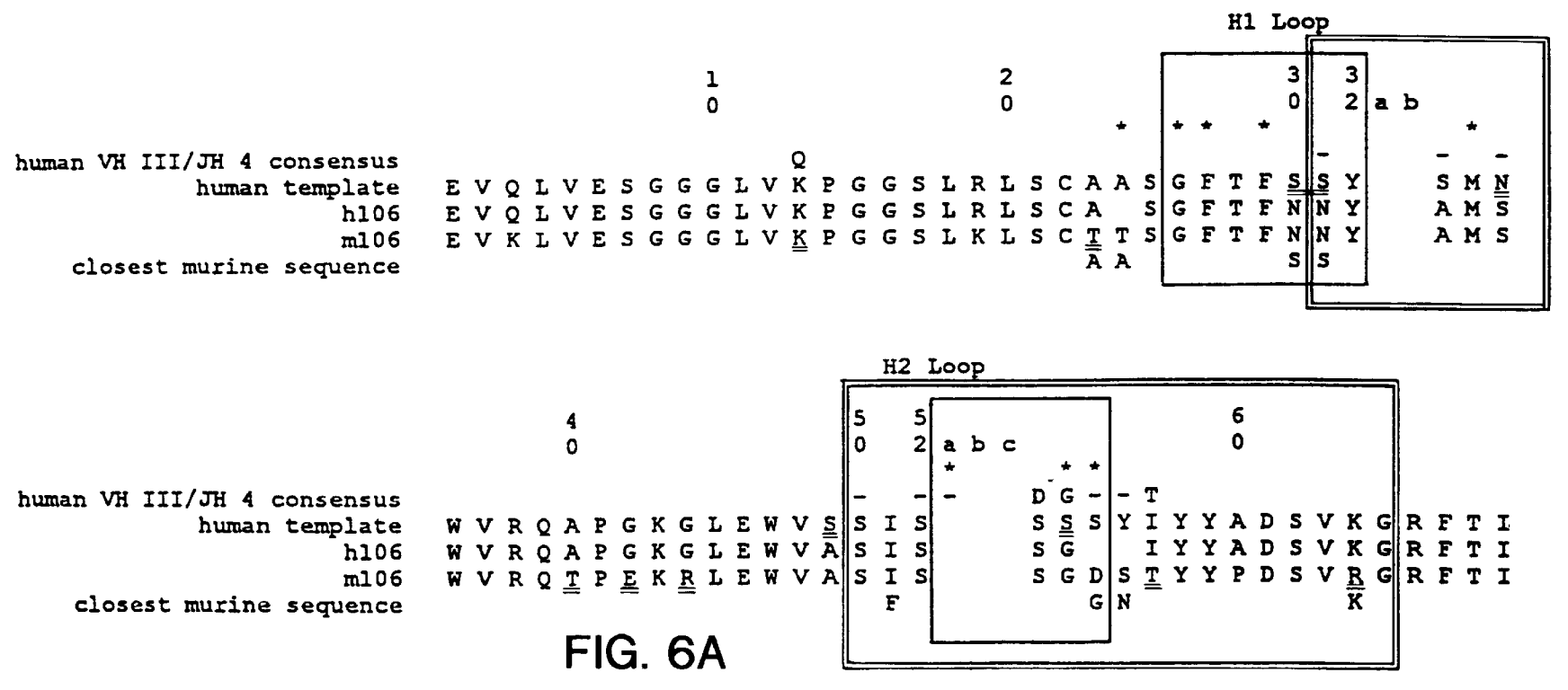
Figure 6B:
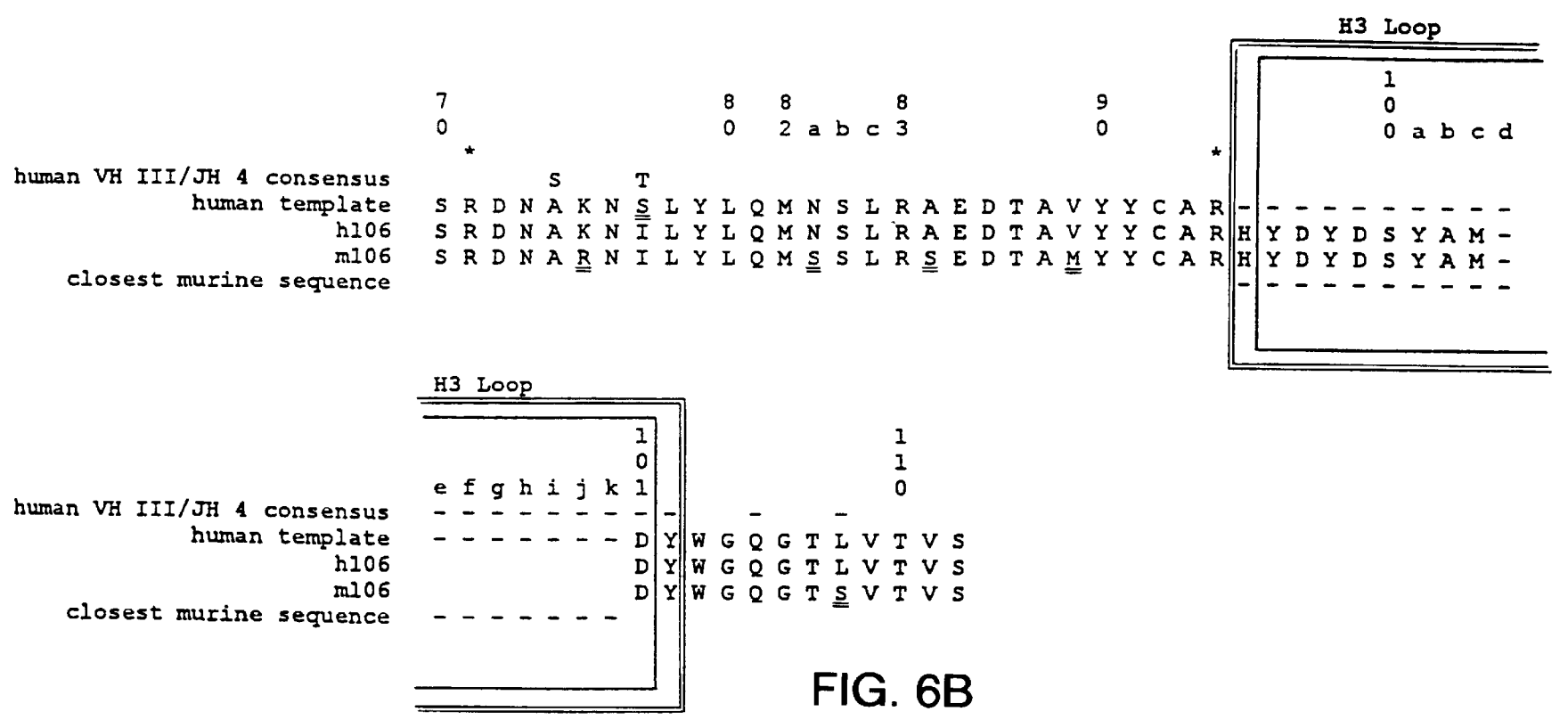

The murine nucleotide sequence with the closest homology to 106 VH was also determined by performing a FASTA search of the IgGe data set using only nucleotides encoding the mature peptide as the query sequence. The search resulted in locating two murine sequences followed by many human sequences. The murine sequences designated "Musighin" (Accession No. M21520) showed significantly better homology than the other murine sequence. The GenBank annotation for M21520 lists it as a rearranged sequence. For the purpose of finding probable sites of somatic mutation, M21520 was used as a germline substitute and differences between it and 106 VH are shown in the bottom set of lines in FIG. 6.

The human germline amino acid sequence with the closest homology to 106 VH was determined by performing a FASTA search on the IgP data set. After discarding the rearranged sequences, the best match was found with the "Hhg4" germline sequence (Accession No. X62129). It was noted that the size of the CDR loops was preserved between 106 VH and the human template and that all but two of the structural determinants for the CDR loops were conserved. None of the other highly homologous sequences gave a better fit in the structural determinants. The H1 loops of the murine sequence and the human template were also found to belong to the same canonical structure class. Three positions were identified that appear to be the sites of high levels of diversity (Ala24, Asp55 and Ser56). These residues are probably important for maintaining antigen binding, and it is difficult to tell from the sequence alignments whether human residues could be substituted for murine residues at these positions.

B. Refinement of 106 VL and VH Humanization Templates.

The canonical loop structures for the antigen binding loops L1, L2 and L3 of the VL domain and H1 and H2 of the VH domain were identified, and conserved residues that were defined as structural determinants (Chothia and Lesk, 1987. J. Mol. Biol. 196:901; Lesk and Tramontano, In Antibody Engineering, W. H. Freeman and Co., pp 1–38 (1992)) were retained as murine residues.

The refined VL and VH humanization templates were used to search the Brookhaven databank for homologous sequences in which the crystal structure had been solved. The VL from the anti-lysozyme binding monoclonal antibody D1.3 was selected as a structural template for modeling of the 106 VL. The VH from the anti-peptide monoclonal antibody 17/9 was chosen as a structural template for modeling of the 106 VH. These structures were combined to provide a composite template for 106 modeling using the set of invariant residues at the VL-VH interface. From the model, three additional framework residues which appeared to be important for maintaining the structure of the antigen binding sites were identified. In the VL, Ile48 was found to be structurally important and was retained as murine sequence. In the VH, two residues (Ala49 and Ile77) were also retained as murine sequence. The 106 model was not determinative of whether a human or murine residue was appropriate at positions 24, 55 and 56 of 106 VH.

C. Determination of the J-region Templates

The best human Jκ sequence was selected by homology to the murine Jκ sequence in Kabat et al. (Sequences of Proteins of Immunological Interest, 4th Edition, U.S. Health and Human Services, Washington, D.C. (1987)). Similarly, the best human JH sequence was selected by homology to the murine JH sequence in Kabat et al., supra.

D. Humanization of the 106 VL

The oligonucleotide primers used to humanize the 106 VL are listed in Table 8. The first three changes (Ala at position 9 to Ser, Glu at position 17 to Asp, and Thr at position 18 to Arg) were encoded on the Hu 106VLAre2 sense PCR primer. A HindIII site was added immediately 5' of the sequence encoding the mature VL for cloning the final humanized VL into pUC19. The next four changes were encoded in the Hu106VLB2 antisense PCR primer (Gln at position 40 to Pro, Arg at position 42 to Lys, Ser at position 43 to Ala, and Gln at position 45 to Lys). Using Hu106VLAre2 and Hu106VLB2 with murine 106 sFv-Ig/CDM8 as template, the first humanized fragment was obtained by PCR. The sense PCR primer Hu106VLC and the antisense PCR primer 2Hu106VLD were used to humanize the second fragment. The sequence of Hu106VLC overlapped Hu106VLB2 such that the same four changes were encoded on Hu106VLC (Gln at position 40 to Pro, Arg at position 42 to Lys, Ser at position 43 to Ala, and Gln at position 45 to Lys). In addition, an SpeI site was engineered into Hu106VLC as a diagnostic site. This change did not alter the protein sequence. The 2Hu106VLD primer encoded the next four changes (Gln at position 70 to Asp, Ser at position 72 to Thr, Lys at position 74 to Thr, and Asn at position 76 to Ser). Using Hu106VLC and 2Hu106VLD with murine 106 sFv-Ig/CDM8 as template, the second humanized fragment was obtained by PCR.

TABLE 8

Primers Used for 106 VL Humanization

| | | |
|---|---|---|
| | | HindIII |
| Hu106VLAre2 96-mer sense | 5'- | ATCGTCTAG<u>AAGCTT</u>GTCGACATCCAGATGACTCAGTCTCC ATCATCCCTATCTGCATCTGTGGGAGATCGAGTCACCATCA CATGTCGAGCAAGT - 3', SEQ ID. #33 |
| Hu106VLB2 45-mer antisense | 5'- | TAGTAGCTTAGGTGCCTTTCCAGGTTTCTGCTGATACCAAG CTAA - 3', SEQ ID. #34 |
| | | SpeI |
| Hu106VLC 60-mer antisense | 5'- | CCTGGAAAGGCACCTAAGCT<u>ACTAGT</u>CTATAATGCAAAAAC CTTAGCAAAAACCTTAGCA - 3', SEQ ID. #35 |
| 2Hu106VLD 45-mer antisense | 5'- | GAGATCGTCAGTGTAAAGTCTGTGCCTGATCCACTGCCACT GAAC - 3', SEQ ID. #36 |
| Hu106VLE 75-mer sense | 5'- | GACTTTACACTGACGATCTCAAGCCTGCAGCCTGAAGATTT TGCAACTTATTACTGTCAACATCATTATAATACT - 3', SEQ ID. #37 |
| | | XbaI |
| Hu106VLF 82-mer anti-sense | 5-' | TCAGTGCTT<u>CTAGA</u>GCCACCCCGTTTGATCTCGACCTTGGT CCCTCCACCGAACGTGAGCGGAGTATTATAATGATGTTGAC SEQ ID. #38 |
| Hu106VLA2 24-mer sense | 5'- | ATCGTCTAGAAGCTTGTCGACATC - 3', SEQ ID. #39 |
| HU106VLF2 24-mer anti-sense | 5'- | TCAGTGCTTCTAGAGCCACCCCGT - 3', SEQ ID. #40 |

The final humanized VL fragment was obtained using the Hu106VLE sense PCR primer and Hu106VLF antisense PCR primer with murine 106 sFv-Ig/CDM8 as template. Hu106VLE partially overlapped 2Hu106VLD such that it encoded the same four changes (Gln at position 70 to Asp, Ser at position 72 to Thr, Lys at position 74 to Thr, and Asn at position 76 to Ser). Additionally, Hu106VLe encoded two additional changes (Gly at position 84 to Ala and Ser at position 85 to Thr). Hu106VLF encoded the last four changes (Thr at position 100 to Gly, Leu at position 104 to Val, and Leu at position 106 to Ile). Hu106VLE also encoded an XbaI site immediately 3' of the VL sequence for cloning purposes. Humanized fragments 2 and 3 were then assembled and amplified by PCR by mixing the two humanized DNAs together in the presence of Hu106VLC sense primer and Hu106VLF antisense primer. This piece was purified, mixed with humanized fragment 1 and reamplified by PCR in the presence of the sense primer Hu106VLA2 and the antisense primer Hu106VLF2 such that a single PCR fragment was obtained. The amplified humanized 106 VL was then cut with HindIII and XbaI and ligated into pUC19. E. coli (strain DH50α) were transformed as usual and plasmid DNA from individual clones was sequenced to verify proper fragment assembly of the humanized 106 VL.

E. Humanization of the 106 VH

Figure 7:
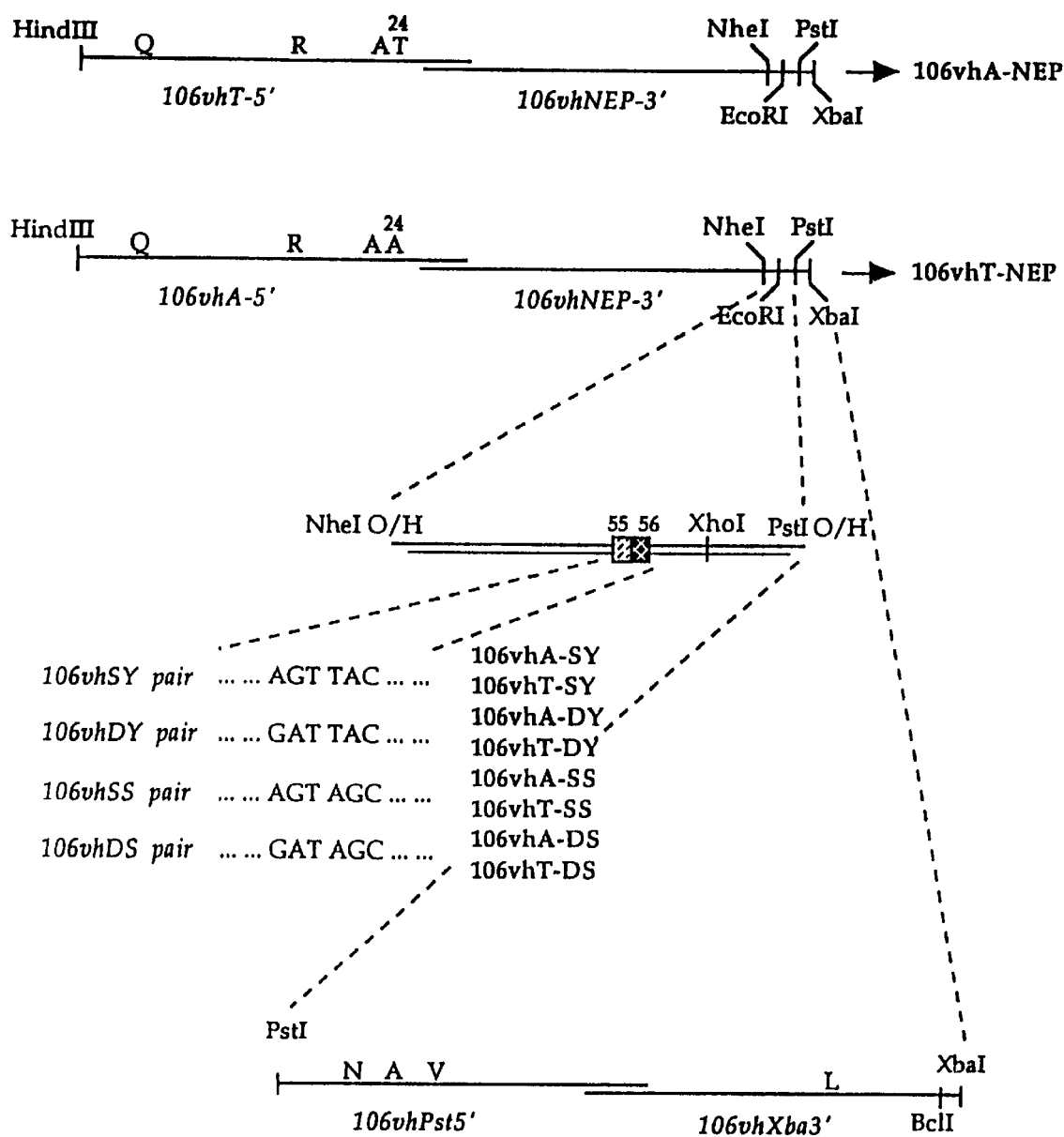
FIG. 7 depicts the assembly of the eight humanized 106 VH. Two DNA fragments were amplified by PCR of the first 149 bases of the murine 106 VH using sense primers that encoded a HindIII site immediately prior to 106 VH sequence containing changes of three (106 vh T-5') or four (106 vhA-5') of the murine residues to human residues, and an antisense primer that encoded unique restriction sites (NheI, EcoRI, PstI and XbaI). These fragments were digested with HindIII and XbaI and were ligated into pUC19, creating the two vectors 106 vhA-NEP and 106 vhT-NEP. Three pairs of synthesized oligonucleotides encoded changes at one or two positions (106 vh SY, 106 vh DY, 106 vh SS) while 106 vh DS maintained the original murine sequence at residues 55 and 56. All four pairs also encoded additional humanized residues of Ile57, Ala60, Lys64 and Lys75 which are not illustrated for simplicity. In addition, they were engineered with NheI and PstI overhangs (O/H) and a unique XhoI site for diagnostic digests. The DNA fragments generated by these oligonucleotides were ligated into the 106 vhA-NEP and 106 vhT-NEP vectors at the NheI and PstI sites. A final PCR fragment was generated using the 106 vh Pst5' sense primer and the 106 vh Xba3' antisense primer. These two oligonucleotides encoded four more changes from murine to human sequence. The DNA fragment was cloned into the previous constructs using PstI and XbaI restriction sites.

The strategy used to humanize the 106 VH was more complicated than the VL. Eight different versions of the VH were needed to accommodate the three amino acid residues where it was unclear whether human or mouse sequence was preferred (murine Thr or human Ala at position 24, murine Asp or human Ser at position 55, and murine Ser or human Tyr at position 56). Since the second and third residues in question were contiguous, it seemed logical to encode them on oligonucleotide fragments that could be synthesized and inserted into unique restriction sites instead of assembling each as a separate set of PCR fragments generated using humanized oligonucleotides. However, suitable restriction sites were not available in the nucleotide sequence encoding 106 VH. Therefore, a unique NheI site was introduced at position 146 in the nucleotide sequence and a unique PstI site was introduced at position 238. These sites are not found in pUC19. Also, the changes did not affect the protein sequence of 106 VH. Two pUC19-based vectors could then be assembled that contained sequence encoding Thr or Ala at position 24 and that contained NheI and PstI sites for insertion of the four fragments. The oligonucleotide primers used to humanize the 106 VH are shown in Table 9. Each fragment was assembled from a pair of synthesized oligonucleotides containing sequence that encoded NheI and PstI overhangs when annealed, and which encoded one of the Asp-Ser, Asp-Tyr, Ser-Ser, or Ser-Tyr combinations. A unique XhoI site for diagnostic purposes was also engineered into the oligonucleotides encoding these fragments. The XhoI site did not alter the protein sequence of 106 VH. After incorporation of the fragments into the two vectors (generating eight constructs), a final PCR fragment could be inserted into each using the PstI site and a unique XbaI site that was engineered into the sequence. This PstI-XbaI fragment contained sequence encoding the remaining humanized residues for 106 VH (FIG. 7).

TABLE 9

Primers Used for 106 VH Humanization

106vhT-5'  106-mer sense
HindIII
5'- ATCGTCTAGAAGCTTGAAGTGCAGCTGGTGGAGTCTGGAGG AGGCTTAGTGAAGCCTGGAGGGTCCCTGAGGCTCTCCTGTG CAACCTCTGGATTCACTTTCAATA - 3'  SEQ ID. #41

106VHA-5'  106-mer sense
HindIII
5'- ATCGTCTAGAAGCTTGAAGTGCAGCTGGTGGAGTCTGGAGG AGGCTTAGTGAAGCCTGGAGGGTCCCTGAGGCTCTCCTGTG CAGCCTCTGGATTCACTTTCAATA - 3'  SEQ ID. #42

106vbNEP-3'  87-mer anti-sense
XbaI        PstI        EcoRI        NheI
5'- TCAGTGCTCTAGAACCCTGCAGATCGAATTCAATGCTAGCG ACCCACTCCAGTCCCTTACCTGGTGCCTGGCGAACCCAAGA CATGG - 3'  SEQ ID. #43

106vhSY-5'  97-mer sense
NheI
5'- CTAGCATTAGTAGTGGTAGTTACATCTACTATGCTGACAGT GTGAAAGGCCGATTCACCATCTCGAGAGATAATGCCAAAAA CATCCTGTATCTGCA - 3'    XhoI    SEQ ID. #44
PstI 106vhSY-3'  89-mer anti-sense
XhoI
5'- GATACAGGATGTTTTTGGCATTATCTCTCGAGATGGTGAAT CGGCCTTTCACACTGTCAGCATAGTAGATGTAACTACCACT ACTAATG - 3'  SEQ ID. #45

106vhDY-5'  97-mer sense
NheI
5'- CTAGCATTAGTAGTGGTGATTACATCTACTATGCTGACAGT GTGAAAGGCCGATTCACCATCTCGAGAGATAATGCCAAAAA CATCCTGTATCTGCA - 3'  XhoI    SEQ ID. #46
PstI 106vhDY-3'  89-mer anti-sense
XhoI
5'- GATACAGGATGTTTTTGGCATTATCTCTCGAGATGGTGAAT CGGCCTTTCACACTGTCAGCATAGTAGATGTAATCACCACT ACTAATG - 3'  SEQ ID#47

106vhSS-5'  97-mer sense
NheI
5'- CTAGCATTAGTAGTGGTAGTAGCATCTACTATGCTGACAGT GTGAAAGGCCGATTCACCATCTCGAGAGATAATGCCAAAAA CATCCTGTATCTGCA - 3',      XhoI    SEQ ID. #48
PstI 106vhSS-3'  89-mer anti-sense
XhoI
5'- GATACAGGATGTTTTTGGCATTATCTCTCGAGATGGTGAAT CGGCCTTTCACACTGTCAGCATAGTAGATGCTACTACCACT ACTAATG - 3'  SEQ ID. #49

106vhDS-5'  97-mer sense
NheI
5'- CTAGCATTAGTAGTGGTGATAGCATCTACTATGCTGACAGT GTGAAAGGCCGATTCACCATCTCGAGAGATAATGCCAAAAA CATCCTGTATCTGCA - 3'    XhoI    SEQ ID. #50
PstI 106vhDS-3'  89-mer anti-sense
XhoI
5'- GATACAGGATGTTTTTGGCATTATCTCTCGAGATGGTGAAT CGGCCTTTCACACTGTCAGCATAGTAGATGCTATCACCACT ACTAATG-3'  SEQ ID. #51

106vhPst5'  78-mer sense
PstI
5'- ATCGTCTAGCTGCAGATGAACAGTCTGAGGGCAGAGGACAC GGCCGTCTATTACTGTGCAAGGCACTATGATTACGAC - 3' SEQ ID. #52

106vhXb3'
XbaI        BclI
5'- TCAGTGCTCTAGATGATCAGAGGAGACGGTGACCAGGGTTC

TABLE 9-continued

Primers Used for 106 VH Humanization

| | | |
|---|---|---|
| 69-mer anti-sense | CTTGACCCCAGTAGTCCATAGCATAGCT- 3' | SEQ ID. #53 |

In greater detail, construction of the two vectors was initiated by generating two PCR fragments using 106sFv-Ig/CDM8 as template and either 106vhT-5' or 106vhA-5' as the sense primer and 106vhNEP-3' as the antisense primer. The sense primers encoded a HindIII site immediately 5' of the VH and the first three humanized VH changes (Lys at position 3 to Gln, Lys at position 19 to Arg, and Thr at position 23 to Ala). In addition, the 106vhA-5' sense primer humanized the residue at position 24 to Ala whereas the 106vhT-5' sense primer kept the residue as murine (Thr). The antisense primer encoded changes at residues 40, 42 and 44 (Thr to Ala, Glu to Gly and Arg to Gly, respectively) and also encoded four unique restriction sites (NheI, EcoRI, PstI, and XbaI). The two PCR'ed DNAs were then cloned into pUC19 as HindIII-XbaI fragments and were used to transform DH5α *E. coli*. Clones containing both inserts were isolated (106vhA-NEP and 106vhT-NEP) and verified by DNA sequencing. The plasmids were then digested with NheI, EcoRI and PstI and linear DNA was isolated and purified.

The sense oligonucleotide in each of the four pairs of oligonucleotides that encoded the changes at positions 55 and 56 were phosphorylated and annealed to the corresponding antisense oligonucleotide. This generated dsDNA fragments that had a 5' NheI overhang and a 3' PstI overhang, and that contained a unique XhoI site. The primer pair 106vhDS-5' and 106vhDS-3' encoded murine residues at positions 55 and 56 (Asp-Ser); 106vhDY-5' and 106vhDY-3' encoded murine and human residues at positions 55 and 56, respectively (Asp-Tyr); 106vhSS-5' and 106vhSS-3' encoded human and mouse residues at positions 55 and 56, respectively (Ser-Ser); and 106vhSY-5' and 106vhSY-3' encoded human residues at positions 55 and 56 (Ser-Tyr). All of the primer pairs also encoded four additional changes from murine to human sequence (Thr to Ile at position 57, Pro to Ala at position 60, Arg to Lys at position 64 and Arg to Lys at position 75). The four fragments that were generated were then ligated into 106vhA-NEP/pUC 19 and 106vhT-NEP/pUC 19. The plasmids is were used to transform DH5α *E. coli* and DNA from clones that cut with XhoI were isolated and verified by DNA sequencing. Of the eight combinations, seven were obtained (106vhA-DS, representing human, mouse, mouse sequence at positions 24, 55 and 56, was never isolated from pUC19). The seven plasmids were digested with PstI and XbaI and were now ready to receive the final fragment.

The remaining residues that were changed to human sequence were encoded on sense primer 106vhPst5' (Ser to Asn at position 82a, Ser to Ala at position 84, and Met to Val at position 89) and antisense primer 106vhPst3' (Ser to Leu at position 108). For cloning purposes, primer 106vhPst5' also encoded a PstI site and 106vhPst3' encoded an XbaI site with a BclI site immediately preceding it. This fragment was obtained by PCR using 106sFv-Ig/CDM8 as template. The fragment was digested with PstI and XbaI and was ligated into the seven plasmids. Once again, the plasmids were used to transform DH5α *E. coli* and DNA from clones was sequenced to verify insertion.

F. Assembly of Humanized 106 sFv Gene Cassettes

The humanized single chain Fv expression cassettes for 106 were assembled as for the original murine 106 sFv but using the following primers:

TABLE 10

Primers Used for Construction of Humanized 106 sFv Gene Cassettes

| | | |
|---|---|---|
| hu106V$_L$SalI 45-mer sense | 5'- | SalI<br>ATCGTCTAGGTCGACATCCAGATGACTCAGTCTCCA TCATCC - 3'   SEQ ID. #54 |
| hu106V$_L$LK3' 60-mer anti-sense | 5'- | GCCACCCGACCCACCACCGCCAGCGCCACCGCCACC CCGTTTGATCTCGACCTTGGTCCC - 3'   SEQ ID. #55 |
| hu106V$_H$LK5' 60-mer sense | 5'- | TCGGGCGGTGGTGGGTCGGGTGGCGGCGGATCTGAA GTGCAGCTGGTGGAGTCTGGAGGA - 3'   SEQ ID. #56 |
| hu106V$_H$BclI 45-mer anti-sense | 5'- | BclI<br>TCAGTGCTGATCAGAGGAGACGGTGACCAGGGTTCC TTGACC - 3'   SEQ ID. #57 |

Briefly, DNA encoding the humanized 106 VL was cut from the pUC19 vector in which it was assembled. DNA encoding the seven humanized 106 VH were also cut from pUC19. The DNA fragments were purified and used in the following PCR reactions. The humanized 106 VL was amplified using the hu106V$_L$SalI sense PCR primer that encoded a SalI site immediately prior to the first residue of the mature VL and an antisense primer (hu106V$_L$LK3') that was complementary to sequence encoding the last nine residues of the VL and the first 12 residues of the (Gly4Ser)$_3$ linker. Additionally, the seven humanized 106 VH were amplified using a sense primer (hu106VHLK5') encoding the first 11 residues of the (Gly4Ser)3 linker followed by the first nine residues of the mature VH and an antisense primer (hu106V$_H$BclI) complementary to sequence encoding the last nine residues of the VH region and a BclI site. The modified 106 VL was mixed with each of the modified 106 VH DNA in the presence of excess VL sense primer (hu106V$_L$SalI 5') and VH antisense primer (hu106V$_H$BclI)

so that the individual humanized 106 VL was linked with each of the individual humanized 106 VH into seven VL-link-VH single coding regions by overlap extension PCR.

The humanized 106 VL-link-VH sFv gene cassettes were then assembled for sFv-Ig expression in the pUC-Ig vector. This vector contains the L6 VK leader sequence followed by a SalI site and a BclI site preceding sequence encoding the hinge-CH2-CH3 of human IgGI and a stop codon flanked by an XbaI site. The hinge cysteines were mutated to serines to favor monomeric expression of sFv-Ig fission protein. The humanized 106 VL-link-VH sFv gene cassettes were cut with SaiII and BclI and were ligated into pUC-Ig. DH5α $E. coli$ were transformed with the constructs and colonies were screened for inserts. Six of the seven VH constructs were properly inserted into pUC-Ig. The entire L6 VK leader/humanized 106 VL-link-VH sFv/human Ig cassettes were cut from pUC-Ig using HindIII and XbaI and were transferred to the pCDM8 mammalian expression vector and were amplified by transformation in $E. Coli$ strain MC1061/p3. Of the six, five were inserted properly into pCDM8. DNA was recovered from each for COS cell transfections.

Small-scale COS cell transfections were carried out in 60 mm tissue culture plates by the DEAE-dextran method. Three ml of transfection supernatant was recovered from each after three days of culture and were tested for the presence of soluble sFv-Ig fusion protein by Western blot and ELISA. In addition, an anti-human Ig sandwich ELISA was performed to quantify the amount of protein expressed by each construct and the on-rates of the different proteins binding to gp39 were measured by Biacore analysis.

G. Preliminary Analysis of Humanized 106 sFv Expressed by Transient Transfection in COS Cells.

SDS-PAGE and Western blot of the transfection supernatants showed that of the five constructs used to transfect COS cells (humanized 106 sFv containing the 106 VH fragments 106vhT-DS, 106vhT-SS, 106vhT-SY, 106vhA-DY and 106vhA-SY), four secreted protein into the supernatant. There was no protein expressed by humanized 106 sFv containing 106vhT-SY (huVL/106vhT-SY). Of the four expressors, three expressed protein of correct size for an sfv-Ig fusion protein (55 kDa). HuVL/106vhT-SS produced a protein of aberrant size (approximately 97 kDa). Expression levels for HuVL/106vhT-DS appeared to be similar to murine 106 sFv while HuVL/106vhA-DY and HuVL/106vhA-SY expressed at lower levels.

The protein levels were quantified using a sandwich ELISA to detect the human Ig tail. ELISA plates were coated with goat anti-human Ig in PBS and blocked in PBS +0.1% BSA. The transfection supernatants were incubated neat and at a 1:5 dilution for 1 hr at RT. The plates were then washed and incubated with goat anti-human Ig-horseradish peroxidase in ELISA conjugate buffer for 1 hr at RT. Plates were washed again and a 1:100 dilution of tetramethylbenzidine in citrate buffer was added. The color reaction was stopped with 3M $H_2SO_4$ and the optical density was measured at 450–595 nm with a Titertek multiwell plate reader. Approximate protein concentrations were determined by comparison to a known concentration of CD4ORγ1 (CD40-Ig) that had been determined with the Bio-Rad protein concentration kit. The protein concentrations were:

huVL/106vhA-DY (clone 10) 0.62 μg/ml huVL/106vhA-DY (clone 12) 0.82 μg/ml huVL/106vhA-SY (clone 21) 0.77 μg/ml huVL/106vhT-SY (clone 26) 0 μg/ml huVL/106vhT-SS (clone 36) 0.15 μg/ml huVL/106vhT-DS (clone 46) 1.20 μg/ml The supernatants were tested for their ability to block E-selectin expression on endothelial cells. Human umbilical vein endothelial cells (HUVECs, Clonetics Corporation) were cultured and stimulated in M199 (Medium 199, Gibco BRL) with additions to final concentrations as follows: 4 mM L-glutarnine, 48.5 μg/ml penicillin, 80 μg/ml streptomycin, 1 mM sodium pyruvate (Sigma), 90 μg/ml heparin (Sigma), 30 μg/ml endothelial growth supplement (Collaborative Biomedical Products) and 20% fetal bovine serum. Endothelial cells were grown in tissue culture flasks treated with 1% gelatin, and plated at $1.5 \times 10^4$ cells/well in flat-bottomed 96-well Costar tissue culture plates that had been coated with 1 μg/well fibronectin (Collaborative Biomedical Products). Endothelial cells were stimulated 1–2 days after plating. Cells were used at passage 4 or 5. sgp39 and supernatants containing humanized 106 sFv-Igs were added in M199 plus additions in 100 μl per well and incubated at 37° C. for 4 hours prior to assaying for E-selectin expression. Plates were then washed twice with cold PBS, fixed for 10 minutes with 0.5% glutaraldehyde in PBS at 4° C., washed four times with 3% goat serum/PBS/20 mM EDTA (blocking buffer) and blocked 1 hour at 37° C. or overnight at 4° C. in the same buffer. Cells were treated with 100 μl anti-E- and P-selectin (R&D Systems) at 0.25 μg/ml in blocking buffer for 1 hour at 37° C. Plates were washed four times with blocking buffer, incubated 1 hour at 37° C. with horseradish peroxidase conjugated anti-mouse IgG in blocking buffer (Jackson ImmunoResearch, 100 μl/well, 1:2000 dilution) then washed four times. Plates were developed using EIA chromagen reagent in EIA buffered substrate (both from Genetic Systems, 100 μl/well, 1:100 dilution) and stopped with 100 μl per well of 1N $H_2SO_4$. The absorbance was determined at dual wave lengths of 450 nm and 630 nm.

Figure 8:
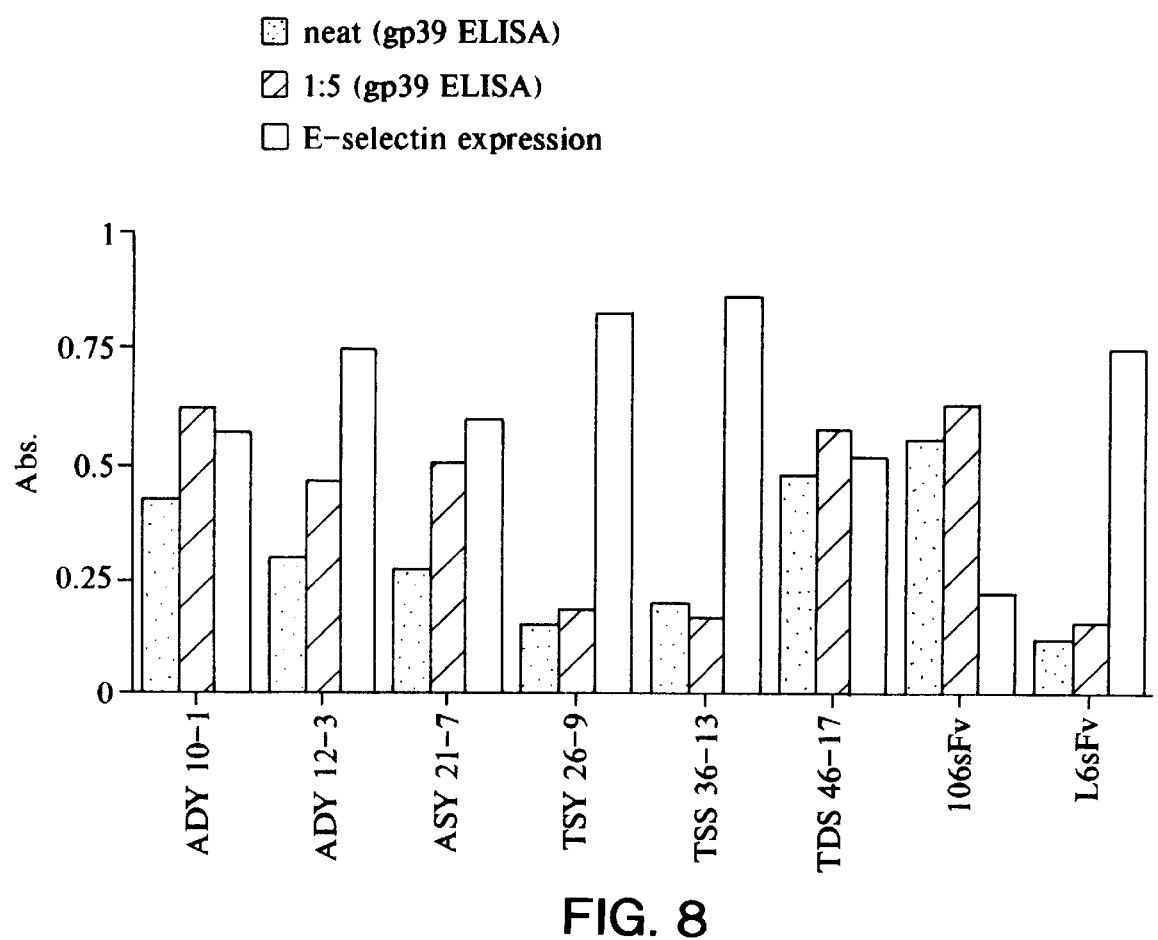
FIG. 8 demonstrates the inhibition of E-selectin expression on endothelial cells. The black bars show expression levels of E-selectin. While the murine 106 sFv-Ig shows strong inhibition, the L6 sFv-Ig negative control shows no inhibition. HuVL/106 vhA-DY ("ADY"), huVL/106 vhA-SY ("ASY") and hu VL/106 vhT-DS ("TDS") inhibit E-selectin expression, although not as effectively as the murine 106 sFv-Ig. Supernatants from the hu VL/106vhT-SY ("TSY"; no protein) and huVL/106vhT-SS ("TSS"; aberrant protein) transfections did not show any activity.

HuVL/106vhA-DY, huVL/106vhA-SY and huVL/106vhT-DS all inhibited E-selectin 0expression although not as effectively as the original murine 106 sFv-Ig (FIG. 8). Differences may be accounted for by lower protein expression in huVL/106vhA-DY and huVL/106vhA-SY, although huVL/106vhT-DS appeared to express at levels comparable to the original murine 106 sFv-Ig.

Figure 9:
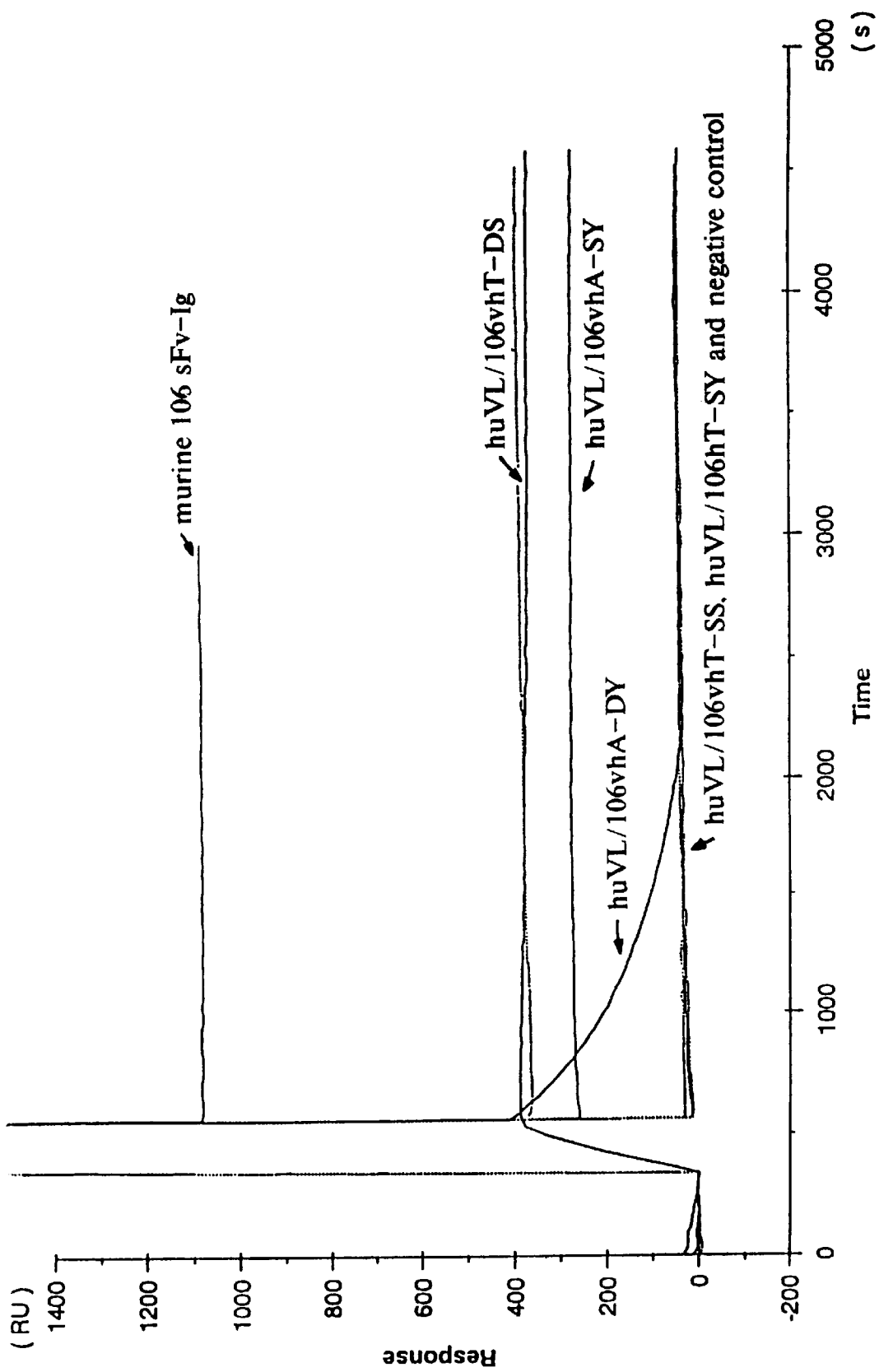
FIG. 9 depicts the Biacore™ analysis of humanized 106 sFv-Ig proteins binding to human gp39. Human gp39 was coated on chips and the various humanized 106 sFv-Ig transfection supernatants were tested for binding. The original murine 106 sFv-Ig bound very tightly (no off-rate observed, as shown by horizontal line). Proteins from the huVL/106vhA-DY ("ADY12-3"), huVL/106vhA-SY ("ASY21-7") and huVL/106vhT-DS (TDS46-17") transfection supernatants also bound tightly with no detectable off-rate. Supernatants from the huVL/106vhT-SY ("TSY26-9"; no protein) and huVL/106vhT-SS ("TSS36-13"; aberrant protein) transfections did not bind to gp39-coated chips.

The on-rates of the different proteins binding to gp39 were determined using the Biacore. HuVL/106vhA-SY and huVL/106vhT-DS both bound tightly to chips coated with gp39, with activity comparable to the original murine 106 sFv-Ig (FIG. 9). Since these proteins did not come off, it was unclear whether the affinities of these sFv-Ig were very high (the profiles indicated affinities of Kd $\sim 10^{-1}$M or greater) or whether the proteins were aggregated and were binding multivalently. HuVL/106vhA-DY did come off. From its profile, affinity was estimated to be approximately Kd=$10^{-7}$ to $10^{-8}$M. The original murine 106 sFv-Ig had been measured at Kd=$1.6 \times 10^{-9}$M so it appears that huVL/106vhA-SY and huVL/106vhT-DS are high affinity humanized anti-gp39 sFv.

HuVL/106vhA-SY and huVL/106vhT-DS were found to bind tightly to human gp39 and show functional activity in inhibiting E-selectin expression on endothelial cells. Although huVL/106vhA-SY appears to express at lower levels than huVL/106vhT-DS, it is the "most human" of the humanized 106 sFv.

Cell Line Deposits

The following hybridoma cell lines were deposited with the American Type Culture Collection, 10801 University Boulevard, Manassas Va. 20110, USA.

| Hybridoma | ATCC Designation |
|---|---|
| 39-1.29 | HB 11808 |
| 39-1.132 | HB 11809 |
| 39-1.134 | HB 11810 |
| 39-1.106 | HB 11811 |
| 39-1.7 | HB 11812 |
| 39-1.37 | HB 11813 |
| 39-1.77 | HB 11814 |
| 39-1.59 | HB 11815 |
| 39-1.122 | HB 11816 |
| 39-1.156 | HB 11817 |
| 39-1.128 | HB 11818 |
| 39-1.124 | HB 11819 |

-continued

| Hybridoma | ATCC Designation |
|---|---|
| 39-1.26 | HB 11820 |
| 39-1.138 | HB 11821 |
| 39-1.3 | HB 11822 |
| 39-7.3E12 | HB 11823 |

We claim:

1. A monoclonal antibody, an antigen binding fragment or recombinant binding protein thereof, which is specific for human gp39 and, (a) binds to a mutant form of human gp39 and wild-type gp39 with a similar avidity wherein the mutant comprises tyrosine 145, asparagine 180, or phenylalanine 201 and glutamic acid 202 replaced by alanine; (b) has a poor binding avidity to a mutant gp39 as compared to the binding avidity to wild-type gp39 wherein the mutant form of gp39 comprises glutamic acid 129, or serine 131 and threonine 135 replaced by alanine; (c) binds weakly or with somewhat reduced avidity to a mutant gp39 as compared to the binding avidity to wild-type gp39 wherein the mutant form of gp 39 comprises lysine 143, and (d) does not react with gp39 by Western blot.

2. The monoclonal antibody of claim 1, wherein the antibody is that secreted by the hybridoma 39-1.3 designated ATCC HB 11822, 39-1.122 designated ATCC HB 11816, or 39-1.138 designated ATCC HB 11821.

3. The antigen binding fragment of claim 1, wherein the fragment is derived from the antibody secreted by the hybridoma 39-1.3 designated ATCC HB 11822, 39-1.122 designated ATCC HB 11816,or 39-1.138 designated ATCC HB 11821.

4. The antigen binding fragment of claim 3, wherein the fragment is a Fab, F(ab')$_2$, or Fv.

5. The recombinant binding protein of claim 1, wherein the protein is an sFv, a humanized antibody or a recombinant protein comprising a variable region of an antibody of claim 2.

6. A monoclonal antibody, an antigen binding fragment or recombinant binding protein thereof, which is specific for human gp39 and; (a) binds to a mutant form of human gp39 with a somewhat reduced avidity when compared to the binding avidity to wild-type gp39 wherein the mutant form of gp39 comprises tyrosine 145, asparagine 180 or phenylalanine 201 and glutamic acid 202 replaced by alanine; (b) has a poor binding avidity to a mutant gp39 compared to the binding avidity to wild-type gp39 wherein the mutant form of gp39 comprises glutamic acid 129, or serine 131 and threonine 135 replaced by alanine; (c) binds with weak avidity to a mutant gp39 as compared to the binding avidity to wild-type gp39 wherein the mutant form of gp 39 comprises lysine 143, and (d) does not react with gp39 by Western blot.

7. The monoclonal antibody of claim 6, wherein the antibody is that secreted by the hybridoma 39-1.59 designated ATCC HB 11815.

8. The antigen binding fragment of claim 7, wherein the fragment is derived from the antibody secreted by the hybridoma 39-1.59 designated ATCC HB 11815.

9. The antigen fragment of claim 8, wherein the fragment is a Fab, F(ab')$_2$, or Fv.

10. The recombinant binding protein of claim 6, wherein the protein is an sFv or a recombinant protein comprising a variable region of an antibody of claim 7.

11. A monoclonal antibody, an antigen binding fragment or recombinant binding protein thereof, which is specific for human gp39 and; (a) binds to a mutant form of human gp39 with a similar binding avidity when compared to the binding avidity to wild-type gp39, wherein the mutant form of gp39 comprises serine 131 and threonine 135, tyrosine 145, asparagine 180, or phenylalanine 201 and glutamic acid 202 replaced by alanine; (b) has a poor binding avidity to a mutant gp39 as compared to the binding avidity to wild-type gp39 wherein the mutant form of gp39 comprises glutamic acid 129, or lysine 143 replaced by alanine; and (c) does not react with gp39 by Western blot.

12. The monoclonal antibody of claim 11, wherein the antibody is that secreted by the hybridoma 39-1.37 designated ATCC HB 11813 or 39-1.132 designated ATCC HB 11809.

13. The antigen binding fragment of claim 11, wherein the fragment is derived from the antibody secreted by the hybridoma 39-1.37 designated ATCC HB 11813 or 39-1.132 designated ATCC HB 11809.

14. The antigen binding fragment of claim 11, wherein the fragment is a Fab, F(ab')$_2$, or Fv.

15. The recombinant binding protein of claim 11, wherein the protein is an sFv, a humanized antibody or a recombinant protein comprising a variable region of an antibody of claim 12.

16. A monoclonal antibody, an antigen binding fragment or recombinant binding protein thereof, which is specific for human gp39 and; (a) binds to a mutant form of human gp39 with a somewhat reduced binding avidity when compared to the binding avidity to wild-type gp39, wherein the mutant form of gp39 comprises serine 131 and threonine 135, or asparagine 180, (b) binds to a mutant form of human gp39 with a similar binding avidity when compared to wild-type gp39, wherein the mutant form of human gp39 comprises tyrosine 145, or phenylalanine 201 and glutamic acid 202 replaced by alanine; (c) has a poor binding avidity to a mutant gp39 compared to the binding avidity to wild-type gp39 wherein the mutant form of gp39 comprises glutamic acid 129, or lysine 143 replaced by alanine; and (d) reacts with gp39 by Western blot.

17. The monoclonal antibody of claim 16, wherein the antibody is that secreted by the hybridoma 39-1.124 designated ATCC HB 11819 or 39-1.156 designated ATCC HB 11817.

18. The antigen binding fragment of claim 16, wherein the fragment is derived from the antibody secreted by the hybridoma 39-1.124 designated ATCC HB 11819 or 39-1.156 designated ATCC HB 11817.

19. The antigen binding fragment of claim 18, wherein the fragment is a Fab, F(ab')$_2$, or Fv.

20. The recombinant binding protein of claim 16, wherein the protein is an sFv, humanized antibody or a recombinant protein comprising a variable region of an antibody of claim 17.

21. A monoclonal antibody secreted by the hybridoma 39-1.7 designated ATCC HB 11812, 39-1.128 designated ATCC HB 11818, or 39-1.26 designated ATCC HB 11820, or an antigen binding fragment or recombinant binding protein thereof.

22. The antigen binding fragment of claim 21, wherein the fragment is a Fab, F(ab')$_2$, or Fv.

23. The recombinant binding protein of claim 21, wherein the protein is an sFv, a humanized antibody or a recombinant binding protein comprising a variable region of an antibody of claim 21.

24. A monoclonal antibody, an antigen binding fragment or recombinant binding protein thereof, which is specific for human gp39 and which: (a) binds to a mutant form of gp39 and to wild-type gp39 with a similar binding avidity, wherein the mutant form of gp39 comprises glutamic acid 129, serine 131 and threonine 135, tyrosine 145, or asparagine 180 replaced by alanine; (b) has a poor binding avidity to mutant gp39 when compared to the binding avidity to wild-type gp39 wherein the mutant form of gp39 comprises phenylalanine 201 and glutamic acid 202 replaced by alanine; (c) has a somewhat reduced binding avidity to mutant gp39 when compared to the binding avidity to wild-type gp39, wherein the mutant form of gp39 comprises lysine 143 replaced by alanine; and (d) binds to gp39 by Western blot.

25. The monoclonal antibody of claim 24, wherein the antibody is that secreted by the hybridoma 39-1.77 designated ATCC HB 11814, 39-1.106 designated ATCC HB 11811, or 39-1.134 designated ATCC HB 11810.

26. The antigen binding fragment of claim 24, wherein the fragment is derived from the antibody secreted by the hybridoma 39-1.77 designated ATCC HB 11814, 39-1.106 designated ATCC HB 11811, or 39-1.134 designated ATCC HB 11810.

27. The antigen binding fragment of claim 24, wherein the fragment is a Fab, F(ab')$_2$, or Fv.

28. The recombinant binding protein of claim 24, herein the protein is an sFv, a humanized antibody or a recombinant protein comprising a variable region of an antibody of claim 27.

29. A monoclonal antibody, an antigen binding fragment or recombinant binding protein thereof, which is specific for human gp39 and; (a) binds to a mutant form of human gp39 and wild-type gp39 with a similar binding avidity, wherein the mutant form of gp39 comprises glutamic acid 129, serine 131 and threonine 135, lysine 143, tyrosine 145, or asparagine 180 replaced by alanine, (b) has poor binding avidity to mutant gp39 compared to the binding avidity to wild-type gp39 wherein the mutant form of gp39 comprises phenylalanine 201 and glutamic acid 202 replaced by alanine, (c) binds to gp39 by Western blot.

30. The monoclonal antibody of claim 29, wherein the antibody is that secreted by the hybridoma 39-1.29 designated ATCC HB 11808.

31. The antigen binding fragment of claim 29, wherein the fragment is derived from the antibody secreted by the hybridoma 39-1.29 designated ATCC HB 11808.

32. The antigen binding fragment of claim 31, wherein the fragment is a Fab, F(ab')$_2$, or Fv.

33. The recombinant binding protein of claim 29, wherein the protein is an sFv, a humanized antibody or a recombinant protein comprising a variable region of the antibody produced by the hybridoma 39-1.29 designated ATCC HB 11808.

34. A monoclonal antibody, an antigen binding fragment or recombinant binding protein thereof, which is specific for human gp39 and; (a) binds to a mutant form of human gp39 and wild-type gp39 with a similar binding avidity, wherein the mutant form of gp39 comprises glutamic acid 129, serine 131 and threonine 135, tyrosine 145, or asparagine 180 replaced by alanine, (b) has somewhat reduced binding avidity to a mutant gp39 when compared to wild-type gp39 wherein the mutant comprises lysine 143 replaced by alanine, and (c) does not bind to gp39 by Western blot.

35. The monoclonal antibody of claim 34, wherein the antibody is that secreted by the hybridoma 39-7.3E12 designated ATCC HB 11823.

36. The antigen binding fragment of claim 34, wherein the fragment is derived from the antibody secreted by the hybridoma 39-7.3E12 designated ATCC HB 11823.

37. The antigen binding fragment of claim 36, wherein the fragment is a Fab, F(ab')$_2$, or Fv.

38. The recombinant binding protein of claim 36, wherein the protein is an sFv, a humanized antibody or a recombinant protein comprising a variable region of the antibody produced by the hybridoma 39-7.3E12 designated ATCC HB 11823.

39. A pharmaceutical composition comprising a monoclonal antibody, antigen binding fragment or recombinant binding fragment thereof of claim 1, 6, 11, 16, 21, 24, 29 or 34 and a pharmaceutically acceptable carrier.

40. A monoclonal antibody, an antigen binding fragment or recombinant binding protein thereof, wherein the antibody is reactive with human gp39, and wherein said antibody has a poor, weak, or somewhat reduced binding avidity to a mutant gp39 when compared to the binding avidity to wild-type gp39, wherein the mutant form of gp39 comprises the glutamic acid at position 129 replaced by an alanine.

41. The monoclonal antibody, antigen binding fragment or recombinant binding protein thereof of claim 40, wherein the antibody, binding fragment or recombinant binding protein is further characterized by the binding to gp39 by Western blot.

42. The monoclonal antibody, antigen binding fragment or recombinant binding protein thereof of claim 40, wherein the antibody, binding fragment or recombinant binding protein thereof is further characterized by the inability to recognize human gp39 by Western blot.

43. A monoclonal antibody, antigen binding fragment or recombinant binding protein thereof, wherein the antibody is reactive with human gp39, but is not highly reactive with a mutant of human gp39 wherein the serine at position 131 and the threonine at position 135 have been replaced by alanine.

44. The monoclonal antibody, antigen fragment or recombinant binding protein thereof of claim 43, wherein the antibody, antigen binding fragment or recombinant binding protein is further characterized by the inability to recognize human gp39 by Western blot.

45. A monoclonal antibody, antigen binding fragment or recombinant binding protein thereof, wherein the antibody, antigen binding fragment or recombinant binding protein is reactive with human gp39, and wherein said antibody has a somewhat reduced binding avidity to a mutant gp39 when compared to the binding avidity to wild-type gp39, wherein the mutant form of gp39 comprises the tyrosine at position 145 replaced by alanine.

46. The monoclonal antibody, antigen binding fragment or recombinant binding protein thereof of claim 45, wherein the antibody, antigen binding fragment or recombinant binding protein is further characterized by the inability to bind gp39 by Western blot.

47. A monoclonal antibody, antigen binding fragment or recombinant binding protein thereof, wherein the antibody, antigen binding fragment or recombinant binding protein is reactive with human gp39, but is not similarly reactive with a mutant of human gp39 wherein the asparagine at position 180 has been replaced by alanine.

48. The monoclonal antibody, antigen binding fragment or recombinant binding protein thereof of claim 47, wherein the antibody, antigen binding fragment or recombinant binding protein is further characterized by the inability to bind gp39 by Western blot.

49. The monoclonal antibody, antigen binding fragment or recombinant binding protein thereof of claim 47, wherein the antibody, antigen binding fragment or recombinant binding protein is further characterized by the ability to bind gp39 by Western blot.

50. Hybridoma HB 11808, HB 11809, HB 11810, HB 11811, HB 11812, HB 11813, HB 11814, HB 11815, HB 11816, HB 11817, HB 11818, HB 11819, HB 111820, HB 11821, HB 11822 or HB 11823 as deposited with the American Type Culture Collection.

* * * * *

UNITED STATES PATENT AND TRADEMARK OFFICE
CERTIFICATE OF CORRECTION

| | |
|---|---|
| PATENT NO. | : 5,876,950 |
| APPLICATION NO. | : 08/379057 |
| DATED | : March 2, 1999 |
| INVENTOR(S) | : Siadak et al. |

It is certified that error appears in the above-identified patent and that said Letters Patent is hereby corrected as shown below:

Claim 16, line 7, after "asparagine 180" insert --replaced by alanine--

Signed and Sealed this

Fifth Day of June, 2007

JON W. DUDAS
*Director of the United States Patent and Trademark Office*

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

AATCCTCAAA ATGCGGCACA TGTGATCAGT GCGGCCAGCA GTAAAACAAC A    51

( 2 ) INFORMATION FOR SEQ ID NO:2:

( i ) SEQUENCE CHARACTERISTICS:
( A ) LENGTH: 63 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

CAAAATGCGG CACATGTGAT CAGTGAGGCC GCCAGTAAAA CAGCATCTGT GTTACAGTGG    60

GCT    63

( 2 ) INFORMATION FOR SEQ ID NO:3:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

AGTAAAACAA CATCTGTGCT GCAGTGGGCT GAAGCAGGAT ACTACACCAT GAGC    54

( 2 ) INFORMATION FOR SEQ ID NO:4:

( i ) SEQUENCE CHARACTERISTICS:

( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

AGTAAAACAA CATCTGTGCT GCAGTGGGCT GAAAAAGGAG CCTACACCAT GAGCAACACT 60

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CAAGTCACCT TCTGTTCCGC TCGGGAGGCT TCGAGTCAAG CTCCA 45

( 2 ) INFORMATION FOR SEQ ID NO:6:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

AGCCTCTGCC TAAAGTCCCC CGGGAGAGCC GCGAGAATCT TACTCAGAGC T 51

( 2 ) INFORMATION FOR SEQ ID NO:7:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CGTCGATCTA GAGCATGTGC AAGTCCGATG AGTCCCCCCC CCCCCCC 47

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CGTCATAAGC TTCAGGAAGC ACACGACTGA GGCAC 35

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:9:

CGTCATAAGC TTGTCACCAT GGAGTTAGTT TG 32

(2) INFORMATION FOR SEQ ID NO: 10:

(i) SEQUENCE CHARACTERISTICS:
  (A) LENGTH: 37 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:10:

CGTCATAAGC TTGAACCAGT TGTATCTCCA CACCCAG 37

(2) INFORMATION FOR SEQ ID NO:11:

(i) SEQUENCE CHARACTERISTICS:
  (A) LENGTH: 384 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:11:

ATGAGTGTGC CCACTCAGGT CCTGGGGTTG CTGCTGCTGT GGCTTACAGG TGCCAGATGT 60
GACATCCAGA TGACTCAGTC TCCAGCCTCC CTATCTGCAT CTGTGGGAGA GACTGTCACC 120
ATCACATGTC GAGCAAGTGA GACTATTTAC AGTTATTTAG CTTGGTATCA GCAGAAACAG 180
GGAAGATCTC CTCAGCTCCT GGTCTATAAT GCAAAAACCT TAGCAGAAGG TGTGCCATCA 240
AGGTTCAGTG GCAGTGGATC AGGCACACAG TTTTCTCTGA AGATCAACAG CCTGCAGCCT 300
GAAGATTTTG GGAGTTATTA CTGTCAACAT CATTATAATA CTCCGCTCAC GTTCGGTACT 360
GGGACCAAGC TGGAGCTGAA ACGG 384

(2) INFORMATION FOR SEQ ID NO:12:

(i) SEQUENCE CHARACTERISTICS:
  (A) LENGTH: 128 amino acids
  (B) TYPE: amino acid
  (D) TOPOLOGY: linear (i i) MOLECULE TYPE: protein (v) FRAGMENT TYPE: N-terminal (x i) SEQUENCE DESCRIPTION: SEQ ID NO:12:

```
Met Ser Val Pro Thr Gln Val Leu Gly Leu Leu Leu Leu Trp Leu Thr
 1               5                  10                  15
Gly Ala Arg Cys Asp Ile Gln Met Thr Gln Ser Pro Ala Ser Leu Ser
                20                  25                  30
Ala Ser Val Gly Glu Thr Val Thr Ile Thr Cys Arg Ala Ser Glu Thr
                35                  40                  45
Ile Tyr Ser Tyr Leu Ala Trp Tyr Gln Gln Lys Gln Gly Arg Ser Pro
    50                  55                  60
Gln Leu Leu Val Tyr Asn Ala Lys Thr Leu Ala Glu Gly Val Pro Ser
65                  70                  75                  80
Arg Phe Ser Gly Ser Gly Ser Gly Thr Gln Phe Ser Leu Lys Ile Asn
                85                  90                  95
```

```
Ser  Leu  Gln  Pro  Glu  Asp  Phe  Gly  Ser  Tyr  Tyr  Cys  Gln  His  His  Tyr
               100                      105                     110

Asn  Thr  Pro  Leu  Thr  Phe  Gly  Thr  Gly  Thr  Lys  Leu  Glu  Leu  Lys  Arg
               115                      120                     125
```

( 2 ) INFORMATION FOR SEQ ID NO:13:

( i ) SEQUENCE CHARACTERISTICS:
        ( A ) LENGTH: 414 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

```
ATGAACTTCG  GGTTCAGCTT  GATTTTCCTT  GTCCTTGTTT  TAAAAGGTGT  CCAGTGTGAA       60
GTGAAGCTGG  TGGAGTCTGG  GGGAGGCTTA  GTGAAGCCTG  GAGGGTCCCT  GAAACTCTCC      120
TGTACAACCT  CTGGATTCAC  TTTCAATAAC  TATGCCATGT  CTTGGGTTCG  CCAGACTCCA      180
GAGAAGAGGC  TGGAGTGGGT  CGCATCCATT  AGTAGTGGTG  ATAGCACCTA  CTATCCAGAC      240
AGTGTGAGGG  GCCGATTCAC  CATCTCCAGA  GATAATGCCA  GGAACATCCT  GTATCTGCAA      300
ATGAGCAGTC  TGAGGTCTGA  GGACACGGCC  ATGTATTACT  GTGCAAGGCA  CTATGATTAC      360
GACAGCTATG  CTATGGACTA  CTGGGGTCAA  GGAACCTCAG  TCACCGTCTC  CTCA            414
```

( 2 ) INFORMATION FOR SEQ ID NO:14:

( i ) SEQUENCE CHARACTERISTICS:
        ( A ) LENGTH: 138 amino acids
        ( B ) TYPE: amino acid
        ( D ) TOPOLOGY: linear ( i i ) MOLECULE TYPE: protein ( v ) FRAGMENT TYPE: N-terminal ( x i ) SEQUENCE DESCRIPTION: SEQ ID NO:14:

```
Met  Asn  Phe  Gly  Phe  Ser  Leu  Ile  Phe  Leu  Val  Leu  Val  Leu  Lys  Gly
1               5                        10                      15

Val  Gln  Cys  Glu  Val  Lys  Leu  Val  Glu  Ser  Gly  Gly  Gly  Leu  Val  Lys
               20                       25                      30

Pro  Gly  Gly  Ser  Leu  Lys  Leu  Ser  Cys  Thr  Thr  Ser  Gly  Phe  Thr  Phe
               35                       40                      45

Asn  Asn  Tyr  Ala  Met  Ser  Trp  Val  Arg  Gln  Thr  Pro  Glu  Lys  Arg  Leu
     50                       55                       60

Glu  Trp  Val  Ala  Ser  Ile  Ser  Ser  Gly  Asp  Ser  Thr  Tyr  Tyr  Pro  Asp
65                       70                       75                       80

Ser  Val  Arg  Gly  Arg  Phe  Thr  Ile  Ser  Arg  Asp  Asn  Ala  Arg  Asn  Ile
               85                       90                       95

Leu  Tyr  Leu  Gln  Met  Ser  Ser  Leu  Arg  Ser  Glu  Asp  Thr  Ala  Met  Tyr
               100                      105                     110

Tyr  Cys  Ala  Arg  His  Tyr  Asp  Tyr  Asp  Ser  Tyr  Ala  Met  Asp  Tyr  Trp
               115                      120                     125

Gly  Gln  Gly  Thr  Ser  Val  Thr  Val  Ser  Ser
               130                      135
```

( 2 ) INFORMATION FOR SEQ ID NO:15:

( i ) SEQUENCE CHARACTERISTICS:
        ( A ) LENGTH: 396 base pairs
        ( B ) TYPE: nucleic acid (  C  ) STRANDEDNESS: single
(  D  ) TOPOLOGY: linear (  i  i  ) MOLECULE TYPE: cDNA (  x  i  ) SEQUENCE DESCRIPTION: SEQ ID NO:15:

| | | | | | |
|---|---|---|---|---|---|
| ATGGAGACAG | ACACACTCCT | GCTATGGGTG | CTGCTGCTCT | GGGTTCCAGG | TTCCACTGGT | 60 |
| GACATTGTGC | TGACACAGTC | TCCTGTTTCC | TTAGCTGTAT | CTCTGGGGCA | GAGGGTCACC | 120 |
| ATCTCATGCA | GGGCCAGCCA | AAGTGTCAGT | TCATCTACCA | ATAGTTATAT | GCACTGGTAC | 180 |
| CAACAGAAAC | CAGGACAGCC | ACCCAAACTC | CTCATCAAGT | ATGCATCCAA | CCTAGAATCT | 240 |
| GGGGTCCCTG | CCAGGTTCAG | TGGCAGTGGG | TCTGGGACAG | ACTTCACCCT | CAACATCCAT | 300 |
| CCTGTGGAGG | AGGAGGATAC | TGCAACATAT | TACTGTCAGC | ACAGTTGGGA | GATTCCATTC | 360 |
| ACGTTCGGCT | CGGGGACAAA | GTTGGAAATA | AGACGG | | | 396 |

(  2  ) INFORMATION FOR SEQ ID NO:16:

(  i  ) SEQUENCE CHARACTERISTICS:
(  A  ) LENGTH: 132 amino acids
(  B  ) TYPE: amino acid
(  D  ) TOPOLOGY: linear (  i  i  ) MOLECULE TYPE: protein (  v  ) FRAGMENT TYPE: N-terminal (  x  i  ) SEQUENCE DESCRIPTION: SEQ ID NO:16:

```
Met  Glu  Thr  Asp  Thr  Leu  Leu  Leu  Trp  Val  Leu  Leu  Leu  Trp  Val  Pro
 1                  5                      10                      15
Gly  Ser  Thr  Gly  Asp  Ile  Val  Leu  Thr  Gln  Ser  Pro  Val  Ser  Leu  Ala
                20                      25                      30
Val  Ser  Leu  Gly  Gln  Arg  Val  Thr  Ile  Ser  Cys  Arg  Ala  Ser  Gln  Ser
                35                      40                      45
Val  Ser  Ser  Ser  Thr  Asn  Ser  Tyr  Met  His  Trp  Tyr  Gln  Gln  Lys  Pro
        50                      55                      60
Gly  Gln  Pro  Pro  Lys  Leu  Leu  Ile  Lys  Tyr  Ala  Ser  Asn  Leu  Glu  Ser
65                      70                      75                      80
Gly  Val  Pro  Ala  Arg  Phe  Ser  Gly  Ser  Gly  Ser  Gly  Thr  Asp  Phe  Thr
                    85                      90                      95
Leu  Asn  Ile  His  Pro  Val  Glu  Glu  Glu  Asp  Thr  Ala  Thr  Tyr  Tyr  Cys
                    100                     105                     110
Gln  His  Ser  Trp  Glu  Ile  Pro  Phe  Thr  Phe  Gly  Ser  Gly  Thr  Lys  Leu
            115                     120                     125
Glu  Ile  Arg  Arg
            130
```

(  2  ) INFORMATION FOR SEQ ID NO:17:

(  i  ) SEQUENCE CHARACTERISTICS:
(  A  ) LENGTH: 411 base pairs
(  B  ) TYPE: nucleic acid
(  C  ) STRANDEDNESS: single
(  D  ) TOPOLOGY: linear (  i  i  ) MOLECULE TYPE: cDNA (  x  i  ) SEQUENCE DESCRIPTION: SEQ ID NO:17:

| | | | | | |
|---|---|---|---|---|---|
| ATGGGATGGA | GCTGGATCTT | TCTCTTTCTC | TTGTCAGGAA | CTGGAGGTGT | CCTCTCTGAG | 60 |
| GTCCAGCTGC | AACAGTCTGG | ACCTGAACTG | GTGAAACCTG | GGCTTCAGT | GAAGATGTCC | 120 |
| TGCAAGGCTT | CTGGATTCAC | TTTCAATAAC | TATGCCATGT | CTTGGGTTCG | CCAGACTCCA | 180 |

```
GAGAAGAGGC  TGGAGTGGAT  TGGAAATATT  AATCCTAACA  ATGGTGATAC  TTTCTTCAAC         240

CAGAAGTTCG  AGGGCAAGGC  CACGTTGACT  GTAGACAAAT  CCTCCAGCGC  AGCCTACATG         300

CAGCTCAACA  GCCTGACATC  TGAAGACTCT  GCAGTCTATT  ACTGTGCAAG  AGGGCCTGGG         360

ACGAACTACT  TTGACTACTG  GGGCCAAGGC  ACCACTCTCA  CAGTCTCCTC  A                  411
```

( 2 ) INFORMATION FOR SEQ ID NO:18:

( i ) SEQUENCE CHARACTERISTICS:
        ( A ) LENGTH: 137 amino acids
        ( B ) TYPE: amino acid
        ( D ) TOPOLOGY: linear ( i i ) MOLECULE TYPE: protein ( v ) FRAGMENT TYPE: N-terminal ( x i ) SEQUENCE DESCRIPTION: SEQ ID NO:18:

```
Met  Gly  Trp  Ser  Trp  Ile  Phe  Leu  Phe  Leu  Leu  Ser  Gly  Thr  Gly  Gly
1              5                        10                       15
Val  Leu  Ser  Glu  Val  Gln  Leu  Gln  Gln  Ser  Gly  Pro  Glu  Leu  Val  Lys
              20                       25                       30
Pro  Gly  Ala  Ser  Val  Lys  Met  Ser  Cys  Lys  Ala  Ser  Gly  Tyr  Thr  Phe
              35                       40                       45
Thr  Asp  Tyr  Tyr  Met  Lys  Trp  Val  Lys  Gln  Ser  His  Gly  Lys  Ser  Leu
     50                       55                       60
Glu  Trp  Ile  Gly  Asn  Ile  Asn  Pro  Asn  Asn  Gly  Asp  Thr  Phe  Phe  Asn
65                            70                       75                       80
Gln  Lys  Phe  Glu  Gly  Lys  Ala  Thr  Leu  Thr  Val  Asp  Lys  Ser  Ser  Ser
              85                       90                       95
Ala  Ala  Tyr  Met  Gln  Leu  Asn  Ser  Leu  Thr  Ser  Glu  Asp  Ser  Ala  Val
              100                      105                      110
Lys  Lys  Cys  Ala  Arg  Gly  Pro  Gly  Thr  Asn  Tyr  Phe  Asp  Tyr  Trp  Gly
              115                      120                      125
Gln  Gly  Thr  Thr  Leu  Thr  Val  Ser  Ser
     130                      135
```

( 2 ) INFORMATION FOR SEQ ID NO:19:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

```
ATCGTCTAGG  TCGACATTGT  GCTGACACAG  TCTCCTGTTT  CC                              42
```

( 2 ) INFORMATION FOR SEQ ID NO:20:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

```
GCCACCCGAC  CCACCACCGC  CCGAGCCACC  GCCACCCCGT  CTTATTTCCA  ACTTTGTCCC         60
```

( 2 ) INFORMATION FOR SEQ ID NO:21:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

TCGGGCGGTG GTGGGTCGGG TGGCGGCGGA TCTGAGGTCC AGCTGCAACA GTCTGGACCT 60

( 2 ) INFORMATION FOR SEQ ID NO:22:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

TCAGTGCTGA TCAGAGGAGA CTGTGAGAGT GGTGCCTTGG CC 42

( 2 ) INFORMATION FOR SEQ ID NO:23:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

ATCGTCTAGG TCGACATCCA GATGACTCAG TCTCCAGCCT CC 42

( 2 ) INFORMATION FOR SEQ ID NO:24:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

GCCACCCGAC CCACCACCGC CAGCGCCACC GCCACCCCGT TTCAGCTCCA GCTTGGTCCC 60

( 2 ) INFORMATION FOR SEQ ID NO:25:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

TCGGGCGGTG GTGGGTCGGG TGGCGGCGGA TCTGAAGTGA AGCTGGTGGA GTCTGGGGGA 60

( 2 ) INFORMATION FOR SEQ ID NO:26:

( i ) SEQUENCE CHARACTERISTICS:
        ( A ) LENGTH: 42 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:26:

```
TCAGTGCTGA TCAGAGGAGA CGGTGACTGA GGTTCCTTGA CC                     42
```

(2) INFORMATION FOR SEQ ID NO:27:

(i) SEQUENCE CHARACTERISTICS:
(A) LENGTH: 108 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:27:

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Thr Ile Tyr Ser Tyr
            20                  25                  30

Leu Ala Trp Tyr Gln Gln Lys Gln Gly Arg Ser Pro Gln Leu Leu Val
            35                  40                  45

Tyr Asn Ala Lys Thr Leu Ala Glu Gly Val Pro Ser Arg Phe Ser Gly
            50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Asn Thr Pro Leu
                85                  90                  95

Thr Phe Gly Thr Gly Thr Lys Leu Glu Leu Lys Arg
                100                 105
```

(2) INFORMATION FOR SEQ ID NO:28:

(i) SEQUENCE CHARACTERISTICS:
(A) LENGTH: 108 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:28:

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Thr Ile Tyr Ser Tyr
            20                  25                  30

Leu Ala Trp Tyr Gln Gln Lys Pro Gly Lys Ala Pro Lys Leu Leu Val
            35                  40                  45

Tyr Asn Ala Lys Thr Leu Ala Glu Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asn Thr Pro Leu
                85                  90                  95

Thr Phe Gly Gly Gly Thr Lys Val Glu Ile Lys Arg
                100                 105
```

( 2 ) INFORMATION FOR SEQ ID NO:29:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:29:

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Leu
                 85                  90                  95
Thr Phe Gly Gly Gly Thr Lys Val Glu Ile Lys Arg
            100                 105
```

( 2 ) INFORMATION FOR SEQ ID NO:30:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:30:

```
Glu Val Lys Leu Val Glu Ser Gly Gly Leu Val Lys Pro Gly Gly
 1               5                  10                  15
Ser Leu Lys Leu Ser Cys Thr Thr Ser Gly Phe Thr Phe Asn Asn Tyr
            20                  25                  30
Ala Met Ser Trp Val Arg Gln Thr Pro Glu Lys Arg Leu Glu Trp Val
         35                  40                  45
Ala Ser Ile Ser Ser Gly Asp Ser Thr Tyr Tyr Phe Asp Ser Val Arg
     50                  55                  60
Gly Arg Phe Thr Ile Ser Arg Asp Asn Ala Arg Asn Ile Leu Tyr Leu
 65                  70                  75                  80
Gln Met Ser Ser Leu Arg Ser Glu Asp Thr Ala Met Tyr Tyr Cys Ala
                 85                  90                  95
Arg His Tyr Asp Tyr Asp Ser Tyr Ala Met Asp Tyr Trp Gly Gln Gly
            100                 105                 110
Thr Ser Val Thr Val Ser
            115
```

( 2 ) INFORMATION FOR SEQ ID NO:31:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:31:

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |
| Ser | Leu | Arg | Leu | Ser | Cys | Ala | Ser | Gly | Phe | Thr | Phe | Asn | Asn | Tyr | Ala |
| | | | 20 | | | | | 25 | | | | | 30 | | |
| Met | Ser | Trp | Val | Arg | Gln | Ala | Pro | Gly | Lys | Gly | Leu | Glu | Trp | Val | Ala |
| | | 35 | | | | | 40 | | | | | 45 | | | |
| Ser | Ile | Ser | Ser | Gly | Ile | Tyr | Tyr | Ala | Asp | Ser | Val | Lys | Gly | Arg | Phe |
| | 50 | | | | | 55 | | | | | 60 | | | | |
| Thr | Ile | Ser | Arg | Asp | Asn | Ala | Lys | Asn | Ile | Leu | Tyr | Leu | Gln | Met | Asn |
| 65 | | | | | 70 | | | | | 75 | | | | | 80 |
| Ser | Leu | Arg | Ala | Glu | Asp | Thr | Ala | Val | Tyr | Tyr | Cys | Ala | Arg | His | Tyr |
| | | | | 85 | | | | | 90 | | | | | 95 | |
| Asp | Tyr | Asp | Ser | Tyr | Ala | Met | Asp | Tyr | Trp | Gly | Gln | Gly | Thr | Leu | Val |
| | | | | 100 | | | | | 105 | | | | | 110 | |
| Thr | Val | Ser | | | | | | | | | | | | | |
| | | 115 | | | | | | | | | | | | | |

( 2 ) INFORMATION FOR SEQ ID NO:32:

( i ) SEQUENCE CHARACTERISTICS:
( A ) LENGTH: 109 amino acids
( B ) TYPE: amino acid
( D ) TOPOLOGY: linear ( i i ) MOLECULE TYPE: protein ( v ) FRAGMENT TYPE: internal ( x i ) SEQUENCE DESCRIPTION: SEQ ID NO:32:

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Ser | Met | Asn | Trp | Val | Arg | Gln | Ala | Pro | Gly | Lys | Gly | Leu | Glu | Trp | Val |
| | | 35 | | | | | 40 | | | | | 45 | | | |
| Ser | Ser | Ile | Ser | Ser | Ser | Ser | Tyr | Ile | Tyr | Tyr | Ala | Asp | Ser | Val | Lys |
| | 50 | | | | | 55 | | | | | 60 | | | | |
| Gly | Arg | Phe | Thr | Ile | Ser | Arg | Asp | Asn | Ala | Lys | Asn | Ser | Leu | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Ala |
| | | | | 85 | | | | | 90 | | | | | 95 | |
| Arg | Asp | Tyr | Trp | Gly | Gln | Gly | Thr | Leu | Val | Thr | Val | Ser | | | |
| | | | 100 | | | | 105 | | | | | | | | |

( 2 ) INFORMATION FOR SEQ ID NO:33:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:33:

ATCGTCTAGA AGCTTGTCGA CATCCAGATG ACTCAGTCTC CATCATCCCT ATCTGCATCT      60

GTGGGAGATC GAGTCACCAT CACATGTCGA GCAAGT 96

(2) INFORMATION FOR SEQ ID NO:34:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

TAGTAGCTTA GGTGCCTTTC CAGGTTTCTG CTGATACCAA GCTAA 45

(2) INFORMATION FOR SEQ ID NO:35:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

CCTGGAAAGG CACCTAAGCT ACTAGTCTAT AATGCAAAAA CCTTAGCAAA AACCTTAGCA 60

(2) INFORMATION FOR SEQ ID NO:36:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

GAGATCGTCA GTGTAAAGTC TGTGCCTGAT CCACTGCCAC TGAAC 45

(2) INFORMATION FOR SEQ ID NO:37:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

GACTTTACAC TGACGATCTC AAGCCTGCAG CCTGAAGATT TTGCAACTTA TTACTGTCAA 60

CATCATTATA ATACT 75

(2) INFORMATION FOR SEQ ID NO:38:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

TCAGTGCTTC TAGAGCCACC CCGTTTGATC TCGACCTTGG TCCCTCCACC GAACGTGAGC 60

GGAGTATTAT AATGATGTTG AC 82

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

ATCGTCTAGA AGCTTGTCGA CATC 24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

TCAGTGCTTC TAGAGCCACC CCGT 24

(2) INFORMATION FOR SEQ ID NO:41:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

ATCGTCTAGA AGCTTGAAGT GCAGCTGGTG GAGTCTGGAG GAGGCTTAGT GAAGCCTGGA 60

GGGTCCCTGA GGCTCTCCTG TGCAACCTCT GGATTCACTT TCAATA 106

(2) INFORMATION FOR SEQ ID NO:42:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

ATCGTCTAGA AGCTTGAAGT GCAGCTGGTG GAGTCTGGAG GAGGCTTAGT GAAGCCTGGA 60

GGGTCCCTGA GGCTCTCCTG TGCAGCCTCT GGATTCACTT TCAATA 106

(2) INFORMATION FOR SEQ ID NO:43:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

TCAGTGCTCT AGAACCCTGC AGATCGAATT CAATGCTAGC GACCCACTCC AGTCCCTTAC 60

CTGGTGCCTG GCGAACCCAA GACATGG 87

( 2 ) INFORMATION FOR SEQ ID NO:44:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

CTAGCATTAG TAGTGGTAGT TACATCTACT ATGCTGACAG TGTGAAAGGC CGATTCACCA 60

TCTCGAGAGA TAATGCCAAA AACATCCTGT ATCTGCA 97

( 2 ) INFORMATION FOR SEQ ID NO:45:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

GATACAGGAT GTTTTGGCA TTATCTCTCG AGATGGTGAA TCGGCCTTTC ACACTGTCAG 60

CATAGTAGAT GTAACTACCA CTACTAATG 89

( 2 ) INFORMATION FOR SEQ ID NO:46:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

CTAGCATTAG TAGTGGTGAT TACATCTACT ATGCTGACAG TGTGAAAGGC CGATTCACCA 60

TCTCGAGAGA TAATGCCAAA AACATCCTGT ATCTGCA 97

( 2 ) INFORMATION FOR SEQ ID NO:47:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

GATACAGGAT GTTTTGGCA TTATCTCTCG AGATGGTGAA TCGGCCTTTC ACACTGTCAG 60

CATAGTAGAT GTAATCACCA CTACTAATG 89

( 2 ) INFORMATION FOR SEQ ID NO:48:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

CTAGCATTAG TAGTGGTAGT AGCATCTACT ATGCTGACAG TGTGAAAGGC CGATTCACCA 60

TCTCGAGAGA TAATGCCAAA AACATCCTGT ATCTGCA 97

( 2 ) INFORMATION FOR SEQ ID NO:49:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

GATACAGGAT GTTTTTGGCA TTATCTCTCG AGATGGTGAA TCGGCCTTTC ACACTGTCAG 60

CATAGTAGAT GCTACTACCA CTACTAATG 89

( 2 ) INFORMATION FOR SEQ ID NO:50:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

CTAGCATTAG TAGTGGTGAT AGCATCTACT ATGCTGACAG TGTGAAAGGC CGATTCACCA 60

TCTCGAGAGA TAATGCCAAA AACATCCTGT ATCTGCA 97

( 2 ) INFORMATION FOR SEQ ID NO:51:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

GATACAGGAT GTTTTTGGCA TTATCTCTCG AGATGGTGAA TCGGCCTTTC ACACTGTCAG 60

CATAGTAGAT GCTATCACCA CTACTAATG 89

( 2 ) INFORMATION FOR SEQ ID NO:52:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

ATCGTCTAGC TGCAGATGAA CAGTCTGAGG GCAGAGGACA CGGCCGTCTA TTACTGTGCA 60

AGGCACTATG ATTACGAC 78

( 2 ) INFORMATION FOR SEQ ID NO:53:

( i ) SEQUENCE CHARACTERISTICS:

( A ) LENGTH: 69 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:53:

TCAGTGCTCT AGATGATCAG AGGAGACGGT GACCAGGGTT CCTTGACCCC AGTAGTCCAT    60

AGCATAGCT    69

( 2 ) INFORMATION FOR SEQ ID NO:54:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:54:

ATCGTCTAGG TCGACATCCA GATGACTCAG TCTCCATCAT CC    42

( 2 ) INFORMATION FOR SEQ ID NO:55:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:55:

GCCACCCGAC CCACCACCGC CAGCGCCACC GCCACCCCGT TTGATCTCGA CCTTGGTCCC    60

( 2 ) INFORMATION FOR SEQ ID NO:56:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:56:

TCGGGCGGTG GTGGGTCGGG TGGCGGCGGA TCTGAAGTGC AGCTGGTGGA GTCTGGAGGA    60

( 2 ) INFORMATION FOR SEQ ID NO:57:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:57:

TCAGTGCTGA TCAGAGGAGA CGGTGACCAG GGTTCCTTGA CC    42